United States Patent [19]

Beeley et al.

[11] Patent Number: 5,726,165
[45] Date of Patent: Mar. 10, 1998

[54] DERIVATIVES OF 4-(2-AMINOETHYL) PHENOXYMETHYL-PHOSPHONIC AND -PHOSPHINIC ACID AND PHARMACEUTICAL AND VETERINARY USES THEREFOR

[75] Inventors: Lee James Beeley, Dorking; Mervyn Thompson, Harlow; David Kenneth Dean, Dorking; Nikesh Rasiklal Kotecha, Welwyn Garden City; John Michael Berge, Merstham; Robert William Ward, Great Dunmow, all of England

[73] Assignee: SmithKline Beecham p.l.c., Brentford, England

[21] Appl. No.: 465,486

[22] Filed: Jun. 5, 1995

[30] Foreign Application Priority Data

Jul. 29, 1994 [GB] United Kingdom ............... 9415304
Nov. 17, 1994 [GB] United Kingdom ............... 9423179

[51] Int. Cl.⁶ ............... A61K 31/665; A61K 31/66; C07F 9/665; C07F 9/40
[52] U.S. Cl. ............... 514/114; 514/110; 514/465; 514/539; 514/562; 514/567; 549/436; 558/77; 558/186; 558/187; 560/9; 560/42; 562/11; 562/426; 562/451
[58] Field of Search ............... 549/436; 558/187; 560/42; 562/11, 451; 514/114, 465, 539, 567

[56] References Cited

U.S. PATENT DOCUMENTS

| | | | |
|---|---|---|---|
| 4,892,886 | 1/1990 | Alig et al. | 514/567 |
| 4,999,377 | 3/1991 | Caulkett et al. | 514/507 |
| 5,480,908 | 1/1996 | Epstein et al. | 514/465 |
| 5,488,064 | 1/1996 | Sher | 514/465 |

OTHER PUBLICATIONS

Database Caplus on STN, Chemical Abstracts Service (Columbus, OH), Accession No. 1995:750531, Beeley, L.J. et al., "Preparation of N-[(4-acylmethoxy)phenylpropyl]-N-(oxobenzazolyloxy)propanolamines as Adrenoceptor Agonists", abstract, WO 9504047 A1, Feb. 1995.

*Primary Examiner*—Michael G. Ambrose
*Attorney, Agent, or Firm*—Soma G. Simon; Charles M. Kinzig; Edward T. Lentz

[57] ABSTRACT

A compound of formula (I):

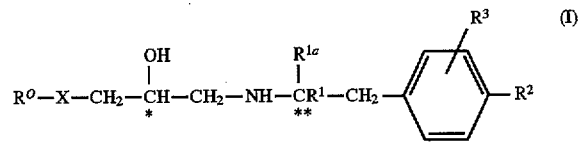

or a pharmaceutically acceptable salt, or solvate thereof, wherein, $R^o$ represents an aryl group, optionally substituted;

X represents O or S;

$R^1$ and $R^{1a}$ each independently represents hydrogen or an alkyl group;

$R^2$ represents $OCH_2CO_2H$, or an ester or amide thereof, or $R^2$ represents a moiety of formula (b):

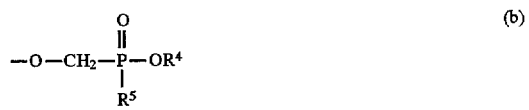

wherein $R^4$ represent hydrogen, alkyl, hydroxyalkyl, arylalkyl, aralkyloxyalkyl or cycloalkyl and $R^5$ represent hydroxy, alkoxy, arylalkyloxy, hydroxyalkyloxy, alkoxyalkyloxy, arylalkoxyalkyloxy, cycloalkyloxy, hydrogen, alkyl, substituted alkyl, cycloalkyl, aryl, arylalkyl, arylalkyloxyalkyl or $R^5$ together with $OR^4$ represents $O(CH_2)_nO$ wherein n is 2, 3 or 4; and $R^3$ represents hydrogen, halogen, alkyl or alkoxy or $R^3$ together with $R^2$ represents a moiety of formula (c):

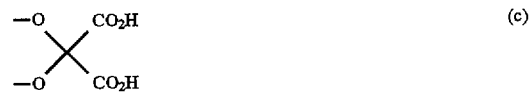

or an ester or amide thereof; a pharmaceutical composition containing such a compound, a process of preparing such a compound and the use of such a compound in medicine.

17 Claims, No Drawings

DERIVATIVES OF 4-(2-AMINOETHYL) PHENOXYMETHYL-PHOSPHONIC AND -PHOSPHINIC ACID AND PHARMACEUTICAL AND VETERINARY USES THEREFOR

This invention relates to novel compounds, to a process for preparing such compounds, to pharmaceutical compositions containing such compounds and to the use of such compounds and compositions in medicine and agriculture.

European Patent Application, Publication Number 0328251 discloses certain 2-(2-hydroxy-3-phenoxypropylamino)ethylphenoxyacetamides which are stated to be useful in the treatment of obesity and related conditions.

It has now surprisingly been discovered that a particular series of novel aryloxy and arylthio propanolamine derivatives have good $\beta_3$-adrenoreceptor agonist activity and in particular show good selectivity for $\beta_3$-adrenoreceptors over the $\beta_1$- or $\beta_2$-adrenoreceptors, to the extent that these compounds are antagonists of the $\beta_1$- and $\beta_2$-adrenoreceptors. These compounds are indicated to have good anti-hyperglycaemic and/or anti-obesity activity coupled with especially good selectivity from cardiac and tremorigenic side effects.

These compounds are also indicated to have potential in the treatment of gastrointestinal disorders such as peptic ulceration, oesophagitis, gastritis and duodenitis, intestinal ulcerations, including inflammatory bowel disease, and irritable bowel syndrome and also for the treatment of gastrointestinal ulcerations, especially when induced by non-steroidal anti-inflammatory drugs or corticosteroids.

These compounds may also be of use in increasing the high-density-lipoprotein (HDL) cholesterol concentration and decreasing the triglyceride concentration in human blood serum and are therefore of potential use in the treatment and/or prophylaxis of atherosclerosis. They are also indicated to be useful for the treatment of hyperinsulinaemia. They are also indicated to be useful for the treatment of depression.

These compounds also have potential as growth promoters for livestock and for decreasing birth mortality rate and increasing the post-natal survival rate in livestock.

Accordingly the present invention provides a compound of formula (I):

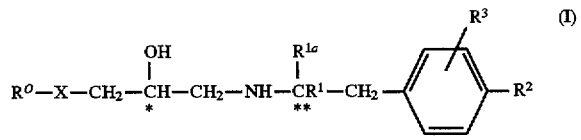

or a pharmaceutically acceptable salt thereof, or a pharmaceutically acceptable solvate thereof, wherein, $R^o$ represents an aryl group optionally substituted with one, two or three substitutents selected from the list consisting of: hydroxy, hydroxymethyl, nitro, amino, alkylamino, dialkylamino, alkylsulphonamido, arylsulphonamido, formamido, halogen, alkoxy and allyl;

X represents O or S;

$R^1$ and $R^{1a}$ each independently represents hydrogen or an alkyl group;

$R^2$ represents $OCH_2CO_2H$, or an ester or amide thereof, or $R^2$ represents a moiety of formula (b):

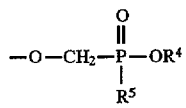

wherein $R^4$ represent hydrogen, alkyl, hydroxyalkyl, arylalkyl, aralkyloxyalkyl or cycloalkyl and $R^5$ represent hydroxy, alkoxy, arylalkyloxy, hydroxyalkyloxy, alkoxyalkyloxy, arylalkoxyalkyloxy or cycloalkyloxy or $R^5$ represents hydrogen, alkyl, substituted alkyl, cycloalkyl, aryl, arylalkyl, arylalkyloxyalkyl or $R^5$ together with $OR^4$ represents $O(CH_2)_nO$ wherein n is 2, 3 or 4; and $R^3$ represents hydrogen, halogen, alkyl or alkoxy or $R^3$ together with $R^2$ represents a moiety of formula (c):

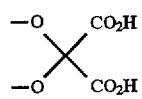

or an ester or amide thereof; providing that 4-[2-[2-hydroxy-3-(4-hydroxyphenoxy)propylamino]propyl]phenoxyacetic acid and salts and esters thereof and the examples disclosed in EP0328251 are excluded from the scope of formula (I).

Suitable aryl groups include phenyl or naphthyl groups, especially phenyl groups.

Suitably, $R^o$ represents a phenyl group optionally substituted with hydroxy and/or hydroxymethyl.

Examples of $R^o$ include 4-hydroxy-3-hydroxymethylphenyl, 3- and 4-hydroxyphenyl groups.

Suitably, $R^1$ is an alkyl group and $R^{1a}$ represents hydrogen.

Suitably, $R^1$ and $R^{1a}$ each represents hydrogen.

When $R^1$ is alkyl, it is favourably a $C_{1-6}$ alkyl group, especially a methyl group.

Suitably, $R^{1a}$ represents hydrogen.

In one aspect, $R^2$ represents $OCH_2CO_2H$, or an ester or amide thereof.

Suitably, $R^3$ together with $R^2$ represents a moiety of formula (c) or $R^2$ represents a moiety of formula (b) and $R^3$ represents hydrogen, halogen, alkyl or alkoxy.

In one aspect, $R^2$ represents a moiety of formula (b).

In one aspect of the invention, $R^3$ together with $R^2$ represents a moiety of formula (c).

Preferably, $R^2$ is a moiety of formula (b).

Favorably, $R^3$ represents hydrogen, halogen, alkyl or alkoxy.

Preferably, $R^3$ is hydrogen.

Suitably, $R^4$ represent hydrogen, alkyl, hydroxyalkyl, phenylalkyl, benzyloxyalkyl or cycloalkyl.

When $R^4$ represents alkyl, especially $C_{1-6}$ alkyl, examples include ethyl and butyl, especially n-butyl.

When $R^4$ represents hydroxyalkyl, an example is hydroxypropyl.

When $R^4$ represents arylalkyl, an example is phenylpropyl.

When $R^4$ represents arylalkyloxyalkyl, an example is benzyloxyethyl.

Favourably, $R^4$ represent hydrogen or alkyl, especially hydrogen.

When $R^5$ represents substituted alkyl, suitable substituents are selected from: hydroxy, alkoxy and arylalkoxy.

Suitably, $R^5$ represents hydroxy, alkoxy, arylalkyloxy, hydroxyalkyloxy, alkoxyalkyloxy, arylalkoxyalkyloxy or cycloalkyloxy, especially alkoxy, hydroxyalkyloxy or arylalkoxyalkyloxy.

When $R^5$ represents alkoxy, especially $C_{1-6}$ alkoxy, examples include ethoxy and n-butoxy.

When $R^5$ represents arylalkyloxy an example is phenylpropyloxy.

When $R^5$ represents arylalkoxyalkyloxy an example is benzyloxypropyloxy.

Suitably, in the hydroxyalkyloxy group represented by $R^5$ the hydroxy group is substituted on the terminal carbon atom of the alkyl group, for example as in a 2-hydroxyethyloxy group and a 3-hydroxypropyloxy group.

Favourably, $R^5$ represents hydrogen, alkyl, substituted alkyl, cycloalkyl or aryl.

When $R^5$ represents cycloalkyl an example is cyclohexyl.

Preferably, $R^5$ represents alkyl for example n-hexyl.
Preferably, $R^5$ represents aryl for example phenyl.

When $R^5$ represents alkyl examples include n-hexyl.

Preferably, $R^4$ represent alkyl, especially $C_{1-6}$ alkyl, for example ethyl, and $R^5$ represent alkoxy, especially $C_{1-6}$ alkoxy, for example ethoxy.

In another aspect, $R^4$ is alkyl, for example ethyl, and $R^5$ is hydrogen.

Preferably, X represents O.

In one particular aspect the invention provides a subgroup of the compounds of formula (I) wherein $R^o$, $R^1$, $R^{1a}$ and X are as defined in relation to formula (I) and $R^2$ represents a moiety of formula (b) and $R^3$ represents hydrogen, halogen, alkyl or alkoxy or $R^3$ together with $R^2$ represents a moiety of formula (c), such compounds shall hereinafter be referred to as compounds of formula (IA).

The compounds of formula (I) have one or two asymmetric carbon atoms, marked with an asterisk (*) or two asterisks (**) in the formula. These compounds may therefore exist in up to four stereoisomeric forms. The present invention encompasses all stereoisomers of the compounds of the general formula (I) whether free from other isomers, or admixed with other isomers in any proportion, such as mixtures of diastereoisomers and racemic mixtures of enantiomers.

In addition when the substituents on the phosphorous atom of moiety (b) are different and other than OH the phosphorous atom is chiral: The invention extends to mixed and separated isomers of such compounds in an analogous fashion to that discussed for chiral carbon atoms.

Preferably, the asymmetric carbon atom indicated by a single asterisk (*) is in the S-configuration.

Preferably, the asymmetric carbon atom indicated by two asterisks (**) is in the R-configuration.

One suitable form of a compound of formula (I) is a mixture of the SR and RS enantiomers.

One favoured form of a compound of formula (I) is the SR enantiomer.

The term 'alkyl' when used alone or when forming part of other groups (such as the 'alkoxy' group) includes straight- or branched-chain alkyl groups containing 1 to 12 carbon atoms, suitably 1 to 6 carbon atoms, examples include methyl, ethyl, n-propyl, isopropyl, n-butyl, isobutyl or tert-butyl group.

The term 'cycloalkyl' includes $C_{3-8}$ cycloalkyl groups, especially $C_5$ or $C_6$ cycloalkyl groups.

When used herein the term "halogen" refers to fluorine, chlorine, bromine and iodine, preferably fluorine or chlorine.

Suitable pharmaceutically acceptable esters of carboxyl groups include alkyl esters, especially $C_{1-6}$ alkyl esters such as methyl.

Suitable pharmaceutically acceptable amides are those of formula —$CONR^sR^t$ wherein $R^s$ and $R^t$ each independently represent hydrogen, alkyl or alkoxyalkyl.

Suitable pharmaceutically acceptable salts include acid addition salts, salts of carboxy groups and salts of phosphonic acid groups. Salts of phosphinic acids are also suitable pharmaceutically acceptable salts of the invention.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid or acetylsalicylic acid.

Suitable pharmaceutically acceptable salts of carboxy groups, phosphonic acid or phosphinic acid groups include metal salts, such as for example aluminium, alkali metal salts such as sodium or potassium and lithium, alkaline earth metal salts such as calcium or magnesium and ammonium or substituted ammonium salts, for example those with $C_{1-6}$ alkylamines such as methylamine, hydroxy-$C_{1-6}$ alkylamines such as 2-hydroxyethylamine, bis-(2-hydroxyethyl)-amine or tri-(2-hydroxyethyl)-amine, cycloalkylamines such as bicyclohexylamine, or with procaine, 1,4-dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable pharmaceutically acceptable solvates are conventional solvates, preferably hydrates.

In a further aspect the invention also provides a process for the preparation of a compound of formula (I) or a pharmaceutically acceptable acid addition salt or a pharmaceutically acceptable solvate thereof, which process comprises reacting a compound of formula (II):

$$R^{o'}-X-CH_2-CH\underset{O}{\overset{}{\diagdown\diagup}}CH_2 \qquad (II)$$

wherein X is as defined in relation to formula (I) and $R^o$ represents $R^o$ as defined in relation to formula (I) or a protected form thereof, with a compound of formula (III):

$$T^oNH-\underset{**}{CR^1}-CH_2-\underset{}{\diagup\!\!\diagdown}\!\!\!\!\overset{R^{1a}}{\vert}\!\!\!-\!\!\diagdown\!\!\!\diagup\overset{R^3}{\underset{R^2}{}}\qquad (III)$$

wherein $R^1$, $R^{1a}$, $R^2$ and $R^3$ are as defined in relation to formula (I) and $T^o$ represents a hydrogen or a protecting group; and thereafter, if required, carrying out one or more of the following optional steps:

(i) converting a compound of formula (I) to a further compound of formula (I);

(ii) removing any protecting group;

(iii) preparing a pharmaceutically acceptable salt of the compound of formula (I) and/or a pharmaceutically acceptable solvate thereof.

The reaction between compounds of formulae (II) and (III) may be carried out in any suitable solvent, such as methanol, at any temperature providing a suitable rate of formation of the required product, generally at an elevated temperature such as the reflux temperature of the solvent; preferably under an inert atmosphere such as nitrogen or argon, alternatively the reaction between compounds of formulae (II) and (III) may be carried out in a chlorinated solvent such as dichloromethane or in an aprotic solvent such as acetonitrile; suitably the reaction is carried out in the presence of a catalyst such as ytterbium triflate as described in Tetrahedron Letters, 1994, 35(3), 433 or a perchlorate such as lithium perchlorate.

Suitably R⁰' represents a protected form of R⁰, suitable protected forms being as defined herein.

Suitable protecting groups represented by T⁰ are benzyl or p-methoxybenzyl groups.

A compound of formula (II) may be prepared by reacting an activated form of a compound of formula (IV):

wherein R⁰' and X are as defined in relation to formula (II), with a compound of formula (V):

wherein L⁰ represents a leaving group.

A suitable activated form of a compound of formula (IV) is an ionic form, such as an alkali metal salted form, for example a potassium salted form.

An activated form of a compound of formula (IV) may be prepared by use of the appropriate conventional procedure, for example a salted form may be prepared by treating the compound of formula (IV) with a base such as an alkali carbonate, for example potassium carbonate.

Suitably, L⁰ represents a tosylate or a 3-nitrobenzenesulphonyloxy group.

The reaction between the compounds of formulae (IV) and (V) may be carried out in an aprotic solvent such as acetone or dimethylformamide at any temperature providing a suitable rate of formation of the required product, generally at an ambient to elevated temperature, suitably an elevated temperature, such as the reflux temperature of the solvent.

L⁰ also represents OH.

When L⁰ represents OH, the compound of formula (V) is oxiranyl-methanol and the reaction between it and the compound of formula (IV) is conveniently effected using a Mitsunobu reaction, according to methods disclosed in Tetrahedron Letters., 1994, 35, 5997–6000 and Organic Reactions 1992, 42, 335–656.

A compound of formula (III), wherein R¹ is not hydrogen, is suitably prepared by the hydrogenolysis of a compound of formula (VI):

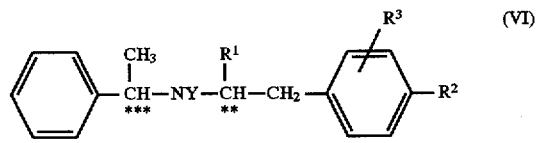

wherein R¹, R² and R³ are as defined in relation to formula (I), Y represents hydrogen or a moiety —B(OH)₂ and the CH carbon and *CH carbon atoms are chiral carbon atoms.

Suitably, catalytic hydrogenolysis is used, using for example 10% palladium on charcoal in the presence of ammonium formate, suitably in an alkanolic solvent such as methanol, at any temperature providing a convenient rate of formation of the required product, for example at ambient temperature; preferably the reaction is carried out in an inert atmosphere, generally under nitrogen.

A compound of formula (VI) wherein Y is a moiety B(OH)₂ may be prepared from a corresponding compound of formula (VI) wherein Y is H, by treatment with boron tribromide in an inert solvent such as methylene chloride at ambient temperature, preferably in an inert atmosphere such as argon, followed by removal of Y using catalytic hydrogenolysis, using for example a palladium on carbon catalyst.

A compound of formula (VI) wherein Y is H may be prepared by stereoselective reduction of a compound of formula (VII):

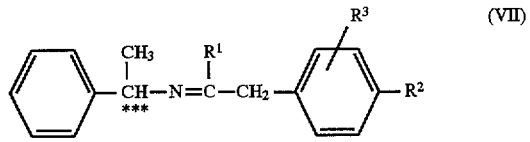

wherein R¹, R² and R³ are as defined in relation to formula (I) and the ***C carbon is a chiral carbon.

The reduction of the compound of formula (VII) may be carried out using catalytic reduction in the presence of hydrogen.

A preferred catalyst is platinum oxide.

Suitable reduction conditions include using an alkanol solvent such as methanol or ethanol, at any temperature providing a convenient rate of formation of the required product, conveniently at ambient temperature using a pressure of 1–5 atmospheres of hydrogen.

The compound of formula (VII) may be prepared by reacting a compound of formula (VIII):

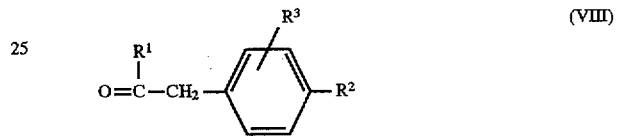

wherein R¹, R² and R³ are as defined in relation to formula (I), with R-α-methylbenzylamine.

The reaction between compounds of formulae (VIII) and R-α-methylbenzylamine may be carried out under conventional amination conditions, for example in a solvent such as methanol or toluene.

Conveniently, the compound of formula (VII) is prepared in-situ by reacting a compound of the above defined formula (VIII) with R-α-methylbenzyl amine and thereafter reducing the compound of formula (VII) so formed using reaction conditions and catalysts as described above.

The compounds of formula (VIII) wherein R² represents OCH₂CO₂H or an ester or amide thereof or wherein R₂ represents a moiety of the above defined formula (b) wherein R⁵ represent hydroxy, alkoxy, hydroxyalkyloxy or cycloalkyloxy or R⁵ together with OR⁴ represents O(CH₂)ₙO, are known compounds or they may be prepared by processes analogous to those used to prepare such compounds, for example they may be prepared according to methods disclosed in European Patent Application, Publication Number 0023385 or International Application number WO 94/02493.

A compound of formula (VIII) such as those wherein R² represents a moiety of the above defined formula (b) wherein R⁵ represent hydrogen, alkyl, substituted alkyl, cycloalkyl or aryl may be prepared by reducing a compound of formula (IX):

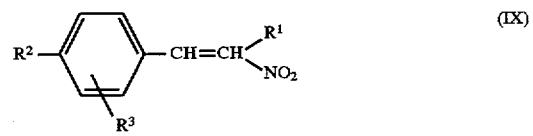

wherein R¹ and R³ are as defined in relation to formula (I) and as stated R² is as defined in relation to the required compounds of formula (VIII).

The reduction of the compound of formula (IX) may conveniently be carried out using iron powder in the presence of acetic acid in an aqueous solvent such as aqueous methanol, at any temperature providing a suitable rate of formation of the required product, generally at an elevated temperature and conveniently at the reflux temperature of the solvent.

A compound of formula (IX) may be prepared by reacting a compound of formula (X):

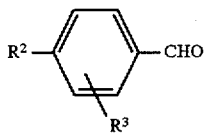

wherein, $R^2$ and $R^3$ are as defined in relation to formula (IX), with a nitroalkane, such as nitromethane or nitroethane.

Generally, the carbon atom of the —CHO group in the compound of formula (X) is in an activated form, a suitable activated form being provided by forming an imine of the said carbonyl group: The imine may be prepared by reacting the compound of formula (X) with an amine, suitably a primary alkyl amine such as n-butylamine. The reaction of the compound of formula (X) and the amine may be carried out in any suitable solvent, such as toluene, at any temperature providing a suitable rate of formation of the required product, generally at an elevated temperature such as the reflux temperature of the solvent; and preferably in the presence of a catalytic amount of toluenesulphonic acid.

The reaction between the compound of formula (X), and when it is in the form of an imine and nitroalkane may be carried out in glacial acetic acid, preferably in the presence of an ammonium acetate catalyst, generally at an elevated temperature such as in the range of from 60° C. to 120° C., for example 100° C.

A compound of formula (X) may be prepared from a compound of formula (XI):

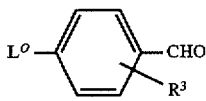

wherein $R^3$ is as defined in relation to formula (IX) and $L^o$ is a leaving group or atom, generally a fluorine atom, with an activated form of a compound of formula (XII):

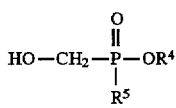

wherein $R^4$ and $R^5$ are as defined in relation to formula (I).

A suitable activated form of a compound of formula (XII) is an ionic form, such as a salted form, for example an alkali metal salted form.

An activated form of a compound of formula (XII) may be prepared by use of the appropriate conventional procedure, for example a salted form may be prepared by treating the compound of formula (XII) with a base such as an alkali metal hydride, for example sodium hydride.

The reaction between the compounds of formulae (XI) and (XII) may be carried out in any suitable solvent, generally an aprotic solvent such as dimethylformamide or N-methylpyrrolidinone at a low to ambient temperature, for example in the range of from −15° C. to 20° C., such as 5° C.

Compounds of formula (III) wherein $R^2$ together with $R^3$ represent a moiety of above defined formula (c), or an ester or amide thereof, are prepared from a protected form of a sub-set of the compounds of formula (III) of formula (XIII):

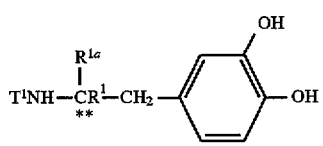

wherein $R^1$ and $R^{1a}$ are as defined in relation to formula (I) and $T^1$ represents a protecting group, such as a t-butoxycarbonyl group, by reaction with a compound of formula (XIV):

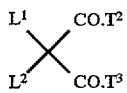

wherein $L^1$ and $L^2$ each represents a leaving group or atom, suitably a halogen atom such as bromine atom, and $T^2$ and $T^3$ each represents a protecting group; and thereafter if required removing any protecting group.

Suitably $T^2$ and $T^3$ each represent a $C_{1-6}$ alkoxy group, for example an ethoxy group.

Preferably, the compound of formula (XIII) is in an activated form.

A suitable activated form of a compound of formula (XIII) is an ionic form, such as an alkali metal salted form, for example a potassium salted form.

An activated form of a compound of formula (XIII) may be prepared by use of the appropriate conventional procedure, for example a salted form may be prepared by treating the compound of formula (XIII) with a base such as an alkali carbonate, for example potassium carbonate.

In the above mentioned reactions the compound of formula (XIII) is usually in an activated form, such as an anionic form. The activated form is conveniently prepared in-situ prior to addition of the compound of formula (XIV).

The reaction between the compounds of formula (XIII) and (XIV) may be carried out in an aprotic solvent, such as acetone, at any temperature which provides a suitable rate of formation of the required product but usually at an elevated temperature, such as the reflux temperature of the solvent, preferably in the presence of a base such as potassium carbonate and preferably under an inert atmosphere such as argon.

The compounds of formula (XIII) are known compounds or they are prepared according to methods used to prepare known compounds, such as those disclosed in J. Med. Chem. 1973, 16(5), 480.

The compounds of formula (XIV) are known commercially available compounds.

Compounds of formula (III), wherein $R^2$ is $OCH_2CO_2H$ or an ester or amide thereof or a moiety of the above defined formula (b) and $R^3$ is hydrogen, halogen, alkyl or alkoxy are conveniently prepared from a protected form of a sub-set of the compounds of formula (III) of formula (XV):

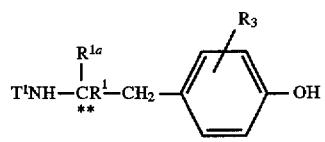

wherein $R^1$, $R^{1a}$, $R^3$ and $T^1$ are as defined in relation to formula (XIII):

a) for compounds of formula (III) wherein $R^2$ is $OCH_2CO_2H$ or an ester or amide thereof, by reaction with a compound of formula (XVI):

wherein $L^3$ is a leaving group or atom, suitably a halogen atom such as a bromine atom, and $T^4$ is a protecting group; or b) for compounds of formula (III) wherein $R^2$ is a moiety of the above defined formula (b), by reaction with a compound of formula (XVII):

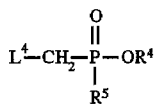

wherein $R^4$ and $R^5$ are as defined in relation to formula (I) and $L^4$ is a leaving group or atom; and thereafter, as necessary removing any protecting group.

Suitably, $T^1$ is a t-butoxycarbonyl group.

Suitably, $T^4$ is a $C_{1-6}$ alkoxy group such as a methoxy group.

Suitably, $L^4$ represents a tosylate group, a 4-chlorobenzenesulphonyloxy group or a 3-nitrobenzenesulphonyloxy group.

In the above mentioned reactions the compound of formula (XV) is usually in an activated form, such as an anionic form. The activated form is conveniently prepared in-situ prior to addition of the compound of formula (XVI) or (XVII).

Preferably, the activated form of the compound of formula (XV) is prepared by reaction of the compound of formula (XV) with a base such as sodium hydride.

The reaction between the compounds of formulae (XV) and (XVI) is suitably carried out in an aprotic solvent, such as acetone, at any temperature which provides a suitable rate of formulation of the required product usually an elevated temperature such as the reflux temperature of the solvent, preferably in the presence of a base such as potassium carbonate and preferably under an inert atmosphere such as argon.

The reaction between compounds of formulae (XV) and (XVII) is carried out in an aprotic solvent, such as dimethylformamide or dimethylsulphoxide at any temperature which provides a suitable rate of reaction, conveniently at ambient temperature.

The compounds of formula (XV) wherein $R^1$ and $R^{1a}$ each represent hydrogen are known compounds of are prepared according to methods used to prepare known compounds, such as those disclosed for such compounds when $T^1$ is t-butoxycarbonyl in Can. J. Chem. 1985, 63, 153.

The compounds of formula (XV) wherein either $R^1$ or $R^{1a}$ is hydrogen are prepared by hydrogenolysis of a compound of formula (XIX):

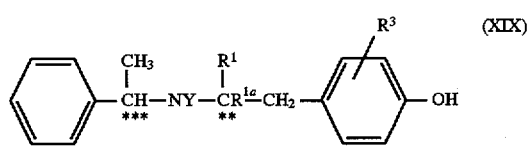

wherein $R^1$, $R^3$, Y and the CH and *CH carbon atoms are as defined in relation to formula (VI).

The hydrogenolysis of compounds of formula (XIX) is carried out under analogous conditions to the hydrogenolysis of the compounds of formula (VI).

The compounds of formula (XIX) wherein Y is a moiety —B(OH)$_2$ are prepared from compounds of formula (XIX) wherein Y is the H, using analogous methods to those described above for compounds of formula (VI) wherein Y is a moiety —B(OH)$_2$.

The compounds of formula (XIX) wherein Y is H are known compounds or they are prepared using analogous methods to those used to prepare known compounds for example those disclosed in J. Med. Chem. 1973, 16(5), 480.

A compound of formula (XVII) may be prepared by hydroxymethylation of a compound of formula (XX):

wherein $R^4$ and $R^5$ are as defined in relation to the compounds of formula (I), to provide a compound of the above defined formula (XII); and thereafter reacting the compound so formed with a source of leaving group $L^4$.

The hydroxymethylation is carried out using formaldehyde, generally in the form of paraldehyde, using conventional procedures depending upon the exact nature of the substrate, such as those disclosed by Houben-Weyl in Phosphor Verbinungen p28, J Amer Chem.-Soc. 1955, 77, 3522, Phosphorus and Sulphur 1978, 5, 455 or in Aust. J. Chem. 1979, 32, 463.

The conditions of reaction of the hydroxymethylated compound of formula (XII) with the source of the leaving group will depend upon the nature of the leaving group $L^4$ but the appropriate conventional conditions are employed. For example when $L^4$ represents a 4-chlorobenzenesulphonyloxy group the literature method of J. Cornforth et al (J.C.S. Perkin I, 1994, 1897) may be employed.

A compound of formula (I), wherein $R^{1a}$ represents hydrogen, or a pharmaceutically acceptable salt, ester or amide thereof or a pharmaceutically acceptable solvate thereof, may also be prepared by reducing a compound of formula (XXI):

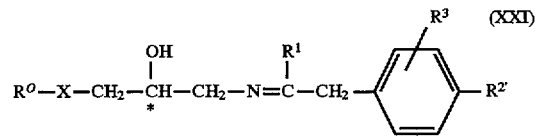

wherein $R^o$, $R^1$, $R^3$ and X are as defined in relation to formula (I) and $R^{2'}$ represents $R^2$ as defined in relation to formula (I) or a protected form thereof; and thereafter, if necessary, carrying out one or more of the following optional steps:

(i) converting one compound of formula (I) to another compound of formula (I);

(ii) removing any protecting group; and (iii) preparing a pharmaceutically acceptable salt, ester or amide thereof of a compound of formula (I) or a pharmaceutically acceptable solvate thereof.

The reduction of the compound of formula (XXI) may be carried out using any suitable reduction procedure, for example by using catalytic reduction.

Suitable catalysts include platinum oxide or 10% palladium on charcoal.

Suitable reduction conditions include using an alkanolic solvent such as methanol, at any temperature providing a convenient rate of formation of the required product, for example when using the platinum catalyst the reaction may conveniently be carried out at ambient temperature or when using the palladium catalyst the reaction may be carried out at a medium temperature such as 50° C., under a pressure of 1–5 atmospheres of hydrogen.

For compounds of formula (I) wherein $R^2$ represents a moiety of the above defined formula (b), $R^{2'}$ generally represents a protected form of $R^2$, for example a benzylated form, which may be removed by use of any conventional method, thus the benzylated form may be removed by use of hydrogenolysis using ammonium formate in the presence of a 10% palladium on carbon catalyst.

The compound of formula (XXI) may be prepared by reacting a compound of formula (XXII):

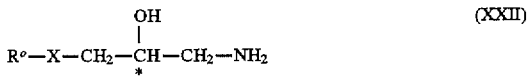

wherein $R^{o'}$ and X are as defined in relation to formula (II) with a compound of the above defined formula (VIII).

The reaction between compounds of formulae (VIII) and (XXII) may be carried out under conventional amination conditions, for example in a solvent such as toluene or, preferably, methanol.

Conveniently, the compound of formula (XXI) is prepared in-situ by reacting compounds of the above defined formulae (VIII) and (XXII) under reductive amination conditions which includes reaction in an alkanolic solvent, such as methanol, in the presence of a suitable reduction catalyst, for example those described above for the reduction of the compound of formula (XXI).

In a further aspect of the present invention there is provided a process for preparing a compound of formula (I) or a pharmaceutically acceptable salt thereof, or a pharmaceutically acceptable solvate thereof, which process comprises reacting a compound of formula (XXIII):

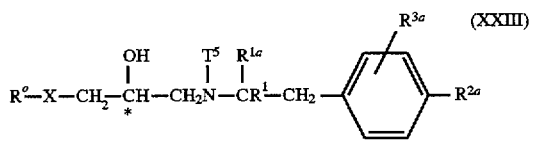

wherein $R^1$, $R^{1a}$ and X are as defined in relation to formula (I), $R^{o'}$ is as defined in relation to formula (II), $T^5$ is a protecting group, $R^{2a}$ represent $R^2$ or a group or atom convertible into $R^2$ and $R^{3a}$ represents $R^3$ or a group or atom convertible into $R^3$, wherein $R^2$ and $R^3$ are each as defined in relation to formula (I), with a reagent capable of converting $R^{2a}$ into $R^2$ and/or a reagent capable of converting $R^{3a}$ into $R^3$; and thereafter, if required, carrying out one or more of the following optional steps:

(i) converting a compound of formula (I) to a further compound of formula (I);

(ii) removing any protecting group;

(iii) preparing a pharmaceutically acceptable salt of the compound of formula (I) and/or a pharmaceutically acceptable solvate thereof.

Suitably, when $R^3$ in the required compound of formula (I) is hydrogen, halogen, alkyl or alkoxy $R^{3a}$ is $R^3$.

Suitably, when $R^3$ together with $R^2$ in the required compound of formula (I) represents a moiety of the above defined formula (c), or an ester or amide thereof, then $R^{2a}$ and $R^{3a}$ each represent OH.

Suitably, when $R^{2a}$ and $R^{3a}$ each represent OH they may be converted into a moiety of formula (c) by treating the compound of formula (XXIII) with a compound of the above defined formula (XIV) and thereafter as required forming an ester or amide of the resulting compound of formula (I).

The reaction conditions for the reaction between compounds of formulae (XXIII) and (XIV) are analogous to those for the reaction between compounds of formulae (XIII) and (XIV).

When $R^2$ in the required compound of formula (I) represents $OCH_2CO_2H$ or an ester or amide thereof, then $R^{2a}$ is suitably an OH group.

When $R^{2a}$ is OH, then a compound of formula (I) wherein $R^2$ represents $OCH_2CO_2H$ or an ester or amide thereof, may be prepared by reacting a compound of formula (XXIII) with a compound of the above defined formula (XVI).

The reaction conditions for the reaction between the compounds of formulae (XXIII) and (XVI) are analogous to those for the reaction between the compounds of formulae (XV) and (XVI).

When $R^2$ in the required compound of formula (I) represents a moiety of the above mentioned formula (b), then $R^{2a}$ is suitably an OH group.

When $R^2$ is OH, then a compound of formula (I) wherein $R^2$ represents a moiety of formula (b) may be prepared by reacting a compound of formula (XXIII) with a compound of the above defined formula (XVII).

The reaction conditions for the reaction between the compounds of formulae (XXIII) and (XVII) are analogous to those for the reaction between the compounds of formulae (XV) and (XVII).

The compounds of formula (XXII) are known compounds or they may be prepared according to methods used to prepare known compounds, for example those methods disclosed in Swiss Patent number 1549945 (1976).

The compounds of formula (XXIII) are prepared according to conventional procedures depending upon the value of $R^{2a}$ and $R^{3a}$. For example, when $R^{2a}$ and $R^{3a}$ each represents OH or when $R^{2a}$ is OH and $R^{3a}$ is hydrogen, halogen, alkyl or alkoxy then they may be prepared by reaction of a compound of above defined formula (II) with a compound of above defined formula (XIII) or (XV) as appropriate using conditions analogous to those used in the reaction between compounds of formulae (II) and (III).

Compounds of formula (III) including those of formula (XIII) or (XV) wherein $R^1$ and $R^{1a}$ each independently represent alkyl are known compounds or they may be prepared according to processes used to prepare known compounds, such as those disclosed by B. Renger in Arch. Pharm. (Weinheim)., 1983, 316(3), 193–201.

The compounds of formula (IV) are either known commercially available compounds or they are prepared according to published methods or by use of analogous methods to the published methods, for example those disclosed J.C.S. Perkin I; 1974, 1353.

The compounds of formula (V) are known commercially available compounds.

The compounds of formula (XII) are known compounds or they may be prepared by processes analogous to those used to prepare known compounds, for example the compounds of formula (XII) may be prepared according to methods disclosed in Phosphorus and Sulphur, 1978, 5, 455.

Suitable conversions of one compound of formula (I) into another compound of formula (I) include converting one group $OR^4$ into another group $OR^4$ and/or converting one group $R^5$ into another group $R^5$; or when $R^2$ is $OCH_2CO_2H$ or an ester or amide thereof, converting one $R^2$ into another $R^2$; or when $R^3$ together with $R^2$ represents a moiety of the above defined formula (a) or an ester or amide thereof, by converting one (a) into another (a).

Suitable conversions of one group $OR^4$ into another group $OR^4$ include:

(i) converting $OR^4$ as hydroxy into $OR^4$ as alkoxy;

(ii) converting $OR^4$ as alkoxy into $OR^4$ as hydroxy;

(iii) converting $OR^4$ as alkoxy into $OR^4$ as another alkoxy group.

The abovementioned conversion (i) may be carried out under conventional phosphonate alkylation methods, using for example the appropriate alcohol ($R^4OH$) in the presence of hydrogen chloride, alternatively, the appropriate alcohol may be used with benzotriazole-1-yloxy-tris-(dimethylamino)phosphonium hexafluorophosphate in dimethylformamide in the presence of diisopropylethylamine.

The abovementioned conversion (ii) may be carried out using conventional phosphonate hydrolysis methods, for example by treating the appropriate compound of formula (I) with an alkaline metal hydroxide, such as sodium hydroxide.

The abovementioned conversion (iii) may be carried out by first converting $OR^4$ as alkoxy into $OR^4$ as hydroxy using the conditions set out in respect of the abovementioned conversion (ii), followed by converting the hydroxy group so formed into another alkoxy group, using the conditions set out in respect of the abovementioned conversion (i).

The abovementioned conversion (iii) is of particular use for preparing compounds of formula (I) wherein $OR^4$ represents methoxy: such compounds are generally prepared from compounds of formula (I) wherein $OR^4$ represents an alkyloxy group other than methoxy (suitably ethoxy) by first hydrolysing the relevant $OR^4$ group (via conversion (ii)) to prepare a compound of formula (I) wherein $OR^4$ represents hydroxy and thereafter methylating (via conversion (i)) to provide the required compound wherein $OR^4$ represents methoxy.

Suitable conversions of one group $R^5$ into another group $R^5$, when $R^5$ represents hydroxy, alkoxy, arylalkyloxy, hydroxyalkyloxy, alkoxyalkyloxy, arylalkoxyalkyloxy or cycloalkyloxy, include analogous conversions to those mentioned above in regard to converting one group $OR^4$ into another group $OR^4$.

When $R^2$ is $OCH_2CO_2H$ or an ester or amide thereof, suitable conversions of one $R^2$ into another $R^2$ include converting $OCH_2CO_2R^e$ wherein $CO_2R^e$ is an ester, into $OCH_2CO_2H$, usually by conventional carboxylic acid hydrolysis, using for example basic hydrolysis with sodium hydroxide in an aprotic solvent such as 1,4-dioxan, at room temperature and preferably in an inert atmosphere such as argon. Other suitable conversions include interconverting the respective acids, esters and amides, such conversions being accomplished by the appropriate conventional procedure including those described herein.

When $R^3$ together with $R^2$ represents a moiety of the above defined formula (a) or an ester or amide thereof suitable conversions of one (a) into another (a) include hydrolysing esters to acids using an appropriate conventional procedure, such as treating the ester with lithium hydroxide in dioxan or methanol at ambient temperature, preferably in an inert atmosphere such as argon. Other suitable conversions include interconverting the respective acids, esters and amides using an appropriate conventional procedure including those described herein.

The protection of any reactive group or atom, may be carried out at any appropriate stage in the aforementioned processes. Suitable protecting groups include those used conventionally in the art for the particular group or atom being protected. Protecting groups may be prepared and removed using the appropriate conventional procedure, for example OH groups, including diols, may be protected as the silylated derivatives by treatment with an appropiate silylating agent such as di-tert-butylsilylbis(trifluoromethanesulfonate): The silyl group may then be removed using conventional procedures such as treatment with hydrogen fluoride, preferably in the form of a pyridine complex. Alternatively benzyloxy groups may be used to protect phenoxy groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in ethyl acetate or trifluoroacetic acid in methylene dichloride. The amino group also may be protected as an aminoboronic acid, prepared from the appropriate amine and boron tribromide followed by work up with iced water. The aminoboronic acid may be removed using catalytic hydrogenolysis, using for example a palladium on carbon catalyst. In addition, an amino group may be protected as a benzyl derivative, prepared from the appropriate amine and a benzyl halide under basic conditions, the benzyl group being removed by catalytic hydrogenolysis, using for example a palladium on carbon catalyst.

A leaving group or atom is any group or atom that will, under the reaction conditions, cleave from the starting material, thus promoting reaction at a specified site. Suitable examples of such groups unless otherwise specified are halogen atoms, mesyloxy groups and tosyloxy groups.

The salts, esters, amides and solvates of the compounds mentioned herein may be produced by methods conventional in the art: For example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR^sR^t$ may be prepared by treating the relevant carboxylic acid with an amine of formula $HNR^sR^t$, wherein $R^s$ and $R^t$ are as defined above. Alternatively, a $C_{1-6}$ alkyl ester such as a methyl ester of the acid may be treated with an amine of the above defined formula $HNR^sR^t$ to provide the required amide.

Compounds of formula (I) and pharmaceutically acceptable acid addition salts thereof; or a pharmaceutically acceptable solvate thereof, produced by the above processes, may be recovered by conventional methods.

If required mixtures of isomers of the compounds of the invention may be separated into individual stereoisomers and diastereoisomers by conventional means, for example by the use of an optically active acid as a resolving agent. Suitable optically active acids which maybe used as resolving agents are described in 'Topics in Stereochemistry', Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional X-ray crystallographic techniques.

As previously indicated, the compounds of formula (I) have been discovered to possess valuable pharmacological properties.

The present invention accordingly provides a compound of formula (I) or a pharmaceutically acceptable acid addition salt thereof, or a pharmaceutically acceptable solvate thereof, for use as an active therapeutic substance.

In one aspect, the present invention provides a compound of formula (I), or a pharmaceutically acceptable acid addition salt thereof, or a pharmaceutically acceptable solvate thereof, for use in the treatment of hyperglycaemia in human or non-human animals.

The present invention further provides a compound of formula (I), or pharmaceutically acceptable acid addition salt thereof, or a pharmaceutically acceptable solvate thereof, for use in the treatment of obesity in human or non-human animals.

In addition the present invention provides a compound of formula (I), or pharmaceutically acceptable acid addition salt thereof, or a pharmaceutically acceptable solvate thereof, for use in the treatment of gastrointestinal disorders such as peptic ulceration, oesophagitis, gastritis and duodenitis, intestinal ulcerations, including inflammatory bowel disease, and irritable bowel syndrome and also for the treatment of gastrointestinal ulcerations, especially when induced by non-steroidal anti-inflammatory drugs or corticosteroids.

Finally, the present invention provides a compound of formula (I), or pharmaceutically acceptable acid addition salt thereof, or a pharmaceutically acceptable solvate thereof, for use in increasing the high-density-lipoprotein (HDL) cholesterol concentration and decreasing the triglyceride concentration in human blood serum, in particular in the treatment and/or prophylaxis of atherosclerosis, and in the treatment of hyperinsulinaemia or depression.

A compound of formula (I), or a pharmaceutically acceptable acid addition salt thereof, or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of formula (I), or a pharmaceutically acceptable acid addition salt thereof, or a pharmaceutically acceptable solvate thereof, and a pharmaceutically acceptable carrier therefor.

As used herein the term "pharmaceutically acceptable" embraces compounds, compositions and ingredients for both human and veterinary use: for example the term "pharmaceutically acceptable salt" embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection, are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit dose will normally contain an amount of the active ingredient in the range of from 0.1 to 1000 mg, more usually 2–100 mg or 0.1 to 500 mg, and more especially 0.1 to 250 mg.

The present invention further provides a method for treating hyperglycaemia in a human or non-human mammal, which comprises administering an effective, non-toxic, amount of a compound of formula (I), or a pharmaceutically acceptable acid addition salt thereof, or a pharmaceutically acceptable solvate thereof, to a hyperglycaemic human or non-human mammal in need thereof.

The present invention further provides a method for treating obesity or for the treatment and/or prophylaxis of atherosclerosis in a human or non-human mammal, which comprises administering an effective, non-toxic, amount of a compound of formula (I), or a pharmaceutically acceptable acid addition salt thereof, or a pharmaceutically acceptable solvate thereof, to a human or non-human mammal in need thereof.

The present invention further provides a method for treating gastrointestinal disorders such as peptic ulceration, oesophagitis, gastritis and duodenitis, intestinal ulcerations, including inflammatory bowel disease, and irritable bowel syndrome and also for the treatment of gastrointestinal ulcerations, especially when induced by non-steroidal anti-inflammatory drugs or corticosteroids, in a human or non-human mammal, which comprises administering an effective, non-toxic, amount of a compound of formula (I), or a pharmaceutically acceptable acid addition salt thereof, or a pharmaceutically acceptable solvate thereof, to a human or non-human mammal in need thereof.

In addition the present invention provides a method for treating for increasing the high-density-lipoprotein (HDL) cholesterol concentration and decreasing the triglyceride concentration in human blood serum, in particular in the treatment and/or prophylaxis of atherosclerosis, and in the treatment of hyperinsulinaemia or depression, in a human or non-human mammal, which comprises administering an effective, non-toxic, amount of a compound of formula (I), or a pharmaceutically acceptable acid addition salt thereof, or a pharmaceutically acceptable solvate thereof, to a human or non-human mammal in need thereof.

The present invention also provides the use of a compound of formula (I), or a pharmaceutically acceptable acid addition salt thereof, or a pharmaceutically acceptable solvate thereof, for the manufacture of a medicament for the treatment of: hyperglycaemia, obesity, gastrointestinal disorders such as peptic ulceration, oesophagitis, gastritis and duodenitis, intestinal ulcerations, including inflammatory bowel disease, and irritable bowel syndrome and also for the treatment of gastrointestinal ulcerations, especially when induced by non-steroidal anti-inflammatory drugs or corticosteroids, for increasing the high-density-lipoprotein (HDL) cholesterol concentration and decreasing the triglyceride concentration in human blood serum, in particular in the treatment and/or prophylaxis of atherosclerosis, and in the treatment of hyperinsulinaemia or depression.

Conveniently, the active ingredient may be administered as a pharmaceutical composition hereinbefore defined, and this forms a particular aspect of the present invention.

In treating hyperglycaemic or obese humans the compound of formula (I), or a pharmaceutically acceptable salt, ester or amide thereof; or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

The treatment regimens for treating the abovementioned gastrointestinal disorders atherosclerosis, hyperinsulinaemia and depression are generally as described for hyperglycaemia.

In treating non-human mammals, especially dogs, the active ingredient may be administered by mouth, usually once or twice a day and in an amount in the range of from about 0.025 mg/kg to 25 mg/kg, for example 0.1 mg/kg to 20 mg/kg.

In a further aspect the present invention also provides a method for increasing weight gain and/or improving the feed utilisation efficiency and/or increasing lean body mass and/or decreasing birth mortality rate and increasing post/natal survival rate; of livestock, which method comprises the administration to livestock of an effective non-toxic amount of a compound of formula (I) or a veterinarily acceptable acid addition salt thereof, or a veterinarily acceptable solvate thereof.

Whilst the compounds of formula (I) and the veterinarily acceptable acid addition salts thereof or a veterinarily acceptable solvate thereof, may be administered to any livestock in the abovementioned method, they are particularly suitable for increasing weight gain and/or feed utilisation efficiency and/or lean body mass and/or decreasing birth mortality rate and increasing post-natal survival rate; in poultry, especially turkeys and chickens, cattle, pigs and sheep.

In the preceding method the compounds of formula (I) or veterinarily acceptable acid addition salts thereof will normally be administered orally although non-oral modes of administration, for example injection or implantation, are also envisaged. Suitably the compounds are administered in the feed-stuff or drinking water provided for the livestock. Conveniently these are administered in the feed-stuff at from $10^{-3}$ ppm–500 ppm of total daily fed intake, more usually 0.01 ppm to 250 ppm, suitably less than 100 ppm.

The particular formulations used will of course depend upon the mode of administration but will be those used conventionally in the mode of administration chosen. For administration in feed-stuff the drugs are conveniently formulated as a premix in association with a suitable carrier.

Accordingly, the present invention also provides a veterinarily acceptable premix formulation comprising a compound of formula (I), or a veterinarily acceptable acid addition salt thereof; or a veterinarily acceptable solvate thereof, in association with a veterinarily acceptable carrier therefore.

Suitable carriers are inert conventional agents such as powdered starch. Other conventional feed-stuff premix carriers may also be employed.

No unacceptable toxicological effects are expected when compounds of the invention are administered in accordance with the present invention.

The following Examples and Procedures illustrate the invention but do not limit it in any way.

Procedure 1:

(S)-Glycidyl-2-benzyloxyphenol

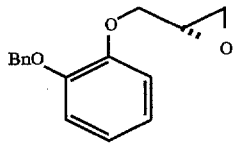

A mixture of 2-benzyloxyphenol (900 mg, 4.5 mMol) and potassium carbonate (1.87 g, 13.5 mMol) in acetone (45 ml) was heated under reflux for 15 mins. (S)-Glycidyl-3-nitrobenzenesulphonate (1.0 g, 4.5 mMol) was added and the reaction mixture was heated under reflux for 23 hours. After cooling, the reaction mixture was filtered and the solvent was evaporated. The residue was partitioned between ethyl acetate and water. The organic fractions were combined, washed with water and brine, dried and evaporated to give the title compound as an oil.

$\delta^1$H (270 MHz, CDCl$_3$): 7.36 (5H, m), 6.88 (4H, m), 5.10 (2H, s), 4.26 (1H, dd, J=11.4, 3.3 Hz), 4.20 (1H, dd, J=11.4, 5.5 Hz), 3.36 (1H, m), 2.85 (1H, dd, J=5.0, 4.1 Hz), and 2.73 (1H, dd, J=5.0, 2.5 Hz) ppm.

Procedure 2:

(S,R)-Methyl-4-[2-[2-hydroxy-3-(2-benzyloxyphenoxy)propylamino]propyl]
phenoxyacetate

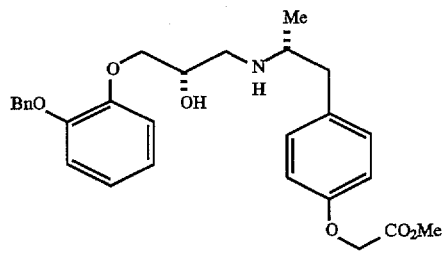

A mixture of (S)-glycidyl-2-benzyloxyphenol (666 mg, 2.59 mMol) and (R)-methyl-4-(2-aminopropyl)phenoxyacetate (501 mg, 2.25 mMol) in MeOH (15 ml) was heated under reflux under argon for 24 hours. After cooling, the solvent was evaporated and the residue was partitioned between dichloromethane and water. The organic layer was washed with water and brine, dried and evaporated. The residue was purified by column chromatography eluting with 0–10% methanol in dichloromethane giving the title compound as an oil.

$\delta^1$H (270 MHz, CDCl$_3$): 7.5–7.25 (5H, m), 7.05 (2H, d, J=8.6 Hz), 6.92 (4H, m), 6.79 (2H, d, J=8.6 Hz), 5.08 (2H, s), 4.59 (2H, s), 4.2–4.0 (3H, m), 3.80 (3H, s), 3.0–2.4 (5H, m) and 1.04 (3H, d, J=6.3 Hz) ppm.

Procedure 3:

(S,R)-Methyl-4-[2-[2-hydroxy-3-(2-hydroxyphenoxy)propylamino]propyl]
phenoxyacetate

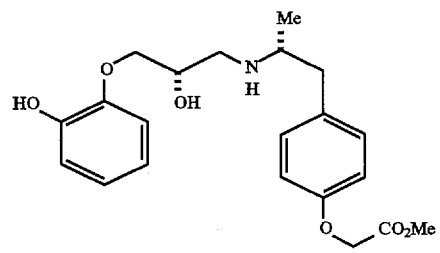

(S,R)-Methyl-4-[2-[2-hydroxy-3-(2-benzyloxyphenoxy)propylamino]propyl]phenoxyacetate (270 mg, 0.56 mMol) was dissolved in methanol (40 ml), palladium on charcoal (5%, 40 mg) was added and the mixture was hydrogenated at room temperature and pressure for 18 hours. The suspension was filtered through a pad of filter aid, the filter pad was washed with methanol and the combined filtrates were evaporated giving a dark residue. Purification by column chromatography eluting with 0–10 % methanol in dichloromethane gave the title compound as an oil.

$\delta^1$H (270 MHz, CDCl$_3$): 7.08 (2H, d, J=8.8 Hz), 6.79 (6H, m), 4.61 (2H, s), 4.1–3.9 (3H, m), 3.80 (3H, s), 3.0–2.7 (5H, m) and 1.12 (3H, d, J6.1 Hz) ppm.

Procedure 4:

(S)-Glycidyl-3-benzyloxyphenol

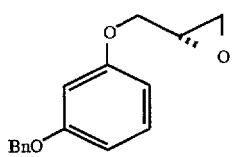

A mixture of 3-benzyloxyphenol (900 mg, 4.5 mMol) and potassium carbonate (1.87 g, 13.5 mMol) in acetone (45 ml) was heated under reflux for 15 mins. (S)-Glycidyl-3-nitrobenzenesulphonate (1.0 g, 4.5 mMol) was added and the reaction mixture was heated under reflux for 23 hours. After cooling the reaction mixture was filtered and the solvent was evaporated. The residue was partitioned between ethyl acetate and water. The organic fractions were combined, washed with water and brine, dried and evaporated to give the title compound as an oil.

$\delta^1$H (270 MHz, CDCl$_3$): 7.25 (5H, m), 7.15 (1H, m), 6.50 (3H, m), 5.14 (2H, s), 4.10 (1H, dd, J=11.0, 3.3 Hz), 3.80 (1H, dd, J=11.0, 5.8 Hz), 3.40 (1H, m), 2.80 (1H,dd, J=5.0, 4.1 Hz) and 2.70 (1H, dd, J=5.0, 2.5 Hz) ppm.

Procedure 5:

(S,R)-Methyl-4-[2-[2-hydroxy-3-(3-benzyloxyphenoxy)propylamino]propyl]phenoxyacetate

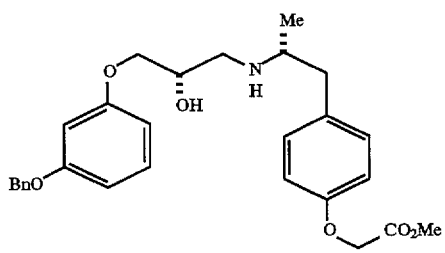

A mixture of (S)-glycidyl-3-benzyloxyphenol (580 mg, 2.27 mMol) and (R)-methyl-4-(2-aminopropyl)phenoxyacetate (640 mg, 2.87 mMol) in MeOH (15 ml) was heated under reflux under argon for 24 hours. After cooling, the solvent was evaporated and the residue was partitioned between dichloromethane and water. The organic layer was washed with water and brine, dried and evaporated. The residue was purified by column chromatography eluting with 0–20% methanol in dichloromethane giving the title compound as an oil.

$\delta^1$H (270 MHz, CDCl$_3$): 7.5–7.08 (8H, m), 6.83 (2H, d, J=8.5 Hz), 6.7–6.5 (3H, m), 5.03 (2H, s), 4.60 (2H, s), 3.90 (3H, m), 3.80 (3H, s), 2.9–2.5 (5H, m) and 1.06 (3H, d, J=6.3 Hz) ppm.

Procedure 6:

(S,R)-Methyl-4-[2-[2-hydroxy-3-(3-hydroxyphenoxy)propylamino]propyl] phenoxyacetate

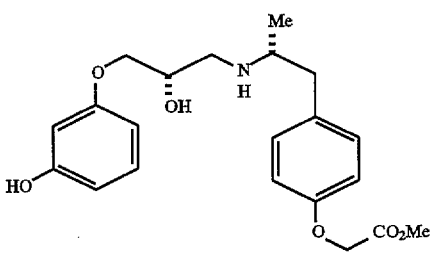

(S,R)-Methyl-4-[2-[2-hydroxy-3-(3-benzyloxyphenoxy) propylamino]propyl]phenoxyacetate (540 mg, 1.13 mMol) was dissolved in methanol (50 ml), palladium on charcoal (5%, 75 mg) was added and the mixture was hydrogenated at room temperature and pressure for 24 hours. The suspension was filtered through a pad of filter aid, the filter pad was washed with methanol and the combined filtrates were evaporated giving a dark residue. Purification by column chromatography eluting with 0–20 % methanol in dichloromethane gave the title compound as an oil.

$\delta^1$H (270 MHz, d$^6$-DMSO/D$_2$O): 7.2–7.0 (3H, m), 6.79 (2H, d, J=8.8 Hz), 6.4–6.3 (3H, m), 4.73 (2H, s), 3.95–3.75 (3H, m), 3.69 (3H, s), 2.9–2.6 (4H, m), 2.45–2.35 (1H, m) and 0.92 (3H, d, J=6.0 Hz) ppm.

Procedure 7:

(S)-Glycidyl-4-benzyloxyphenol

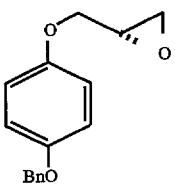

A mixture of 4-benzyloxyphenol (2.0 g, 10 mMol) and potassium carbonate (4.14 g, 30 mMol) in acetone (50 ml) was heated under reflux for 15 mins. (S)-Glycidyl-3-nitrobenzenesulphonate (2.23 g, 10 mMol) was added and the reaction mixture was heated under reflux for 18 hours. After cooling, the reaction mixture was filtered and the solvent was evaporated. The residue was partitioned between ethyl acetate and water. The organic fractions were combined, washed with water and brine, dried and evaporated to give the title compound as an oil.

$\delta^1$H (270 MHz, CDCl$_3$): 7.35 (5H, m), 6.87 (4H, m), 5.01 (2H, s), 4.16 (1H, dd, J=11.0, 3.3 Hz), 3.91 (1H, dd, J=11.0, 5.8 Hz), 3.34 (1H, m), 2.89 (1H, dd, J=5.0, 4.1 Hz) and 2.74 (1H, dd, J=5.0, 2.8 Hz) ppm.

Procedure 8:

(S,R)-Methyl-4-[2-[2-hydroxy-3-(4-benzyloxyphenoxy)propylamino]propyl]phenoxyacetate

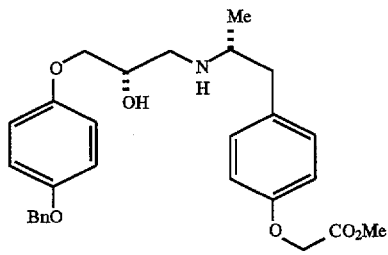

A mixture of (S)-glycidyl-4-benzyloxyphenol (330 mg, 1.29 mMol) and (R)-methyl-4-(2-aminopropyl) phenoxyacetate (380 mg, 1.47 mMol) in MeOH (15 ml) was heated under reflux under argon for 24 hours. After cooling, the solvent was evaporated and the residue was partitioned between dichloromethane and water. The organic layer was washed with water and brine, dried and evaporated. The residue was purified by column chromatography eluting with 0–15% methanol in dichloromethane giving the title compound as an oil.

$\delta^1$H (270 MHz, CDCl$_3$): 7.26(5H, m), 7.08 (2H, m), 6.80 (6H, m), 5.01 (2H, s), 4.61 (2H, s), 3.90 (3H, m), 3.80 (3H,s), 2.75 (5H, m) and 1.08 (3H, d, J=6.3 Hz) ppm.

Procedure 9:

(S,R)-Methyl-4-[2-[2-hydroxy-3-(4-hydroxyphenoxy)propylamino]propyl]phenoxyacetate

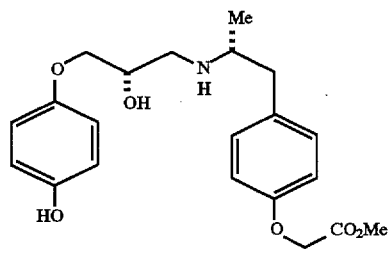

(S,R)-Methyl-4-[2-[2-hydroxy-3-(4-benzyloxyphenoxy)propylamino]propyl]phenoxyacetate (200 mg, 0.42 mMol) was dissolved in methanol (25 ml), palladium on charcoal (5%, 20 mg) was added and the mixture was hydrogenated at room temperature and pressure for 18 hours. The suspension was filtered through a pad of filter aid, the filter pad was washed with methanol and the combined filtrates were evaporated giving a dark residue. Purification by column chromatography eluting with 0–10% methanol in dichloromethane gave the title compound as an oil.

$\delta^1$H (270 MHz, d$^6$-DMSO/D$_2$O): 7.10 (2H, d, J=8.5 Hz), 6.80 (2H, d, J=8.5 Hz), 6.72 (2H, d, J=8.9 Hz), 6.65 (2H, d, J=8.9 Hz), 4.73 (2H, s), 3.8–3.75 (3H, m), 3.70 (3H, s), 2.9–2.4 (5H, m) and 0.90 (3H, d, J=6.1 Hz) ppm.

Procedure 10:

2,2-Di-tert-butyl-4H-1,3,2-benzodioxasilin-6-ol

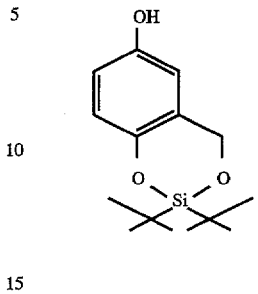

A mixture of 2,2-di-tert-butyl-6-(benzyloxy)-4H-1,3,2-benzodioxasilinane (2 g, 5.41 mMol) and 10% palladium on charcoal (50 mg) in dichloromethane (20 ml) was hydrogenated at atmospheric pressure. After 6 hours the reaction mixture was filtered through a short pad of celite and the solvent evaporated to yield a clear oil.

$\delta^1$H (250 MHz, CDCl$_3$): 6.80 (1H, d, J=8); 6.67 (1H, dd, J=8.1 Hz and 2.4 Hz); 6.45 (1H, d, J=2.4 Hz); 4.90 (2H, s); 1.14 (18H, s).

Procedure 11:

2,2-Di-tert-butyl-6-(benzyloxy)-4H-1,3,2-benzodioxasilinane

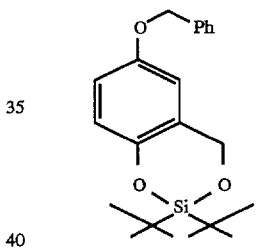

Lithium aluminium hydride (0.235 g, 6.2 mMol) was suspended in tetrahydrofuran (25 ml) and cooled to 0° C. 5-Benzyloxy-2-hydroxy benzoic acid methyl ester (2 g, 7.75 mMol) in tetrahydrofuran (10 ml) was added dropwise, via cannula. The mixture was warmed to room temperature and stirred for 20 minutes. The reaction was then cooled to 0° C. and cautiously quenched by the addition of water (0.5 ml), 2M sodium hydroxide solution (0.5 ml), and water (1 ml). The resulting mixture was stirred at room temperature for 30 minutes and filtered. The filtrate was evaporated in vacuo to yield 4-benzyloxy-2-hydroxymethyl phenol as a clear oil which was used in the next step without further purification.

To a solution of 4-benzyloxy-2-hydroxymethyl phenol in chloroform (10 ml) was added 2,6-lutidine (2.49 g, 23.25 mMol) at room temperature under argon. Di-tert-butylsily bis(trifluoromethanesulfonate) (4.1 g, 9.3 mMol) was added and the mixture stirred at room temperature for 18 hours. The solvent was evaporated in vacuo and the residue purified by normal phase column chromatography, eluting with 50% hexane in ether to give the title product as pale yellow oil.

$\delta^1$H (250 MHz, CDCl$_3$): 7.34–7.48 (5H, m); 6.85 (2H, m); 6.61 (1H, m), 5.0 (2H, s); 4.78 (2H, s); 1.14 (18H, s).

Procedure 12:

(S)-2,2-Di-tert-butyl-6-(oxiran-2-ylmethoxy)-4H-1,3,2-benzodioxasilinane

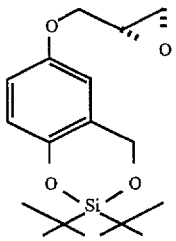

To a solution of 2,2-di-tert-butyl-4H-1,3,2-benzodioxasilin-6-ol (1.4 g, 5 mMol) in acetone (40 ml) at room temperature under argon was added potassium carbonate (2.07 g, 15 mMol). (2S)-(+)-glycidyl-3-nitrobenzenesulfonate (1.43 g 5.5 mMol) was added portionwise and the reaction mixture was heated at reflux for 48 hours. The solvent was removed under reduced pressure. The residue was taken into ethyl acetate and washed with water (2×15 ml). The organic extracts were dried ($Na_2SO_4$) and the solvent evaporated in vacuo. The crude product was purified by chromatography over normal phase silica eluting with 50% hexane in ether to give (S)-2,2-Di-tert-butyl-6-(oxiran-2-ylmethoxy)-4H-1,3,2-benzodioxasilinane.

$\delta^1H$ (250 MHz, $CDCl_3$): 6.75–6.90 (2H, m), 6.7 (1H, d, J=2.5 Hz); 4.97 (2H, s); 4.16 (1H, dd, J=11, 3 Hz); 3.88 (1H, dd, J=11, 5.7 Hz); 3.35 (1H, m); 2.89 (1H, dd, J=5.0, 4.1 Hz); 2.73 (1H, dd, J=5, 2.4 Hz); 1.14 (18H, s).

Procedure 13:

(SR)-4-{2-[3-(2,2-Di-tert-butyl-4H-1,3,2-benzodioxasilinan-6-yl-oxy)-2-hydroxy propylamine]propyl}phenoxymethyl phosphonic acid diethyl ester

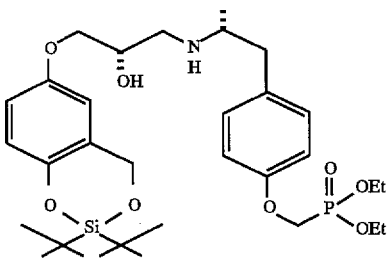

A mixture of (S)-2,2-di-tert-butyl-6-(oxiran-2-ylmethoxy)-4H-1,3,2-benzodioxasilinane (0.622 g, 1.85 mMol) and (R)-diethyl 4-(2-aminopropyl)phenoxymethyl phosphonate (0.55 g, 1.83 mMol) was dissolved in methanol (10 ml) and refluxed under a argon atmosphere for 20 hours. The methanol was evaporated and the residue taken up into dichloromethane (75 ml), washed with water (3×50 ml) and dried with anhydrous sodium sulfate. After evaporation of the solvent in vacuo, the crude product was purified by column chromatography over normal phase silica, eluting with 10% methanol in ethyl acetate to give the title compound as a dark oil.

$\delta^1H$ (250 MHZ, $CDCl_3$): 7.15 (2H, d, J=9.3 Hz); 6.09 (2H, d, J=9.0 Hz); 6.85 (1H, d, J=7.9 Hz); 6.72 (1H, dd, J=7.9 Hz and 2.7 Hz); 6.50 (1H, dd, J=2.6 Hz); 4.93 (2H, s); 4.25 (6H, m); 3.9 (3H, m); 2.5–2.9 (5H, m); 1.36 (6H, t, J=6.6 Hz); 1.07 (3H, d, J=6.8 Hz); 1.04 (18H, s)

Procedure 14:

(SR)-4-{2-[3-(2,2-Di-tert-butyl-4H-1,3,2-Benzodioxasilinan-6-yl-oxy)-2-hydroxypropylamine]propyl}phenoxymethyl carboxylic acid methyl ester

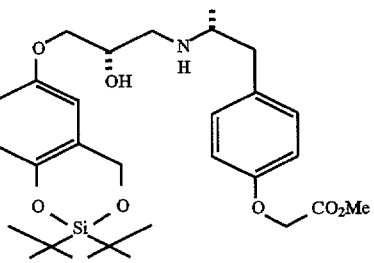

A solution of (S)-2,2-Di-tert-butyl-6-(oxiran-2-ylmethoxy)-4H-1,32,-benzodioxasilinane (0.65 g, 1.93 mMol) in acetonitrile (25 ml) was treated with lithium perchlorate (0.205 g, 1.93 mMol), then stirred until complete solution of the salt. To the resulting stirred solution was added (R)-methyl 4-(2-aminopropyl)phenoxymethyl carboxylic acid methyl ester (0.43 g, 1.93 mMol). The mixture was heated at 80° C. for 20 hours, then cooled, diluted with ethyl acetate and washed with water (2×50 ml). The dried ($Na_2SO_4$) extracts were concentrated in vacuo, and the crude product purified by column chromatography over normal phase silica, eluting with 5% methanol in ethyl acetate to give the title compound as an oil.

$\delta^1H$ (250 MHz, $CDCl_3$): 7.12 (2H, d, J=8.7 Hz); 6.87 (3H, m); 6.75 (1H, dd, J=8.8 Hz and 2.7 Hz); 6.53 (1H, d, J=2.6 Hz); 4.93 (2H, s); 4.60 (2H, s); 3.87 (3H, m); 3.81 (3H, s); 2.95–2.50 (5H, m); 1.07 (3H, d, J=6.7 Hz); 1.03 (18H, s)

Procedure 15:

3,4-Dibenzyloxyphenol

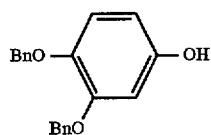

A solution of 3,4-dibenzyloxyacetophenone (5.18 g, 20 mMol) in acetic acid (25 ml), chloroform (8 ml), water (4 ml) and peracetic acid (36–40 wt % in acetic acid, 18 ml) was stirred at 40° C. for 4 hours. After cooling to room temperature, saturated sodium thiosulfate solution was added and the product was extracted into ethyl acetate. The organic extracts were separated, washed with saturated sodium bicarbonate solution, water and brine. The organic solution was dried and evaporated. A solution of the residue in methanol (25 ml) was treated with sodium hydroxide solution (2M, 8 ml) and the reaction was stirred at room temperature for 16 hours. The solvent was evaporated and the residue was dissolved in water (10 ml) and the pH of the solution was adjusted to 9 with 1M hydrochloric acid. The solvent was evaporated and the residue was partitioned between ethyl acetate and water. The organic extracts were separated, dried and evaporated giving the title compound as a colourless solid.

$\delta(CDCl_3)$: 7.25 (10H, m), 6.77 (1H, d, J=8.5 Hz), 6.48 (1H, d, J=2.8 Hz), 6.27 (1H, dd, J=8.5, 2.8 Hz), 5.10 (2H, s), 5.06 (2H, s), 4.65 (1H, br, exchanges with $D_2O$).

Procedure 16:

(S)-3-(3,4-Dibenzyloxyphenoxy)-1,2-epoxypropane

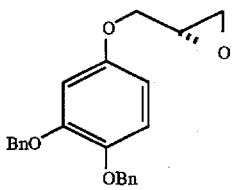

The title compound was prepared from 3,4-dibenzyloxphenol and (S)-glycidyl 3-nitrobenzene sulfonate according to the method described in Procedure 12.

δ(CDCl₃): 7.36 (10H, m), 6.85 (1H, d, J=8.8 Hz), 6.60 (1 H, d, J=2.9 Hz), 6.38 (1H, dd, J=8.8, 2.9 Hz), 5.13 (2H, s), 5.08 (2H, s), 4.14 (1H, dd, J=11, 3.3 Hz), 3.85 (1H, dd, J=11, 5.8 Hz), 3.31 (1H, m), 2.88 (1H, dd, J=4.9, 4.1 Hz), 2.71 (1H, dd, J=4.9, 2.6 Hz).

Procedure 17:

(SR)-4-{2-[3-(3,4-Dibenzyloxyphenoxy)-2-hydroxypropylamino]propyl}phenoxy acetic acid, methyl ester

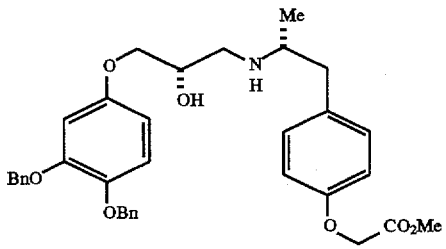

The title compound was prepared from (S)-3-(3,4-dibenzyloxyphenoxy)-1,2-epoxypropane and (R)-4-(2-aminopropyl)phenoxyacetic acid methyl ester according to the method described in Procedure 13.

δ(CDCl₃): 7.5–7.3 (10H, m), 7.09 (2H, d, J=8.8 Hz), 6.85–6.80 (3H, m), 6.58 (1H, d, J=3.0 Hz), 6.35 (1H, dd, J=8.8, 3.0 Hz), 5.12 (2H, s), 5.07 (2H, s), 4.60 (2H, s), 3.9–3.83 (3H, m), 3.80 (3H, s), 3.0–2.5 (5H, m), 1.06 (3H, d, J=6.3 Hz).

Procedure 18:

(R)-3-(3,4-Dihydroxyphenyl)-2-propylamine hydrobromide

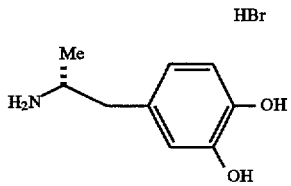

A solution of (R)-3-(3,4-dimethoxyphenyl)-2-propylamine hydrochloride[1] (500 mg, 2.15 mMol) in hydrogen bromide (48%, 5 ml) was stirred at 100° C. under an argon atmosphere for 20 hours. After cooling, the solvent was evaporated and the residue was dried giving the title compound.

[1] D. E. Nichols, C. F. Barfknecht and D. B. Rusterholz. J. Med. Chem., 1973, 16(5), 480.

δ(D⁶DMSO+D₂O): 6.9–6.4 (3H, m), 3.5–2.4 (3H, m), 1.3 (3H, d, J=7 Hz) ppm.

Procedure 19:

(R)-2-(3,4-Dihydroxyphenyl)propylcarbamic acid, t-butyl ester

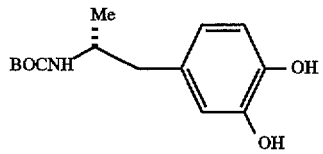

A solution of (R)-3-(3,4-dihydroxyphenyl)-2-propylamine hydrobromide (480 mg, 1.9 mMol) in dimethylformamide (5 ml) containing triethylamine (3 equiv, 586 mg, 5.7 mMol) was stirred at 5° C. under an argon atmosphere for 15 minutes. Di-t-butyl dicarbonate (414 mg, 1.9 mMol) was added and the reaction mixture was stirred at 5° C. for 1 hour and then at ambient temperature for 1 hour. The solvent was evaporated. Ethyl acetate (100 ml) and water (50 ml) were added and the organic layer was separated, washed with water (50 ml) and brine (50 ml), dried (MgSO₄) and evaporated. Purification of the residue by chromatography on silica gel eluting with 25% ethyl acetate in n-hexane gave the title compound, m.p. 116°–118° C.;

δ(CDCl₃): 6.76 (1H, d, J=7.9 Hz), 6.70 (1H, d, J=2 Hz), 6.55 (1H, dd, J=7.9, 2 Hz), 6.25–5.90 (2H, br, exchanges with D₂O), 4.45 (1H, br, exchanges with D₂O), 3.8 (1H, b), 2.75–2.5 (2H, m), 1.43 (9H, s), 1.07 (3H, d, J=6.6 Hz) ppm.

Procedure 20:

(R)-5-[N-(t-Butyloxycarbonyl)-2-aminopropyl]-1,3-benzodioxole-2,2-dicarboxylic acid, diethyl ester

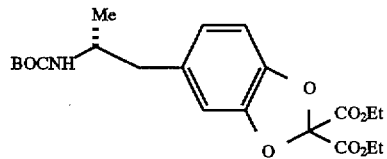

A solution of (R)-2-(3,4-dihydroxyphenyl)propylcarbamic acid, t-butyl ester. (1.07 g, 4 mMol) in acetone (25 ml) containing potassium carbonate (3 equiv, 1.66 g, 12 mMol) was stirred at 60° C. under an argon atmosphere for 1 hour. After cooling to ambient temperature, a solution of diethyl dibromomalonate (1.27 g, 4 mMol) in acetone (7 ml) was added and the reaction was stirred at ambient temperature for 18 hours. The suspension was filtered and the residue was washed with ethyl acetate. The filtrates were combined, evaporated and the residue was partitioned between ethyl acetate (200 ml) and dilute hydrochloric acid (100 ml, pH5). The organic layer was separated, washed with water (2×100 ml) and brine (100 ml), dried (MgSO₄) and evaporated. The residue was purified by column chromatography on silica gel eluting with 25% ethyl acetate in n-hexane giving the title compound as an oil;

δ(CDCl₃): 6.86 (1H, d, J=8 Hz), 6.78 (1H, d, J=1.3 Hz), 6.71 (1H, dd, J=8, 1.3 Hz), 4.41–4.32 (5H, m), 3.8 (1H, br, exchanges with D₂O),2.76 (1H, dd, J=13.5, 5.6 Hz), 2.60 (1H, dd, J=13.5, 7.2 Hz),1.43 (9H, s), 1.36–1.31 (6H, m), 1.07 (3H, d, J=6.6 Hz) ppm.

Procedure 21:

(R)-5-(2-Aminopropyl)-1,3-benzodioxole-2,2-dicarboxylic acid, diethyl ester, hydrochloride salt

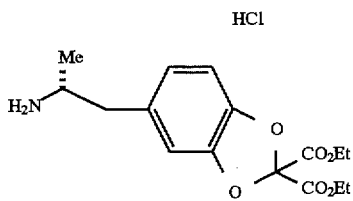

A solution of (R)-5-[N-(t-butyloxycarbonyl)-2-aminopropyl]-1,3-benzodioxole-2,2-dicarboxylic acid diethyl ester (3.0 g, 7 mMol) in ethyl acetate (40 ml) and hydrogen chloride solution in diethyl ether (1M, 56 ml, 56 mMol) was stirred at ambient temperature under an argon atmosphere for 48 hours. The solvent was evaporated and the residue was dried giving the title compound as a glass.

δ($d^6$-DMSO): 8.07 (3H, br, exchanges with $D_2O$), 7.10–7.06 (2H, m), 6.85 (1H, dd, J=8, 1.4 Hz), 4.33 (4H, q, J=7.1 Hz), 3.5–3.4 (1H, m), 2.93 (1H, dd, J=13.4, 5.8 Hz), 2.66 (1H, d, J=13.5, 8.2 Hz), 1.24 (6H, t, J=7.1 Hz), 1.12 (3H, d, J=6.3 Hz) ppm.

Procedure 22:

(R)-5-(2-Aminopropyl)-1,3-benzodioxole-2,2-dicarboxylic acid, diethyl ester

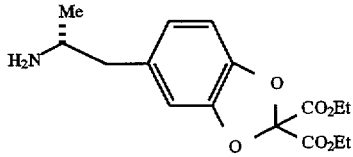

A solution of (R)-5-(2-aminopropyl)-1,3-benzodioxole-2,2-dicarboxylic acid diethyl ester hydrochloride (646 mg, 2 mMol) in dichloromethane (80 ml) was shaken with a saturated solution of sodium hydrogen carbonate (20 ml) for 30 seconds. The organic layer was separated and the aqueous layer was extracted with dichloromethane (2× 50 ml). The combined organic extracts were washed with water (50 ml) and brine (50 ml), dried ($MgSO_4$). The solvent was evaporated giving the title compound which was used immediately.

Procedure 23:

(SR)-5-{2-[3-(2,2-Di-t-butyl-4H-1,3,2-benzodioxasilinan-6-yloxy)-2-hydroxypropylamino]propyl}-1,3-benzodioxole-2,2-dicarboxylic acid, diethyl ester

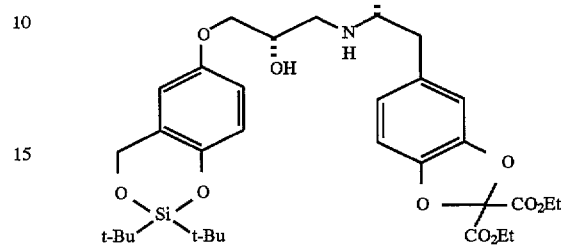

The title compound was prepared from (R)-5-(2-aminopropyl)-1,3-benzodioxole-2,2-dicarboxylic acid diethyl ester and (S)-2,2-di-t-butyl-6-(oxiran-2-ylmethoxy)-4H-1,3,2-benzodioxasilinane by heating in ethanol as solvent according to the method described in Procedure 13.

δ($CDCl_3$): 6.86–6.49 (6H, m), 4.94 (2H, s), 4.36 (4H, q, J=7.2 Hz), 4.1–3.8 (3H, m), 3.0–2.5 (5H, m), 1.34 (6H, t, J=7.2 Hz), 1.08 (3H, d, J=6.3 Hz), 1.03 (18H, s).

Procedure 24:

4-(2-t-Butoxycarbonylaminoethyl)phenoxymethyl phosphonic acid, diethyl ester

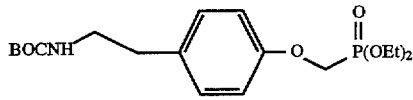

A solution of 2-(4-hydroxyphenyl)ethylcarbamic acid, t-butyl ester[1] (4.0 g, 16.9 mMol) in dry DMSO (37.5 ml) was cooled in an ice-bath and treated with sodium hydride (80% in mineral oil 0.557 g, 1.1 equiv) with stirring under argon according to the method described by Cornforth[2]. When effervescence ceased a solution of 4-chlorobenzenesulfonyloxymethylphosphonate diethyl ester (6.07 g, 1.05 equiv) in dry DMSO (110 ml) was added and the resulting pale yellow solution stirred at room temperature overnight. The mixture was then poured into water (550 ml) and extracted with diethyl ether/ethyl acetate (1:1, 3×150 ml) and finally ethyl acetate (3×100 ml). The combined extracts were washed with brine, dried over anhydrous sodium sulfate and evaporated to dryness. The resulting oil was purified by chromatography on silica gel with a gradient of 3:2 pentane:ethyl acetate rising to 100% ethyl acetate to give the title compound as a colourless viscous oil.

[1] F. Houlihan et. al. Can. J. Chem., 1985, 63, 153.
[2] J. Cornforth and J. R. H Wilson. J.C.S. Perkin I., 1994, 1897.

$δ^1H$(250 MHz, $CDCl_3$): 7.12 (2H, d), 6.90 (2H, d), 4.51 (1H, br s), 4.30–4.15 (6H, m), 3.33 (2H, br. q), 2.74 (2H, t), 1.43 (9H, s), 1.37 (6H, t).

Procedure 25:

4-(2-Aminoethyl)phenoxymethylphosphonic acid, diethyl ester

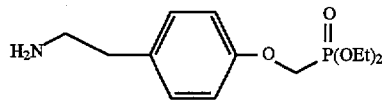

4-(2-t-Butoxycarbonylaminoethyl) phenoxymethylphosphonic acid, diethyl ester (2.856 g, 9.95 mMol) in methylene chloride (300 ml) and trifluoroacetic acid (16 ml) was stirred at room temperature for 5 h. The solution was concentrated under reduced pressure and product dried under in vacuo. The trifluoacetic acid salt was neutralized with aqueous sodium carbonate and extracted with dichloromethane containing a small proportion of methanol (5×100 ml). The combined organic layers were dried over sodium sulfate and evaporated to dryness to give the title compound as a pale yellow gum.

$\delta^1$H (250 MHz, CDCl$_3$): 7.12 (2H, d), 6.9 (2H, d), 4.30–4.15 (6H, m), 3.00–2.55 (4H, m) and 1.37 (6H, t).

Procedure 26:

(S)-4-{2-[3-(2,2-Di-t-butyl-4H-1,3,2-benzodioxasilinan-6-yl-oxy)-2-hydroxypropylamino]ethyl}phenoxymethyl phosphonic acid, diethyl ester

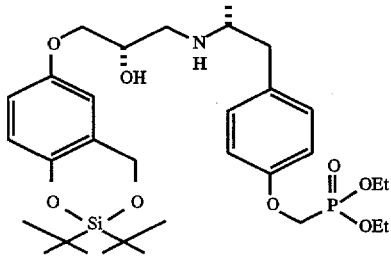

Using similar a experimental method to that of Procedure 13, the title compound was obtained from 4-(2-aminoethyl)phenoxymethylphosphonic acid diethyl ester and (S)-2,2-di-t-butyl-6-(oxiran-2-ylmethoxy)-4H-1,3,2-benzodioxasilinane as an oil.

$\delta^1$H (250 MHz, CDCl$_3$): 7.1 (2H, d, J=8.7 Hz), 6.87 (2H, d, J=8.9 Hz), 6.84 (1H, m); 6.75 (1H, dd, J=8.3 Hz and 3.1 Hz), 6.52 (1H, d, J=3.0 Hz), 4.94 (2H, s), 4.25 (6H, m); 3.88 (3H, m), 2.5–2.85 (7H, m), 1.37 (6H, t, J=6.7 Hz), 0.99 (18H, s); [α]$_D^{22}$ −18.5° (c=0.2, CHCl$_3$).

Procedure 27:

(RR)-2-(4-Hydroxyphenyl)-1-methylethyl-(1-phenylethyl)aminoboronic acid

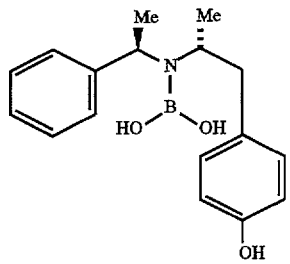

(RR)-[2-(4-Methoxyphenyl)-1-methytethyl]-(1-phenylethyl)amine hydrochloride salt[1] (10 g, 0.0327 Mol) in dichloromethane (50 ml) was treated with boron tribromide (1N in CH$_2$Cl$_2$, 72 ml) under argon and stirring continued overnight at room temperature. The mixture was then evaporated to dryness and ice added to hydrolyse the complex. The resulting white solid was collected and dried to give the title compound.

[1] D. E. Nichols, C. F. Barfknecht and D. B. Rusterholz. J. Med. Chem., 1973, 16(5), 480.

$\delta^1$H (250 MHz, CDCl$_3$+CD$_3$OD): 7.50 (5H, m), 6.83 (2H, d), 6.72 (2H, d), 4.38 (1H, q), 3.23 (1H, dd), 3.00 (1H, m), 2.67 (1H, dd), 1.78 (3H, d), 1.24 (3H, d)

m/z: FAB MH$^+$: 300 (5%), 256 (100)

Procedure 28:

(R)-4-(2-Aminopropyl)phenol

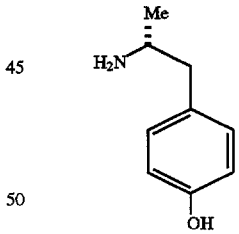

(RR)-2-(4-Hydroxyphenyl)-1-methylethyl-(1-phenylethyl)aminoboronic acid (9.73 g, 0.0325 Mol) was dissolved in methanol (120 ml) and hydrogenated at 50 psi and 50° C. with 10% palladium on charcoal (1 g) for 2 days. The mixture was allowed to cool, then filtered through Kieselguhr and evaporated to dryness to give the title compound as a pale yellow solid.

$\delta^1$H (250 MHz, CDCl$_3$): 7.06 (2H, d), 6.80 (2H, d), 4.12 (3H, br s), 3.12 (1H, m), 2.96 (1H, dd), 2.73 (1H, dd), 1.30 (3H, d).

Procedure 29:

(R)-2-(4-Hydroxyphenyl)-1-methylethylcarbamic acid, t-butyl ester

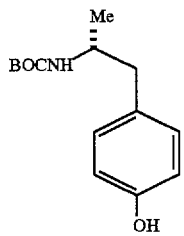

(R)-4-(2-Aminopropyl)phenol (4.91 g, 0.0325 mol) in dichloromethane (240 ml) and dry dimethylformamide (50 ml) was treated with triethylamine (7.59 ml) and di-t-butyldicarbonate (11.77 g, 1.2 equiv.) and the mixture stirred at room temperature for 1 day. After evaporation of volatile material in vacuo, the residue was washed with diethyl ether. The combined portions of diethyl ether (500 ml) were washed with water (3×100 ml) and dried over anhydrous sodium sulfate. After evaporation to dryness the residue was chromatographed on silica gel with 0–3% methanol in dichloromethane to give the title compound as a gum that slowly solidified.

$\delta^1$H (250 MHz, CDCl$_3$): 7.00 (2H, d), 6.76 (2H, d), 6.25 (1H, br s), 4.44 (1H, s), 3.83 (1H, m), 2.73 (1H, m), 2.57 (1H, dd), 1.43 (9H, s), 1.07 (3H, d).

Procedure 30:

(R)-4-(2-t-Butoxycarbonylaminopropyl) phenoxyacetic acid, methyl ester

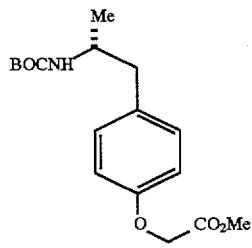

Potassium carbonate (1.95 g, 14.2 mMol) was added to a solution of (R)-2-(4-hydroxyphenyl)-1-methylethylcarbamic acid, t-butyl ester (2.96 g, 11.8 mMol) in acetone (50 ml) at room temperature under argon. Methyl bromoacetate (1.81 g, 11.8 mMol) was added dropwise and the reaction mixture was heated at reflux for 3 hours. The solvent was removed under reduced pressure and the residue was taken into ethyl acetate and washed with water (2×30 ml). The organic extracts were dried with sodium sulfate and the solvent evaporated in vacuo. The crude product was purified by chromatography on Kieselgel 60 (eluting with 20% ethyl acetate in pentane) to give the title compound as an oil.

$\delta^1$H (250 MHz, CDCl$_3$): 7.1 (2H, d, J=7.3 Hz), 6.85 (2H, d, J=7.3 Hz), 4.53 (2H, s), 4.35 (1H, br s), 3.85 (1H, m), 3.8 (3H, s), 2.5–2.8 (2H, m), 1.42 (9H, s), 1.07 (3H, d, J=6.6 Hz); $[\alpha]_D^{22}$ –7.9° (c=0.49, MeOH)

Procedure 31:

Hydroxymethylphosphonic acid, bis-(3-benzyloxypropyl)ester

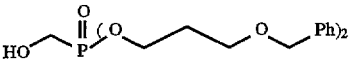

Phosphonic acid bis-(3-benzyloxypropyl)ester was prepared by the general method of Houben-Weyl, Phosphor Verbinungen, p28 and J. Amer. Chem. Soc., 1955, 77, 3522. A mixture of this crude phosphite (5 g, 0.012 Mol based on 85% purity), paraformaldehyde (0.365 g, 1 equiv.) and methylamine (0.17 ml, 0.1 equiv.) was heated under argon in an oil bath to 90° C. Further methylamine (2 ml in total) was added to promote reaction. After ca 0.5 h. the mixture was allowed to cool and then chromatographed on silica gel with 0–5%. methanol in dichloromethane to give the title compound as a colourless oil.

$\delta^1$H (250 MHz, CDCl$_3$): 7.32 (10H, m), 4.49 (4H, s), 4.22 (4H, m), 3.85 (2H, t), 3.58 (4H, t), 3.08 (1H, m), and 1.97 (4H, m).

Procedure 32:

4-Chlorobenzenesulfonyloxymethylphosphonate, bis-(3-benzyloxypropyl)ester

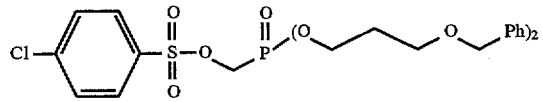

The title compound was prepared in a similar manner to the literature procedure[1] from hydroxymethylphosphonic acid, bis-(3-benzyloxy-propyl)ester as an oil.

[1] J. Cornforth and J. R. H. Wilson, JC.S Perkin I, 1994, 1897.

$\delta^1$H (250 MHz, CDCl$_3$): 7.82 (2H, d), 7.50 (10H, m), 4.48 (4H, s), 4.30–4.10 (6H, m), 3.53 (4H, t), 1.93 (4H, m).

Procedure 33:

(R)-4-(2-t-Butoxycarbonylaminopropyl) phenoxymethylphosphonic acid, bis-(3-benzyloxypropyl)ester

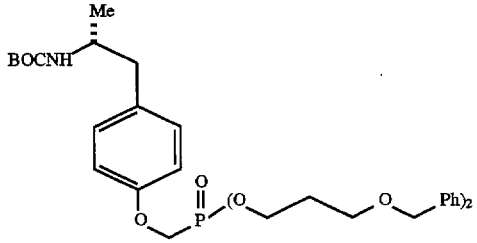

The title compound was prepared as a viscous oil from 4-chlorobenzene sulfonoxymethylphosphonate, bis-(3-benzyloxypropyl)ester and (R)-2-(4-hydroxyphenyl)-1-methylethylcarbamic acid, t-butyl ester according to the method described in Procedure 24.

$\delta^1$H (200 MHz, CDCl$_3$): 7.30 (10H, m), 7.09 (2H, d), 6.83 (2H, d), 4.48 (4H, s), 4.40–4.15 (7H, m), 3.83 (1H, br m), 3.57 (4H, t), 2.78 (1H, dd), 2.59 (1H, dd), 1.98 (4H, m), 1.52 (9H, s) and 1.05 (3H, d).

Procedure 34:

(R)-4-(2-Aminopropyl)phenoxymethylphosphonic acid, bis-(3-benzyloxypropyl)ester

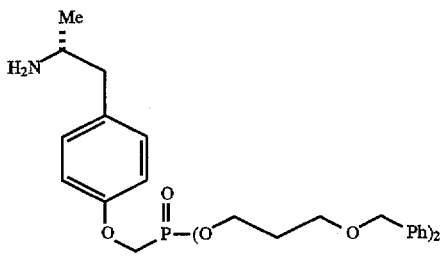

(R)-4-(2-t-Butoxycarbonylaminopropyl)phenoxymethylphosphonic acid, bis-(3-benzyloxypropyl)ester (3.2 g, 4.99 mMol) was converted into the title compound using the method described in Procedure 25.

$\delta^1H$ (200 MHz, CDCl$_3$): 7.30 (10H, m), 7.10 (2H, d), 6.85 (2H, d), 4.47 (4H, s), 4.35–4.15 (6H, m), 3.56 (4H, t), 3.22 (1H, m), 2.70 (2H, d), 2.60 (2H, br s), 1.98 (4H, 1.18 (3H, d).

Procedure 35:

(SR)-4-{2-[3-(2,2-Di-t-butyl-4H-1,3,2-benzodioxasilinan-6-yl-oxy)-2-hydroxypropylamino]propyl}phenoxymethylphosphonic acid, bis-(3-benzyloxypropyl)ester

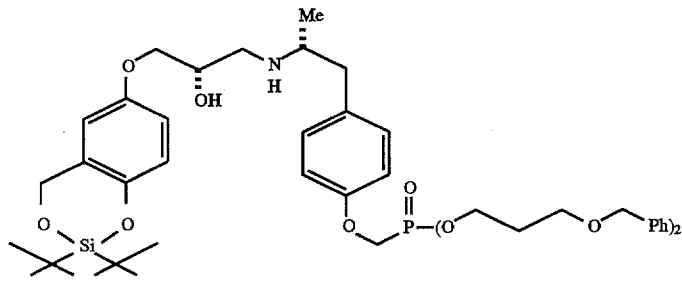

(R)-4-(2-Aminopropyl)phenoxymethylphosphonic acid, bis-(3-benzyloxypropyl)ester (2.507 g, 4.6 mMol) was reacted with (S)-2,2-di-t-butyl-6-(oxiran-2-ylmethoxy)-4H-1,3,2-benzodioxasilinane (1.557 g, 1 equiv.) using the method described in Procedure 14 to yield the title compound as a colourless gum.

$\delta^1H$ (200 MHz, CDCl$_3$): 7.30 (10H, m), 7.09 (2H, d), 6.83 (3H, m), 6.70 (1H, dd), 6.49 (1H, d), 4.93 (2H, s), 4.47 (4H, s), 4.35–4.20 (6H, m), 3.99 (1H, m), 3.87 (2H, d), 3.55 (4H, t), 3.1–2.5 (5H, m), 2.32 (2H, br s), 1.98 (4H, m), 1.11 (3H, d), 1.03 (18H, s).

Procedure 36:

(SR)-4-{2-[3-(2,2-Di-t-butyl-4H-1,3,2-benzodioxasilinan-6-yl-oxy)-2-hydroxypropylamino]propyl}phenoxymethylphosphonic acid, bis-(3-hydroxypropyl)ester

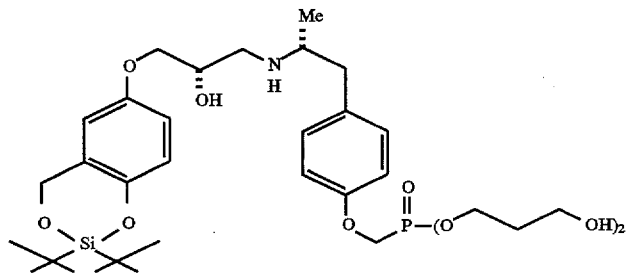

(SR)-4-{2-[3-(2,2-Di-t-butyl-4H-1,3,2-benzodioxasilinan-6-yl-oxy)-2-hydroxypropylamino]propyl}phenoxymethylphosphonic acid, bis-(3-benzyloxypropyl)ester (1 g, 1.14 mmol) was hydrogenated at 50° C. and 50 psi for 2 days in methanol (120 ml) in the presence of 10% palladium on charcoal (1.0 g). After allowing the mixture to cool, it was filtered through Kieselguhr, evaporated to dryness and purified by column chromatography on silica gel eluting with 0–15% methanol dichloromethane. The title compound was obtained as a clear gum.

δ$^1$H (250 MHz, CDCl$_3$): 7.13 (2H, d), 6.90 (2H, d), 6.82 (1H, d), 6.70 (1H, dd), 6.49 (1H, d), 4.93 (2H, s), 4.40–4.25 (6H, m), 4.07 (1H, m), 3.88 (2H, m), 3.73 (4H, t), 3.40–2.60 (9H, overlapping m+br. s), 1.90 (4H, m), 1.18 (3H, d), 1.02 (18H, s).

Procedure 37:

Hydroxymethylphenylphosphinic acid, ethyl ester

The title compound was prepared by the general method of Procedure 31 by hydroxymethylation of phenylphosphinic acid ethyl ester[1] (10.136 g, 0.059 Mol). The product was obtained as a colourless viscous oil after chromatography.

[1] D. G. Hewitt. Aust. J. Chem., 1979, 32, 463.

δ$^1$H (250 MHz, CDCl$_3$): 7.83 (2H, m), 7.65–7.42 (3H, m), 4.26–3.90 (5H, m), 1.32 (3H, t).

Procedure 38:

4-Chlorobenzenesulfonyloxymethylphenylphosphinic acid ethyl ester

The title compound was prepared as a white crystalline solid, m.p. 70°–72° C., from hydroxymethylphenylphosphinic acid, ethyl ester (9.525 g, 0.0476 Mol) by a method similar to that of Procedure 32.

δ$^1$H (250 MHz, CDCl$_3$): 7.83–7.58 (5H, m), 7.58–7.40 (4H, m), 4.40 (1H, dd), 4.28–4.00 (3H, m), 1.35 (3H, t).

Procedure 39:

(R)-4-(2-t-Butoxycarbonylaminopropyl) phenoxymethylphenylphosphinic acid, ethyl ester The title compound was prepared as a colourless gum from 4-chlorobenzenesulfonoxymethylphenylphosphinic acid ethyl ester (3.91 g, 10.4 mMol) and (R)-2-(4-hydroxyphenyl)-1-methylethylcarbamic acid, t-butyl ester (2.5 g, 9.96 mMol) by the method described in Procedure 24.

δ$^1$H (200 MHz, CDCl$_3$): 7.93 (2H, m), 7.52 (3H, m), 7.07 (2H, d), 6.82 (2H, d), 4.52–4.0 (5H, m), 3.81 (1H, br), 2.76 (1H, dd), 2.57 (1H, dd), 1.42 (9H, s), 1.38 (3H, t), 1.03 (3H, d).

Procedure 40:

(R)-4-(2-Aminopropyl) phenoxymethylphenylphosphinic acid, ethyl ester

The title compound was prepared by a method similar to that described in Procedure 25 from (R)-4-(2-t-butoxycarbonylaminopropyl)phenoxymethylphenylphosphinic acid, ethyl ester (2.647 g, 6. 1 mMol).

δ$^1$H (250 MHz, CDCl$_3$): 7.93 (2H, m), 7.65–7.44 (8H, m), 7.07 (2H, d), 6.83 (2H, d), 4.44 (1H, dd), 4.36–4.02 (3H, m), 3.09 (1H, m), 2.63 (1H, dd), 2.43 (1H, dd), 1.38 (3H, t), 1.08 (3H, d).

Procedure 41:

(SR)-4-{2-[3-(2,2-Di-t-butyl-4H-1,3,2-benzodioxasilinan-6-yl-oxy)-2-hydroxypropylamino] propyl}phenoxymethylphenylphosphinic acid, ethyl ester The title compound was prepared as a colourless gum by a method similar to that described in Procedure 13 from (R)-4-(2-aminopropyl)phenoxymethylphenyl phosphinic acid, ethyl ester (1 g, 3 mMol) and (S)-2,2-di-t-butyl-6-(oxiran-2-ylmethoxy)-4H-1,3,2-benzodioxasilinane (1.009 g, 3 mMol.)

δ$^1$H (400 MHz, CDCl$_3$): 7.92 (2H, m), 7.59 (1H, m), 7.51 (2H, m), 7.07 (2H, d), 6.82 (3H, m), 6.69 (1H, dd), 6.48 (1H, d), 4.93 (2H, s), 4.43 (1H, dd), 4.30 (1H, m), 4.25–4.05 (2H, m), 3.98 (1H, m), 3.88 (2H, m), 3.03–2.35 (7H, m), 1.38 (3H, t), 1.10 (3H, d), 1.03 (18H, s).

Procedure 42:

3-Benzyloxypropylphosphinic acid

The title compound was prepared from allylbenzyl ether and 50% aqueous phosphinic acid by an analogous procedure to that described in J. Inorg. Nucl. Chem., 1965, 27, 697.

δ(CDCl₃): 10.83(1H, s, exchanges with D₂O); 7.36–7.18 (5H, m.); 7.10(1H, d, J=546.57 Hz.); 4.49(2H, s.); 3.52(2H, t, J=5.77 Hz.); 1.94–1.80(4H, m.).

Procedure 43:

3-Benzyloxypropylphosphinic acid, n-butyl ester

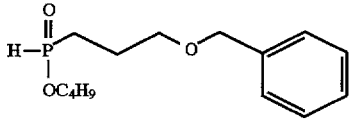

The title compound was prepared from 3-benzyloxypropylphosphinic acid and n-butanol according the general procedure described in European Patent 0093010. The compound was used without further purification.

δ(CDCl₃): 7.39–7.15(5H, m.); 7.09(1H, ddd, J=532.27, 1.92, 1.65 Hz.); 4.51(2H, s.); 4.17–3.91(2H, m.); 3.53(2H, t, J=5.77 Hz.); 1.99–1.72(4H, m.); 1.69–1.58(2H, m.); 1.47–1.33(2H, m.); 0.94(3H, t, J=7.15 Hz.).

Procedure 44:

3-Benzyloxypropylhydroxymethylphosphinic acid, n-butyl ester

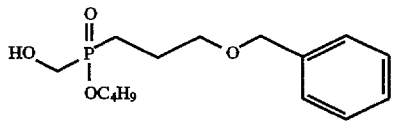

The title compound was prepared from 3-benzyloxypropylphosphinic acid n-butyl ester and paraformaldehyde according to the method described in Procedure 31. Purification by chromatography, eluting with dichloromethane containing 5% methanol, gave an oil.

δ(CDCl₃): 7.38–7.25(5H, m.); 4.50(2H, s.); 4.09–3.97 (2H, m.); 3.83(2H, t, J=4.95 Hz.); 3.77–3.71 (1 H, m. exchanges with D₂O); 3.54–3.51 (2H, m.); 1.99–1.86(4H, m.); 1.68–1.60(2H, m.); 1.48–1.34(2H,m.); 0.92(3H, t, J=7.42 Hz.).

Procedure 45:

3-Benzyloxypropyl-(4-chlorophenylsulfonyoxymethyl)phosphinic acid, n-butyl ester

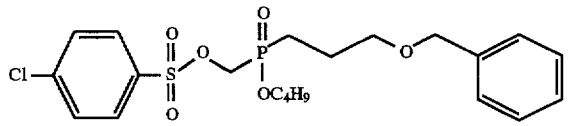

The title compound was prepared from 3-benzyloxypropylhydroxy-methylphosphinic acid, n-butyl ester and 4-chlorobenzenesulfonyl chloride according to the method described in Procedure 32. The crude compound was used without further purification.

δ(CDCl₃): 7.84(2H, d, J=8.80 Hz.); 7.52(2H, d, J=8.79 Hz.); 7.36–7.26(5H, m.); 4.50(2H, s.); 4.27–3.78(4H, m.); 3.51(2H, t, J=6.05 Hz.); 1.97–1.83(4H, m.); 1.67–1.55(2H, m.); 1.42–1.26(2H, m.); 0.91(3H, t, J=7.15 Hz.).

Procedure 46:

4-(2-t-Butoxycarbonylaminoethyl)phenoxymethyl-(3-benzyloxypropyl)phosphinic acid, n-butyl ester

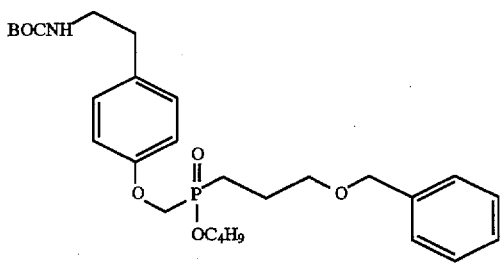

The title compound was prepared from 3-benzyloxypropyl-(4-chlorobenzenesulfonyloxymethyl) phosphinic acid, n-butyl ester and 2-(4-hydroxyphenyl) ethylcarbamic acid, t-butyl ester according to the procedure described in Procedure 24. The crude product was purified by chromatography, eluting with dichloromethane containing 3% methanol, to give an oil.

δ(CDCl₃): 7.37–7.24(5H, m.); 7.11(2H, d, J=8.80 Hz.); 6.87(2H, d, J=8.80 Hz.); 4.49(2H, s.); 4.27–3.95(4H, m.); 3.55(2H, t, J=6.05 Hz.); 3.36–3.32(2H, m.); 2.74(2H, t, J=6.88 Hz.); 2.06–1.79(5H, m.); 1.71–1.60(2H, m.); 1.47–1.31 (2H, m.); 1.25(9H, s.); 0.91(3H, t, J=7.15 Hz.).

Procedure 47:

4-(2-Aminoethyl)phenoxymethyl(3-benzyloxypropyl)phosphinic acid, n-butyl ester

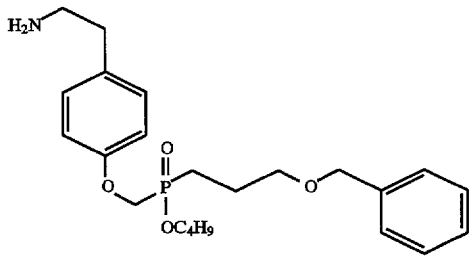

The title compound was prepared from 4-(2-t-butoxycarbonylaminoethyl)phenoxymethyl(3-benzyloxypropyl)phosphinic acid, n-butyl ester according to the method described in Procedure 25. The crude product was used without further purification.

δ(CDCl₃): 7.36–7.26(5H, m.); 7.12(2H, d, J=8.80 Hz.); 6.87(2H, d, J=8.53 Hz.); 4.49(2H, s.); 4.23–4.19(2H, m.); 4.15–3.97(2H, m.); 3.54(2H, t, J=5.78 Hz.); 2.94(2H, t, J=6.60 Hz.); 2.70(2H, t, J=6.60 Hz.); 2.05–1.95(4H, m.) 1.67–1.59(4H, m. 2H exchange with D₂O); 1.43–1.35(2H, m.); 0.91(3H, t, J=7.42 Hz.).

Procedure 48:

(S)4-{2-[3-(2,2-Di-t-butyl-4H-1,3,2-benzodioxasilinan-6-yloxy)-2-hydroxypropylamino] ethyl}phenoxymethyl(3-benzyloxypropyl) phosphinic acid, n-butyl ester

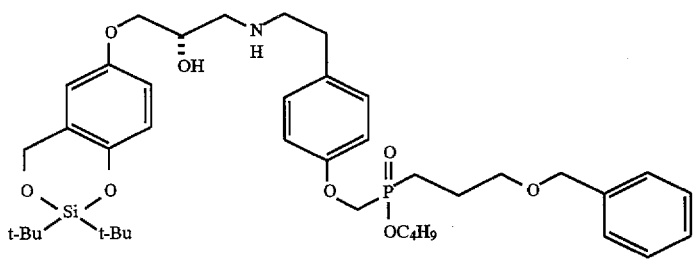

The title compound was prepared from 4-(2-aminoethyl) phenoxymethyl(3-benzyloxypropyl)phosphinic acid, n-butyl ester and (S)-2,2-di-t-butyl-6-(oxiran-2-ylmethoxy)-4H-1,3,2-benzodioxasilinane according to the method described in Procedure 13. The crude product was purified by chromatography over silica gel eluting with dichloromethane containing 3% methanol to give a viscous gum.

δ(CDCl$_3$+D$_2$O): 7.36–7.26(5H, m.); 7.13(2H, d, J=8.80 Hz.); 6.86(2H, d, J=8.80 Hz.); 6.83(1H, d, J=8.80 Hz.); 6.72(1H, dxd, J=8.80 & 3.03 Hz.); 6.50(1H, d, J=3.02 Hz.); 4.94(2H, s.); 4.49(2H, s.); 4.22–3.88(7H, m.); 3.54(2H, t, J=6.05 Hz.); 2.92–2.70(6H, m.); 2.06–1.93(4H, m.); 1.46–1.30(2H, m.); 1.02(18H, s.); 0.91(3H, t, J=7.14 Hz.).

Procedure 49:

(R)-4-(2-t-Butoxycarbonylaminopropyl) phenoxymethyl-(3-benzyloxypropyl)phosphinic acid, n-butyl ester

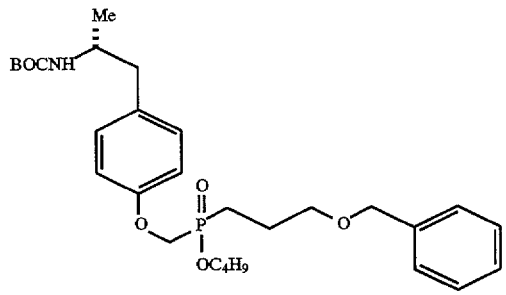

The title compound was prepared from 3-benzyloxypropyl-(4-chlorobenzenesulfonyloxymethyl) phosphinic acid, n-butyl ester and (R)-2-(4-hydroxyphenyl)-1-methylethylcarbamic acid, t-butyl ester according to the method described in Procedure 24. The crude product was purified by chromatography, eluting with dichloromethane containing 3% methanol, to give an oil.

δ(CDCl$_3$+D$_2$O): 7.34–7.26(5H, m.); 7.11 (2H, d, J=8.53 Hz.); 6.86(2H, d, J=8.52 Hz.); 4.50(2H, s.); 4.36–3.85(5H, m.); 3.56(2H, t, J=5.91 Hz.); 2.80(1H, dd, J=13.48, 3.49 Hz.); 2.60(1H, dd, J=13.48, 7.43 Hz); 2.17–2.00(4H, m.); 1.69–1.62(4H, m.); 1.43(9H, s.); 1.06(3H, d, J=6.60 Hz.); 0.91(3H, t, J=6.60 Hz.).

Procedure 50:

(R)-4-(2-Aminopropyl)phenoxymethyl-(3-benzyloxypropyl)phosphinic acid, n-butyl ester

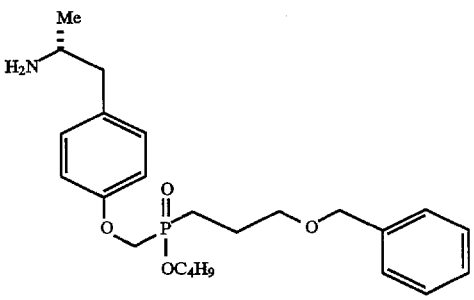

The title compound was prepared from (R)-4-(2-t-butoxycarbonylaminopropyl)phenoxymethyl(3-benzyloxypropyl)phosphinic acid, n-butyl ester according to the method described in Procedure 25. The crude product was used without further purification δ(CDCl$_3$+D$_2$O): 7.36–7.26(5H, m.); 7.12(2H, d, J=8.80 Hz.); 6.87(2H, d, J=8.80 Hz.); 4.50(2H, s.); 4.21(2H, d, J=6.88 Hz.); 4.17–3.97(2H, m.); 3.54(2H, t, J= 3.55 Hz.); 3.25–3.10(1H, m.); 2.74–2.53(2H, m.); 2.11–1.93(4H, m.); 1.67–1.59(2H, m.); 1.43–1.35(2H, m.); 1.13(3H, d, J=6.32 Hz.); 0.91(3H, t, J=7.42 Hz.).

Procedure 51:

(SR)-4-{2-[3-(2,2-Di-t-butyl-4H-1,3,2-benzodioxasilinan-6-yloxy)-2-hydroxypropylamino] propyl}phenoxymethyl-(3-benzyloxypropyl) phosphinic acid, n-butyl ester

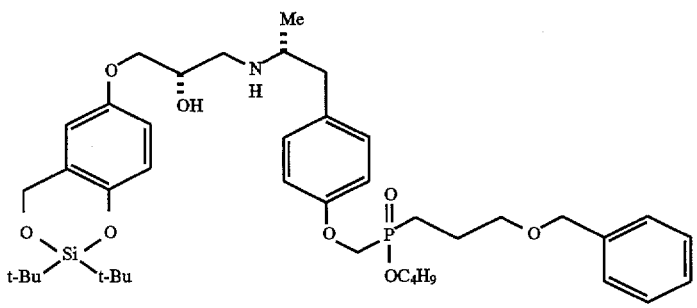

The title compound was prepared from (R)-4-(2-aminopropyl)phenoxymethyl-(3-benzyloxypropyl)phosphinic acid, n-butyl ester and (S)-2,2-di-t-butyl-6-(oxiran-2-ylmethoxy)-4H-1,3,2-benzodioxasilinane according to the method described in Procedure 13. The crude product was purified by chromatography over silica gel eluting with dichloromethane containing 3% methanol to give a viscous gum.

δ(CDCl$_3$): 7.37–7.31(5H, m.); 7.11(2H, d, J=8.52 Hz.); 6.86(2H, d, J=8.60 Hz.); 6.83(1H, J=8.80 Hz.); 6.72(1H, dd, J=8.80, 3.30 Hz.); 6.50(1H, d, J=2.75Hz.); 4.94(2H, s.); 4.50(2H, s.); 4.21–3.88(8H, m.); 3.54(2H, m.); 2.92–2.66 (5H, m.); 2.57(1H, dd, J=13.47, 6.50 Hz.); 2.09–1.90(4H, m.); 1.77–1.60(2H, m.); 1.57–1.38(2H, m.); 1.02(18H, s.); 1.06(3H, d, J=6.25 Hz.); 0.92(3H, t, J=7.14 Hz.).

Procedure 52:

Cyclohexylphosphinic acid, n-butyl ester

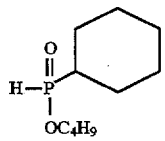

The title compound was prepared from cyclohexylphosphinic acid and n-butanol according the the method described in Procedure 43. The compound was used without further purification.

δ(CDCl$_3$): 6.82(1H, d, J=517.97 Hz.); 4.17–3.92(2H, m.); 1.92–1.22(15H, m.); 0.94(3H, t, J=7.43 Hz.).

Procedure 53:

Cyclohexylhydroxymethylphosphinic acid, n-butyl ester

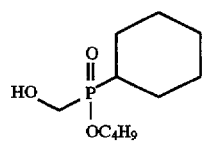

The title compound was prepared from cyclohexylphosphinic acid, n-butyl ester and paraformaldehyde according to the method described in Procedure 31. Purification by chromatography, eluting with dichloromethane containing 5% methanol, gave an oil.

δ(CDCl$_3$+D$_2$O): 4.13–4.93(2H, m.); 3.88–3.65(2H, m.); 1.97–1.22(15H, m.); 0.93(3H, t, J=7.15 Hz.).

Procedure 54:

(4-Chlorobenzenesulfonyloxy)cyclohexylphosphinic acid, n-butyl ester

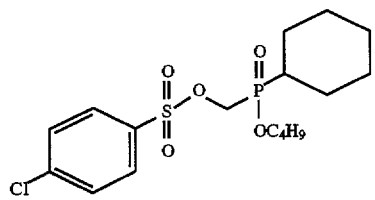

The title compound was prepared from cyclohexylhydroxymethylphosphinic acid, n-butyl ester and 4-chlorobenzenesulfonyl chloride according to the method described in Procedure 32. The crude compound was used without further purification.

δ(CDCl$_3$): 7.87(2H, d, J=8.80 Hz.); 7.57(2H, d, J=8.80 Hz.); 4.19(2H, d, J=7.70 Hz.); 4.12–3.81(2H, m.); 205–1.20 (15H,m.); 0.91(3H, t, 7.15 Hz.).

Procedure 55:

4-(2-t-Butoxycarbonylaminoethyl)phenoxymethyl cyclohexylphosphinic acid, n-butyl ester

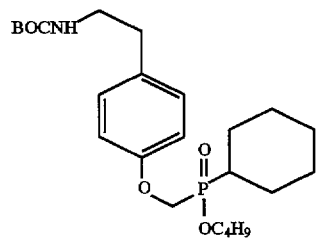

The title compound was prepared from (4-Chlorobenzenesulfonyloxy)cyclohexylphosphinic acid, n-butyl ester and 2-(4-hydroxyphenyl)ethylcarbamic acid, t-butyl ester according to the method described in Procedure 24. The crude product was purified by chromatography, eluting with dichloromethane containing 3% methanol, to give an oil.

δ(CDCl$_3$): 7.13(2H, d, J=8.80 Hz.); 6.88(2H, d, J=8.80 Hz.); 4.50(1H, s. exchanges with D$_2$O); 4.32–3.95(4H, m.); 3.34(2H, q, J=7.15 Hz.); 2.74(2H, t, J=7.15 Hz.); 2.07–1.47 (15H, m.); 1.44(9H, s.); 0.92(3H, t, J=7.43 Hz.);

Procedure 56:

4-(2-Aminoethyl)
phenoxymethylcyclohexylphosphinic acid, n-butyl ester

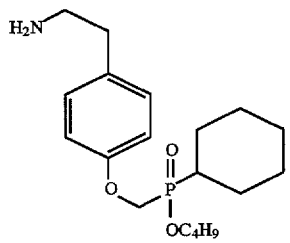

The title compound was prepared from 4-(2-t-butoxycarbonylaminoethyl) phenoxymethylcyclohexylphosphinic acid, n-butyl ester according to the method described in Procedure 25. The crude product was used without further purification.

δ(CDCl$_3$+D$_2$O): 7.14(2H, d, J=8.80 Hz.); 6.68(2H, d, J=8.80 Hz.); 4.26–3.98(4H, m.); 2.96–2.90(2H, m.); 2.75–2.70(2H, m.); 2.12–1.26(15H, m.): 0.92(3H, t, J=7.15 Hz.);

Procedure 57:

(S)-4-{2-[3-(2,2-Di-t-butyl-4H-1,3,2-benzodioxasilinan-6-yloxy)-2-hydroxypropylamino]ethyl}phenoxymethylcyclohexylphosphinic acid, n-butyl ester

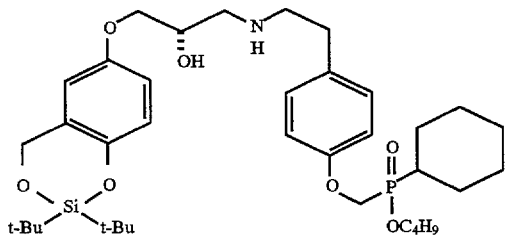

The title compound was prepared from 4-(2-aminoethyl) phenoxypropyl methylcyclohexylphosphinic acid, n-butyl ester and (S)-2,2-di-t-butyl-6-(oxiran-2-ylmethoxy)-4H-1,3,2-benzodioxasilinane according to the method described in Procedure 13. The crude product was purified by chromatography over silica gel eluting with dichloromethane containing 3% methanol to give a viscous gum.

δ(CDCl$_3$+D$_2$O): 7.14(2H, d, J=8.56 Hz.); 6.88(2H, d, J=8.65 Hz.); 6.82(1H, d, J=8.79 Hz.); 6.72(1H, dd, J=8.78, 3.00 Hz.); 6.50(1H, d, J=2.95 Hz.); 4.95(2H, s.); 4.26–4.11 (4H, m.); 4.09–3.95(3H, m.); 3.89(2H, d, J=5.11 Hz.); 2.92–2.83(2H, m.); 2.77–2.72(2H, m.); 2.03–1.93(3H, m.); 1.93–1.83(2H, m.); 1.72–1.61(4H, m.); 1.51–1.40(4H, m.); 1.39–1.21(2H, m.); 1.03(18H, s.); 0.91(3H, t, J=7.39 Hz.).

Procedure 58:

(S)-4-{2-[3-(4-Benzyloxyphenoxy)-2-hydroxypropylamino]ethyl}phenoxymethylcyclohexylphosphinic acid, n-butyl ester

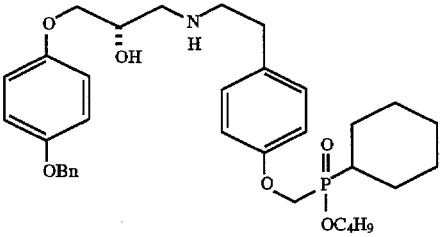

The title compound was prepared from 4-(2-aminoethyl) phenoxy methylcyclohexylphosphinic acid, n-butyl ester and (S)-2-(4-benzyloxyphenoxymethyl)oxirane according to the method described in Procedure 13.

δ(CDCl$_3$): 7.44–7.26 (5H, m), 7.14 (2H, d, J=8.8 Hz), 6.91–6.80 (6H, m), 5.01 (2H, s), 4.25–4.0 (5H, m), 3.91 (2H, d, J=5 Hz), 3.0–2.75 (6H, m), 2.1–1.25 (15H, m), 0.92 (3H, t, J=7.4 Hz).

Procedure 59:

(S)-4-{2-[3-(3-Benzyloxyphenoxy)-2-hydroxypropylamino]ethyl}phenoxymethylcyclohexylphosphonic acid, n-butyl ester

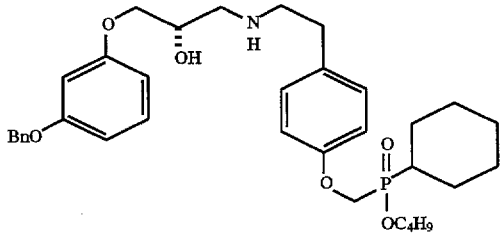

The title compound was prepared from 4-(2-aminoethyl) phenoxypropylmethyl cyclohexylphosphinic acid, n-butyl ester and (S)-2-(3-benzyloxyphenoxymethyl)oxirane according to the method described in Procedure 13.

δ(CDCl$_3$): 7.5–7.3 (5H, m), 7.2–7.1 (3H, m), 6.88 (2H, d, J=8.5 Hz), 6.65–6.45 (3H, m), 5.04 (2H, s), 4.25–3.9 (7H, m), 2.95–2.75 (6H, m), 2.1–1.25 (15H, m), 0.92 (3H, t, J=7.2 Hz).

Procedure 60:

(R)-4-(2-t-Butoxycarbonylaminopropyl) phenoxymethyl, cyclohexylphosphoic acid, n-butyl ester

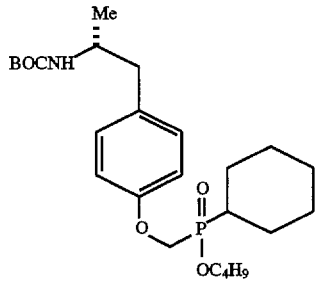

The title compound was prepared from (4-chlorophenylsulfonyloxy)cyclohexylphosphonic acid, n-butyl ester and (R)-2-(4-hydroxyphenyl)-1-methylethylcarbamic acid, t-butyl ester according to the method described in Procedure 24. The crude product was purified by chromatography, eluting with dichloromethane containing 3% methanol, to give an oil.

δ(CDCl$_3$): 7.10(2H, d, J=8.53 Hz.); 6.87(2H, d, J=8.60 Hz.); 4.34–3.85(6H, m. 1H exchanges with D$_2$O); 2.78(1H, dd, J=13.74, 5.49 Hz.); 2.60(1H, dd, J=13.48, 7.43 Hz.); 2.04–1.13(15H, m.); 1.42(9H, s.); 1.07(3H, d, J=6.87 Hz.); 0.92(3H, t, J32 7.42 Hz.).

Procedure 61:

(R)-4-(2-Aminopropyl) phenoxymethylcyclohexylphosphinic acid, n-butyl ester

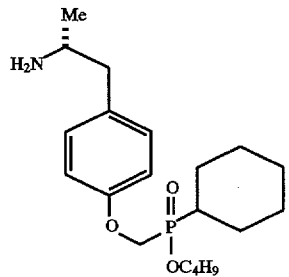

The title compound was prepared from (R)-4-(2-t-butoxycarbonylaminopropyl) phenoxymethylcyclohexylphosphinic acid, n-butyl ester according to the method described in Procedure 25. The crude product was used without further purification.

δ(CDCl$_3$): 7.13(2H, d, J=8.80 Hz.); 6.88(2H, d, J=8.80 Hz.); 4.23–4.02(4H, m.); 3.20–3.12(1H, m.); 2.68(1H, dd, J=13.48, 5.50 Hz.); 2.54(1H, dd, J=13.47, 7.70 Hz.); 2.06–1.21(17H, m. 2H exchanged with D$_2$O); 1.14(3H, d, J=6.32 Hz.); 0.92(3H, t, J=7.15 Hz.).

Procedure 62:

(SR)-4-{2-[3-(2,2-di-t-Butyl-4H-1,3,2-benzodioxasilinan-6-yloxy)-2-hydroxypropylamino]propyl}phenoxymethylcyclohexylphosphinic acid, n-butyl ester

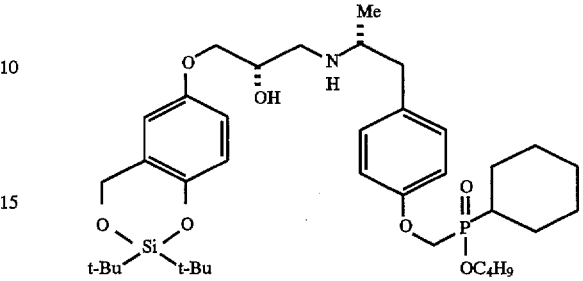

The title compound was prepared from (R)-4-(2-aminopropyl)phenoxymethylcyclohexylphosphinic acid, n-butyl ester and (S)-2,2-di-t-butyl-6-(oxiran-2-ylmethoxy)-4H-1,3,2-benzodioxasilinane according to the method described in Procedure 13. The crude product was purified by chromatography over silica eluting with dichloromethane containing 3% methanol to give a viscous gum.

δ(CDCl$_3$+D$_2$O): 7.10(2H, d, J=8.53 Hz.); 6.87(2H, d, J=8.80 Hz.); 6.83(1H, d, J=8.80 Hz.); 6.70(1H, dxd, J=8.80 & 3.02 Hz.); 6.50(1H, d, J=3.02 Hz.); 4.94(2H, s.); 4.26–3.88(7H, m.); 2.91–2.53(5H, m.); 2.05–1.26(15H, m.); 1.06(3H, d, J=6.32 Hz.); 1.02(18H, s.); 0.92(3H, t, J=7.43 Hz.).

Procedure 63:

n-Hexylphosphinic acid

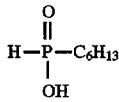

The title compound was prepared from n-hexene and 50% aqueous phosphinic acid by an analogous procedure to that described in *J. Inorg. Nucl. Chem.*, 1965, 27, 697.

δ(CDCl$_3$): 12.10(1H, s, exchanges with D$_2$O); 7.08(1H, dd, J=540.10, 1.93 Hz.); 1.82–1.51(4H, m.); 1.42–1.23(6H, m.); 0.87(3H, t, J=6.87 Hz.).

Procedure 64:

n-Hexylphosphinic acid, n-butyl ester

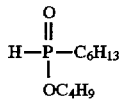

The title compound was prepared from n-hexylphosphinic acid and n-butanol according the the method described in Procedure 43. The compound was used without further purification.

δ(CDCl$_3$): 7.08(1H, d, J=525.92 Hz.); 4.12–3.98(2H, m.); 1.80–1.26(14H, m.); 0.97–0.86(6H, m.).

Procedure 65:

n-Hexylhydroxymethylphosphinic acid, n-butyl ester

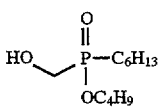

The title compound was prepared from n-hexylphosphinic acid, n-butyl ester and paraformaldehyde according to the method described in Procedure 31. Purification by chromatography, eluting with dichloromethane containing 5% methanol, gave an oil.

δ(CDCl₃): 4.09–3.99(3H, m.); 3.89–3.79(2H, m.); 1.83–1.75(2H, m.); 1.69–1.46(4H, m.); 1.43–1.29(8H, m.); 0.96–0.86(6H, m.).

Procedure 66:

4-Chlorobenzenesulfonyloxymethyl-n-hexylphosphinic acid, n-butyl ester

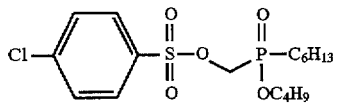

The title compound was prepared from n-hexylhydroxymethylphosphinic acid, n-butyl ester and 4-chlorobenzenesulfonyl chloride and according to the procedure described in procedure 32. The crude compound was used without further purification.

δ(CDCl₃): 7.89(2H, d, J=8.88 Hz.); 7.57(2H, d, J=8.80 Hz.); 4.25–3.84(4H, m.); 2.04–1.23(14H, m.); 0.97–0.86 (6H, m.).

Procedure 67:

(R)-4-(2-t-Butoxycarbonylaminopropyl)phenoxymethyl-n-hexylphosphinic acid, n-butyl ester

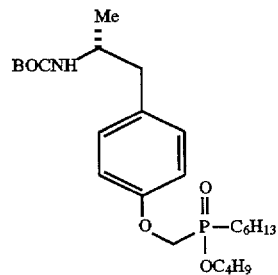

The title compound was prepared from 4-chlorobenzenesulfonyloxymethyl-n-hexylphosphinic acid, n-butyl ester and (R)-2-(4-hydroxyphenyl)-1-methylethylcarbamic acid, t-butyl ester according to the method described in Procedure 24. The crude product was purified by chromatography, eluting with dichloromethane containing 3% methanol, to give an oil.

δ(CDCl₃): 7.11(2H, d, J=8.80 Hz.); 6.87(2H, d, J=8.52 Hz.); 4.21–4.00(4H, m.); 3.83(1H, s.); 3.41(1H, m.); 2.77 (1H, dd, J=13.83, 5.58 Hz.); 2.58(1H, dd, J=13.76, 7.12 Hz.); 1.89–1.84(2H, m.); 1.68–1.60(6H, m.); 1.44–1.39(2H, m.); 1.43(9H, s.); 1.38–1.25(4H, m.); 1.07(3H, d, J=6.95 Hz.); 0.94–0.85(6H, m.).

Procedure 68:

(R)-4-(2-Aminopropyl)phenoxymethyl-n-hexylphosphinic acid, n-butyl ester

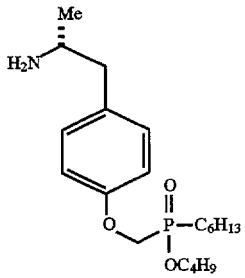

The title compound was prepared from (R)-4-(2-t-butoxycarbonylaminopropyl)phenoxymethyl-n-hexylphosphinic acid, n-butyl ester according to the method described in Procedure 25. The crude product was used without further purification.

δ(CDCl₃): 7.12(2H, d, J=8.53 Hz.); 6.89(2H, d, J=8.80 Hz.); 4.22–3.86(6H, m. 2H exchanges with D₂O); 3.24(1H, q, J=6.59 Hz.); 2.70(2H, d, J=6.88 Hz.); 1.95–1.84(2H, m.); 1.71–1.58(4H, m.); 1.47–1.25(8H, m.); 1.18(3H, d, J=6.32 Hz.); 0.95–0.84(6H, m.).

Procedure 69:

(SR)-4-{2-[3-(2,2-Di-t-butyl-4H-1,3,2-benzodioxasilinan-6-yloxy)-2-hydroxypropylamino]propyl}phenoxymethyl-n-hexylphosphinic acid, n-butyl ester

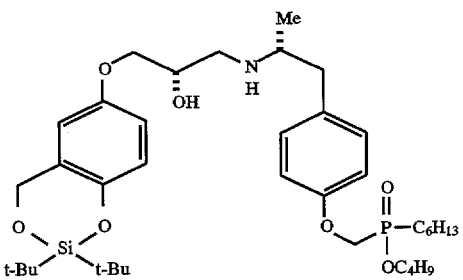

The title compound was prepared from (R)-4-(2-aminopropyl)phenoxymethyl-n-hexylphosphinic acid n-butyl ester and (S)-2,2-di-t-butyl-6-(oxiran-2-ylmethoxy)-4H-1,3,2-benzodioxasilinane according to the method described in Procedure 13. The crude product was purified by chromatography over silica gel eluting with dichloromethane containing 3% methanol to give a viscous gum.

δ(CDCl₃): 7.12(2H, d, J=8.53 Hz.); 6.87(2H, d, J=8.80 Hz.); 6.72(1H, d, J=8.80 Hz.); 6.72(1H, dd, J=8.80, 3.03 Hz.); 6.50(1H, d, J=3.03 Hz.); 4.92(2H, s.); 4.27–3.86(8H, m. 2H exchange with D₂O); 2.93–2.86(1H, m.); 2.84–2.63 (2H, m.); 2.57(1H, dd, J=13.47, 6.59 Hz.); 1.96–1.84(4H, m.); 1.71–1.58(4H, m.); 1.47–1.15(8H, m.); 1.06(3H, d, J=6.32 Hz.); 1.03(18H, s.); 0.97–0.85(6H, m.).

Procedure 70:

(S)-1-(4-Benzyloxyphenoxy)-3-[N-2-(4-hydroxyphenyl)ethylamino]propan-2-ol

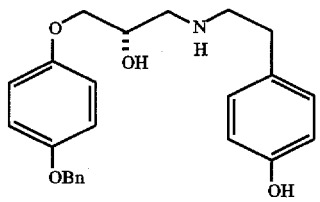

The title compound was prepared from tyramine and (S)-2-(4-benzyloxyphenoxymethyl)oxirane according to the method described in Procedure 13.

δ(d⁶-DMSO): 9.3–8.9 (1H, b, exchanged with D₂O), 7.5–7.25 (5H, m), 6.98 (2H, d, J=8.6 Hz), 6.92 (2H, d, J=9 Hz), 6.83 (2H, d, J=9 Hz), 6.65 (2H, d, J=8.6 Hz), 5.02 (2H, s), 4.9 (1H, b, exchanged with D₂O), 3.9–3.75 (3H, m), 2.75–2.55 (6H, m).

Procedure 71:

(S)-N-Benzyl-1(4-benzyloxyphenoxy)-3-[N-2-(4-hydroxyphenyl)ethylamino]propan-2-ol

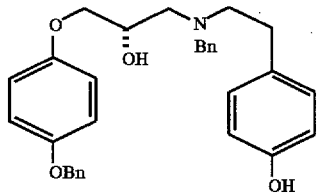

A solution of (S)-1-(4-benzyloxyphenoxy)-3-[N-2-(4-hydroxyphenyl)ethylamino]propan-2-ol (1.9 g, 4.8 mMol) and benzyl bromide (0.57 ml, 4.8 mMol) in dimethylformamide (10 ml) containing sodium carbonate (770 mg, 7.2 mMol) was stirred at room temperature for 18 hours. The mixture was filtered and the residue was washed with ethyl acetate. The filtrates were combined, washed with water and brine, dried and evaporated. Purification of the residue by flash chromatography (silica gel, 50% ethyl acetate in hexane) gave the title compound.

δ(CDCl₃+D₂O): 7.5–7.25 (10H, m), 6.96 (2H, d, J=8.5 Hz), 6.88 (2H, d, J=9.1 Hz), 6.79 (2H, d, J=9.1 Hz), 6.71 (2H, d, J=8.5 Hz), 5.01 (2H, s), 4–3.78 (4H, m), 3.59 (1H, d, J=13.5 Hz), 2.9–2.6 (6H, m).

Procedure 72:

(S)-N-Benzyl-4-{2-[-3-(4-benzyloxyphenoxy)-2-hydroxypropylamino]ethyl}phenoxymethyl-n-hexylphosphinic acid, n-butyl ester

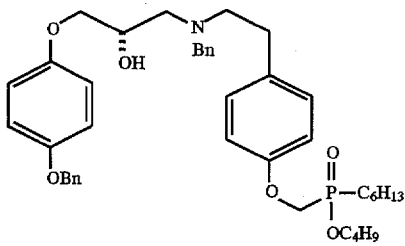

The title compound was prepared from (S)-N-benzyl-1-(4-benzyloxyphenoxy)-3-[N-2-(4-hydroxyphenyl)ethylamino]propan-2-ol and 4-chlorobenzenesulfonyloxymethyl-n-hexylphosphinic acid, n-butyl ester according to the method described in Procedure 24.

δ(CDCl₃+D₂O): 7.45–7.25 (10H, m), 7.04 (2H, d, J=8.5 Hz), 6.9–6.78 (6H, m), 5.01 (2H, s), 4.2–3.83 (8H, m), 3.54 (1H, d, J=12.3 Hz), 2.9–2.6 (6H, m), 1.9 (2H, m), 1.65 (4H, m), 1.5–1.25 (8H, m), 0.95–0.85 (6H, m).

Procedure 73:

Phosphonic acid, bis-(2-phenylethyl)ester

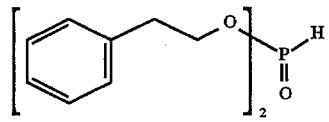

The title compound was prepared from 2-phenylethanol and phosphorus tribromide according to the method described in Procedure 31. Purification by chromatography on silica-gel eluting with 5% methanol in dichloromethane gave the title compound as an oil.

δ(CDCl₃): 7.92–5.32 (1H, d.); 7.16–7.33 (10H, m.); 4.10–4.28 (4H, m.); 2.92–3.04 (4H, t.)

Procedure 74:

Hydroxymethyphosphonic acid, bis-(2-phenylethyl) ester

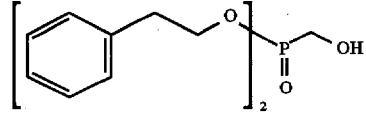

The title compound was prepared from phosphonic acid, bis-(2-phenylethyl)ester and paraformaldehyde according to the method described in Procedure 31. Purification by column chromatography on silica-gel in 2–5% methanol in dichloromethane gave the title compound as an oil.

δ(CDCl₃): 7.17–7.33 (10H, m.); 4.15–4.30 (4H, m.); 3.70–3.74 (2H, t.); 2.86–2.96 (4H, m.)

Procedure 75:

(4-Chlorobenzenesulfonyloxymethyl)phosphonic acid, bis-(2-phenylethyl)ester

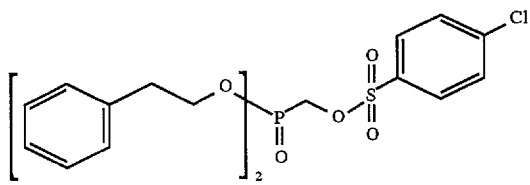

The title compound was prepared from hydroxymethylphosphonic acid, bis-(2-phenylethyl)ester and 4-chlorobenzenesulphonyl chloride according to the method described in Procedure 32. The crude product was used in the next stage without further purification.

δ(CDCl$_3$): 7.75–7.90 (2H, d.); 7.49–7.52 (2H, d.); 7.13–7.33 (10H, m.); 4.15–4.23 (4H, m.); 4.02–4.05 (2H, d.); 2.88–2.95 (4H, m.)

Procedure 76:

(S)-4-(2-t-Butoxycarbonylaminopropyl) phenoxymethyl phosphonic acid, bis-(2-phenylethyl)ester

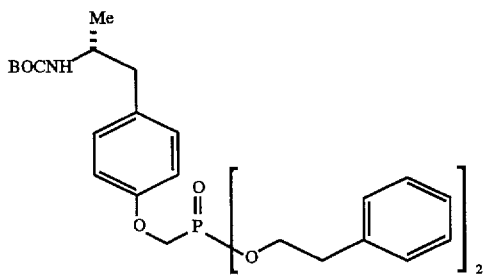

The title compound was prepared from (4-chlorobenzenesulfonyloxymethyl)phosphonic acid, bis-(2-phenylethyl)ester and (R)-2-(4-hydroxyphenyl)-1-methylethylcarbamic acid, t-butyl ester according to the method described in Procedure 24. Purification by column chromatography on silica-gel in 1–2% methanol in dichloromethane gave the title compound as a gum.

δ(CDCl$_3$): 7.19–7.27 (10H, m.); 7.07–7.17 (2H, d.); 6.78–6.81 (2H, d.); 4.26–4.30 (4H, m.); 4.03–4.06 (2H, d); 3.75–3.90 (1H, s. exchanges with D$_2$O); 2.93–2.98 (4H, t.); 2.52–2.81 (3H, complex m.); 1.43 (9H,s.); 1.05–1.07 (2H, d.).

Procedure 77:

(R)-4-(2-Aminopropyl)phenoxymethylphosphonic acid, bis-(2-phenylethyl)ester

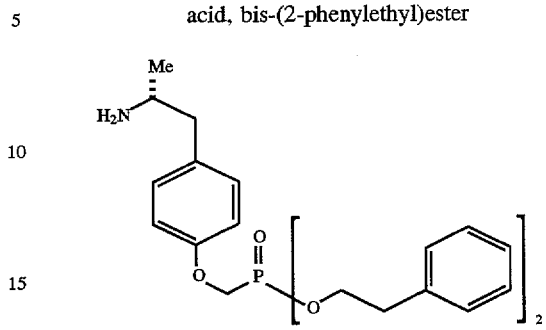

The title compound was prepared from (R)-4-(2-t-butoxycarbonyl aminopropyl)phenoxymethyl phosphonic acid, bis-(2-phenylethyl)ester according to the method described in Procedure 25. The crude product was used in the next stage without further purification.

δ(CDCl$_3$): 7.07–7.30 (12H, complex m.); 6.78–6.83 (2H, d); 4.22–4.32 (4H, m); 4.03–4.07 (2H, d.); 2.65–3.25 (9H, complex m, 2H exchange with D$_2$O); 1.17–1.20 (3H, d).

Procedure 78:

(SR)-4-{2-[3-(2,2-di-t-Butyl-4H-1,2,3-benzodioxasilinan-6-yloxy)-2-hydroxypropylamino] propyl}phenoxymethylphosphonic acid, bis-(2-phenylethyl)ester

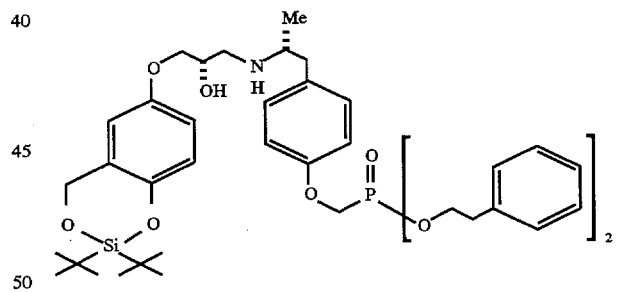

The title compound was prepared from (R)-4-(2-aminopropyl)phenoxymethyl phosphonic acid, bis-(2-phenylethyl)ester and (S)-2,2-di-t-butyl-6-(oxiran-2-ylmethoxy)-4H-1,3,2-benzodioxasilinane according to the method described in Procedure 13. The crude product was purified by chromatography on silica-gel in 1–5% methanol in dichloromethane to give the title compound as a gum.

δ(CDCl$_3$): 7.20–7.30 (10H, complex m.); 7.07–7.18 (2H, d.); 6.68–6.84 (4H, complex m.); 6.49–6.50 (1H, d.); 4.94 (2H, s.); 4.22–4.33 (4H, m.); 4.04–4.08 (2H, d.); 3.97–4.04 (1H, m.); 3.86–3.89 (2H, m.); 2.93–2.98 (4H, m.); 2.56–2.89 (3H, complex m.); 1.07–1.10 (3H, d.); 1.03 (18H, s.)

Procedure 79:

Benzylphosphinic acid, n-butyl ester

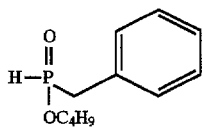

A mixture of ammonium phosphinate (9.18 g) and hexamethyldisilazane (25 mL) was heated at 110° C. for 2 hours. The mixture was cooled in ice, dissolved in dry dichloromethane (120 mL), benzyl chloride (20 g; 14 mL) was added and the mixture allowed to warm to room temperature and stirred 18 hours. The solution was filtered, the solvent evaporated, the residue azeotroped with methanol (2×70 mL), dissolved in toluene (150 mL) containing n-butanol (30 mL) and the solution was boiled under reflux in a Dean and Stark water trap for 5 hours. The solvent was evaporated, the residue slurried with dichloromethane (120 mL), filtered and evaporated and the residue chromatographed on silica-gel in 1–2% methanol in dichloromethane to give the title compound as an oil.

δ(CDCl$_3$): 8.05–6.03 (1H, d.); 7.24–7.36 (5H, complex m.); 3.88–4.15 (2H, dd.); 3.16–3.24 (2H,d.); 1.57–1.67 (2H, m.); 1.27–1.41 (2H, m.); 0.87–0.93 (3H, t.)

Procedure 80:

Benzylhydroxymethylphosphinic acid, n-butyl ester

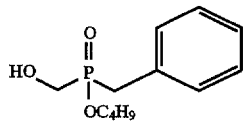

The title compound was prepared from benzylphosphinic acid, n-butyl ester and paraformaldehyde according to the method described in Procedure 31.

δ(CDCl$_3$): 7.21–7.35 (5H, s.); 3.5–4.5 (1H, s, exchanges with D$_2$O); 3.93–3.9 (2H, q.); 3.77–3.78 (2H, d.); 3.22–3.28 (2H, d.); 1.52–1.63 (2H, m.); 1.25–1.39 (2H, m.); 0.86–0.91 (3H, t.)

Procedure 81:

Benzyl(4-chlorobenzenesulfonyloxymethyl) phosphinic acid, n-butyl ester

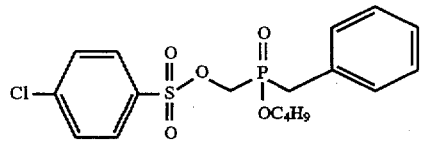

The title compound was prepared from benzylhydroxymethylphosphinic acid, n-butyl ester and 4-chlorobenzenesulfonyl chloride according to the method described in Procedure 32. The resulting white solid (mp 87°–88° C.) was used in the next stage without further purification.

δ(CDCl$_3$): 7.81–7.85 (2H, d.); 7.59–7.62 (2H, d.); 7.19–7.28 (5H, m.); 3.85–4.18 (4H, complex m.); 3.19–3.26 (2H, d.); 1.52–1.63 (2H, complex m.); 1.25–1.39 (2H, complex m.); 0.87–0.92 (3H, t.)

Procedure 82:

4-[2-(S)-(2-t-Butoxycarbonylamino)propyl] phenoxymethylbenzylphosphinic acid, n-butyl ester

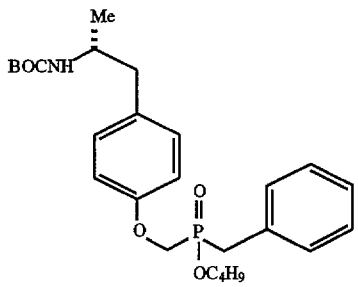

The title compound was prepared from benzyl(4-chlorobenzenesulfonyloxy methyl)phosphinic acid, n-butyl ester and (R)-2-(4-hydroxyphenyl)-1-methylethylcarbamic acid, t-butyl ester according to the procedure described in Procedure 24. The crude product was chromatographed on silica-gel in 2% methanol in dichloromethane to give a gum.

δ(CDCl$_3$): 7.21–7.29 (5H, s.); 7.09–7.13 (2H, d.); 6.83–6.87 (2H, d.); 4.0–4.11 (3H, m.); 3.30–3.38 (2H, dd.); 2.88–2.96 (2H, d.); 2.61–2.96 (2H, complex m.); 1.59–1.65 (2H, m.); 1.34–1.43 (11H, complex m.); 1.05–1.09 (3H, d.); 0.87–0.92 (3H, t.)

Procedure 83:

(R)-4-(2-Aminopropyl) phenoxymethylbenzylphosphinic acid, n-butyl ester

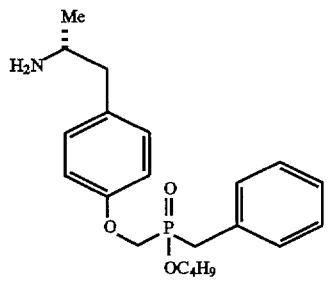

The title compound was prepared from (R)-4-[2-(2-t-butoxycarbonylamino)propyl] phenoxymethylbenzylphosphinic acid, n-butyl ester according to the method described in Procedure 25. The crude product was used in the next stage without further purification.

δ(CDCl$_3$): 7.22–7.29 (5H, s.); 7.11–7.19 (2H, d.); 6.84–6.88 (2H, d.); 3.99–4.12 (3H, complex m.); 3.30–3.38 (2H, complex m.); 3.10–3.17 (2H, complex m.); 2.44–2.70 (2H, complex m.); 1.57–1.65 (2H, complex m.); 1.23–1.44 (2H, complex m.); 1.10–1.13 (3H, d.); 0.87–0.94 (3H, t.)

Procedure 84:

(SR)-4-[2-[3-(2,2-di-t-Butyl-4H-1,3,2-benzodioxasilinan-6-yloxy)-2-hydroxypropylamino]propyl]phenoxymethylbenzylphosphinic acid, n-butyl ester

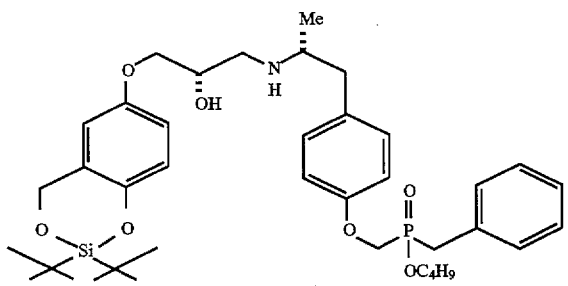

The title compound was prepared from (R)-4-(2-aminopropyl)phenoxymethyl benzylphosphinic acid n-butyl ester and (S)-2,2-di-t-butyl-6-(oxiran-2-ylmethoxy)-4H-1,3,2-benzodioxasilinane according to the procedure described in Procedure 13. The crude product was purified by chromatography on silica-gel in 2–5% methanol in dichloromethane to give a gum.

δ(CDCl$_3$): 7.26–7.28 (5H, s.); 7.10–7.13 (2H, d.); 6.65–6.86 (4H, complex m.); 6.50 (1H, d.); 4.94 (2H, s.); 4.07–4.19 (4H, complex m.); 3.89 (2H, s.); 3.27–3.35 (2H, dd.); 2.55–3.08 (4H, complex m.); 1.60–1.72 (2H, m.); 1.28–1.45 (2H, m.); 1.03–1.08 (23H, complex m.); 0.86–0.91 (3H, t.).

EXAMPLE 1

(S,R)-Sodium-4-[2-[2-hydroxy-3-(2-hydroxyphenoxy)propylamino]propyl]phenoxyacetate

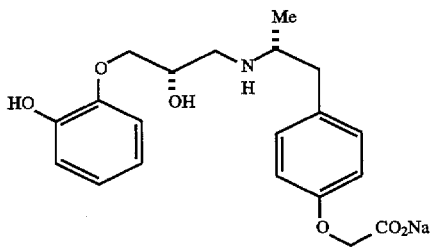

A solution of (S,R)-methyl-4-[2-[2-hydroxy-3-(2-hydroxyphenoxy)propylamino]propyl]phenoxyacetate (120 mg, 0.31 mMol) in dioxan (8 ml) and sodium hydroxide solution (2M, 5 ml) was stirred at room temperature under an argon atmosphere for 18 hours. The pH of the solution adjusted to pH9 with 2M hydrochloric acid and the solvent was evaporated. The residue was purified by reverse phase chromatography eluting with 0–5% isopropanol in water giving the title compound as a colourless solid; m.p. 130° C.; $[\alpha]_D^{25}$–13° (c=0.35, water).

δ$^1$H(270 MHz, d$^6$-DMSO/D$_2$O): 7.0–6.7 (8H, m), 4.18 (2H, s), 4.2–3.9 (3H, m), 3.1–2.8 (4H, m), 2.40 (1H, m) and 0.90 (3H, d, J=6.3 Hz) ppm.

EXAMPLE 2

(S,R)-Sodium-4-[2-[2-hydroxy-3-(3-hydroxyphenoxy)propylamino]propyl]phenoxyacetate

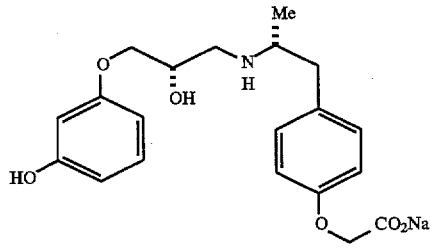

A solution of (S,R)-methyl-4-[2-[2-hydroxy-3-(3-hydroxyphenoxy)propylamino]propyl]phenoxyacetate (140 mg, 0.36 mMol) in dioxan (8 ml) and sodium hydroxide solution (2M, 5 ml) was stirred at room temperature under an argon atmosphere for 5 hours. The pH of the solution adjusted to pH9 with 2M hydrochloric acid and the solvent was evaporated. The residue was purified by reverse phase chromatography eluting with 0–5% isopropanol in water giving the title compound as a colourless solid; m.p. 136° C.; $[\alpha]_D^{25}$–11° (c=0.16, 50% isopropanol/50% water).

δ$^1$H(270 MHz, d$_6$-DMSO/D$_2$O): 7.1–6.9 (3H, m), 6.70 (2H, d, J=8.5 Hz), 6.35–6.25 (3H, m), 4.19 (2H, s), 4.0–3.7 (3H, m), 2.9–2.3 (5H, m) and 0.91 (3H, d, J=6.3 Hz) ppm.

EXAMPLE 3

(S,R)-Sodium-4-[2-[2-hydroxy-3-(4-hydroxyphenoxy)propylamino]propyl]phenoxyacetate

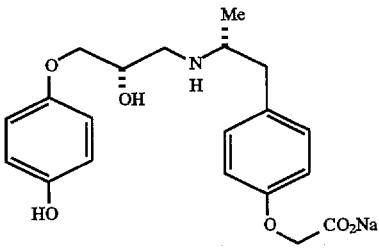

A solution of (S,R)-methyl-4-[2-[2-hydroxy-3-(4-hydroxyphenoxy)propylamino]propyl]phenoxyacetate (140 mg, 0.36 mMol) in dioxan (8 ml) and sodium hydroxide solution (2M, 5 ml) was stirred at room temperature under an argon atmosphere for 18 hours. The pH of the solution adjusted to pH9 with 2M hydrochloric acid and the solvent was evaporated. The residue was purified by reverse phase chromatography eluting with 0–20% isopropanol in water giving the title compound as a colourless solid; m.p. 119° C.; $[\alpha]_D^{25}$–15° (c=0.34, 70% isopropanol/30% water).

δ$^1$H(270 MHz, d$^6$-DMSO/D$_2$O): 6.93 (2H, d, J=8.0 Hz), 6.8–6.6 (6H, m), 4.22 (2H, s), 4.1–3.8 (3H, m), 2.95–2.75 (4H, m), 2.5–2.4 (1H, m) and 0.90 (3H, d, J=6.3 Hz) ppm.

EXAMPLE 4

(S,R)-4-{2-[2-Hydroxy-3-(4-hydroxy-3-hydroxymethylphenoxy)propylamino]propyl}phenoxymethyl phosphonic acid diethyl ester

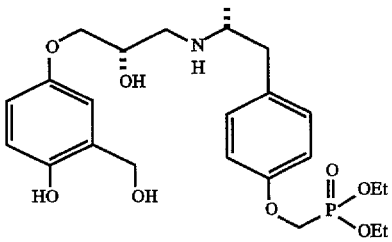

To a solution of (S,R)-4-{2-[3-(2,2-Di-tert-butyl-4H-1,3,2-benzodioxasilinan-6-yloxy)-2-hydroxypropylamine]propyl}phenoxymethyl phosphonic acid diethyl ester (270 mg, 0.424 mMol) in tetrahydrofuran (10 ml) in a plastic container at room temperature under argon was added hydrogen fluoride pyridine complex (5 drops). After 15 minutes, alumina (220 mg) was added and the stirring was continued for a further 30 minutes. The reaction mixture was filtered through a short pad of celite and the solvent evaporated in vacuo. The crude product was purified by reverse phase chromatography over C18 silica, eluting with 20% ethanol in water to give the title compound as a beige coloured foam.

$\delta^1$H (400 MHz, d$^6$-DMSO): 8.81 (s, br, exchanges with D$_2$O; 7.18 (2H, d, J=10.7 Hz); 6.95 (2H, d, J=10.7 Hz); 6.92 (1H, d, J=2.4 Hz); 6.70 (1H, d, J=9.6 Hz); 6.65 (1H, d, J=9.6 Hz and 2.4 Hz); 4.47 (2H, s); 4.40 (2H, d, J=10.7 Hz); 4.15 (4H, q, J=6.4 Hz); 4.0 (1H, m); 3.85 (2H, d, J=3.2 Hz); 2.8–3.1 (5H, m); 1.27 (6H, t, J=6.4 Hz); 1.04 (3H, d, J=7.5 Hz)

EXAMPLE 5

(S,R)-Lithium(4-{2-[2-hydroxy-3-(4-hydroxy-3-hydroxymethylphenoxy)propylamino]propyl}phenoxymethyl)ethyl phosphonate

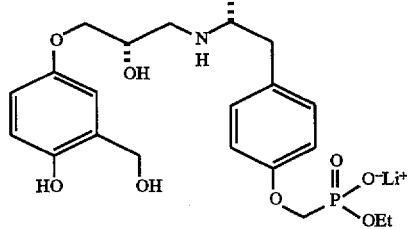

(S,R)-4-{2-[2-hydroxy-3-(4-hydroxy-3-hydroxymethylphenoxy)propylamino}propyl)phenoxymethyl phosphonic acid diethyl ester (220 mg, 0.443 mMol) and 1M lithium hydroxide (5 ml) in 1,4-dioxan (5 ml) was stirred at room temperature for 24 hours under argon. The solution was adjusted to pH 9 by addition of solid carbon dioxide, and the solvents evaporated. The residue was purified by reverse phase chromatography over C18 silica eluting with 0–10% ethanol in water to give a white powder. mpt. 120°–21° C.

$\delta^1$H (400 MHz, d$^6$-DMSO): 9.25 (s, br, exchanges with D$_2$O); 7.07 (2H, d, J=10.7 Hz); 6.9 (1H, d, J=2.0 Hz); 6.78 (2H, d, J=10.7 Hz); 6.71 (1H, d, J=10 Hz.); 6.5 (1H, d, J=10.5 Hz and 2.1 Hz); 5.2 (s, br, exchanges with D$_2$O); 4.45 (2H, s); 4.07 (1H, m); 3.8 (6H, m); 2.8–3.2 (5H, m); 1.14 (3H, t, J=6.5 Hz); 0.94 (3H, d, J=7.5 Hz)

EXAMPLE 6

(S,R)-4-{2-[2-hydroxy-3-(4-hydroxy-3-hydroxymethylphenoxy)propylamino]propyl}phenoxymethyl carboxylic acid methyl ester

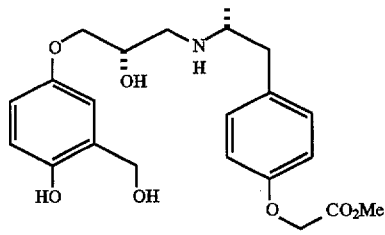

To a solution of (S,R)-4-{2-[3-2,2-di-tert-butyl-4H-1,3,2-benzodioxasilian-6-yl-oxy)-2-hydroxypropylamine]propyl}phenoxymethyl carboxylic acid methyl ester (0.262 g, 0.469 mMol) in tetrahydrofuran (10 ml) in a plastic container at room temperature under argon was added hydrogen fluoride pyridine complex (5 drops). After 10 minutes, aluminia (250 mg) was added and the stirring was continued for a further 30 minutes. The reaction mixture was filtered through a short pad of celite and the solvent evaporated in vacuo. The crude product was used in the next step.

$\delta^1$H (400 MHz, d$^6$-DMSO): 8.83 (s, br, exchanges with D$_2$O); 7.15 (2H, d, J=9.8 Hz); 6.89 (1H, d, J=2.6 Hz); 6.83 (2H, d, J=9.6 Hz); 6.66 (2H, m); 4.95 (s, br, exchanges with D$_2$O); 4.73 (2H, s); 4.46 (2H, s); 3.96 (1H, m); 3.82 (2H, m); 3.68 (3H, s); 3.30–2.75 (5H, m); 1.07 (3H, d, J=7.8 Hz)

EXAMPLE 7

(SR)Sodium-(4-{2-[2-hydroxy-3-(4-hydroxy-3-hydroxymethylphenoxy)propylamino]propyl}phenoxymethylcarboxylate

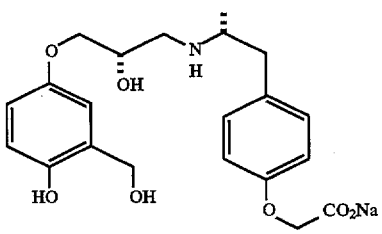

(SR)-4-{2-[2-hydroxy-3-(4-hydroxy-3-hydroxymethylphenoxy)propylamino]propyl}phenoxymethyl carboxylic acid methyl ester (0.16 g, 0.382 mMol) and 2M sodium hydroxide (5 ml) in 1,4-dioxane (5 ml) was stirred at room temperature for 20 hours under argon. The solution was adjusted to pH 9 by addition of solid carbon dioxide, and the solvents evaporated. The residue was purified by reverse phase chromatography over C$_{18}$ silica eluting with 0–20% ethanol in water to give white crystals. mpt. 140°–2° C.

$\delta^1$H(400MHz, d$^6$-DMSO): 9.0 (s, br, exchanges with D$_2$O); 6.94 (3H, m); 6.81–6.62 (4H, m); 4.48 (2H, s); 4.41 (2H, s); 4.18 (1H, m); 3.87 (2H, m); 3.25 (2H, m); 2.94 (1H, m); 2.82 (1H, m); 2.34 (1H, m); 0.94 (3H, d, J=7.5 Hz).

EXAMPLE 8

(SR)-4-{2-[2-Hydroxy-3-(4-hydroxy-3-hydroxymethylphenoxy)propylamino]propyl}phenoxyacetic acid

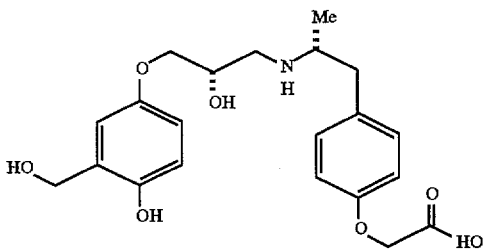

The title compound is prepared from (S,R)-4-{2-[2-hydroxy-3-(4-hydroxy-3-hydroxymethylphenoxy)propylamino]propyl}phenoxymethylphosphonic acid, methyl ester according to a modification of the procedure described in Example 7. Acidification to pH 7 with 1M hydrochloric acid followed by reverse phase chromatography and freeze drying provides the title compound.

EXAMPLE 9

(SR)-4-{2-[2-Hydroxy-3-(4-hydroxy-3-hydroxymethylphenoxy)propylamino]propyl}phenoxymethylphosphonic acid, ethyl ester

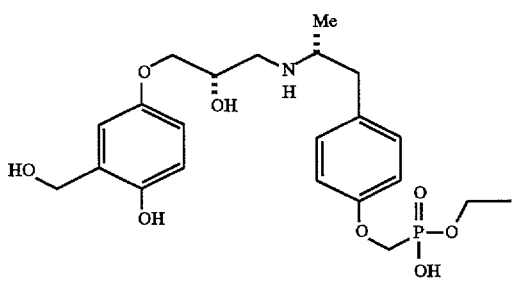

The title compound is prepared from (S,R)-4-{2-[2-hydroxy-3-(4-hydroxy-3-hydroxymethylphenoxy)propylamino]propyl}phenoxymethylphosphonic acid diethyl ester according to a modification of the procedure described in Example 5. Acidification to pH 7 with 1M dilute hydrochloric acid followed by reverse phase chromatography and freeze drying provides the title compound.

EXAMPLE 10

(SR)-4-{2-[3-(3,4-Dihydroxyphenoxy)-2-hydroxypropylamino]propyl}phenoxyacetic acid, methyl ester, hydrochloride

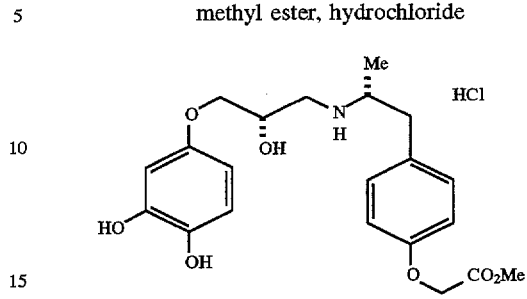

A solution of (SR)-4-{2-[3-(3,4-dibenzyloxyphenoxy)-2-hydroxypropylamino]propyl}phenoxyacetic acid, methyl ester (230 mg, 0.4 mMol) in methanol (30 ml) containing palladium(II)chloride (7 1 mg, 0.4 mMol) was hydrogenated at room temperature and pressure for 18 hours. The mixture was filtered through a pad of filter aid, the filter pad was washed with methanol and the combined filtrates were evaporated. The residue was dissolved in water and the solution was freeze dried giving the title compound as a colourless solid.

δ($D_2O$): 7.28 (2H, d, J=8.6 Hz), 6.94 (2H, d, J=8.6 Hz), 6.85 (1H, d, J=8.7 Hz), 6.51 (1H, d, J=3 Hz), 6.40 (1H, dd, J=8.7, 3 Hz), 4.72 (2H, s), 4.3–4.25 (1H, m), 4.05–3.97 (2H, m), 3.82 (3H, s), 3.68 (1H, dd, J=13.8, 6.9 Hz), 3.4–3.36 (2H, m), 3.05 (1H, dd, J=13.1, 7 Hz), 2.94 (1H, dd, J=13.8, 7.6 Hz), 1.34 (3H, d, J=6.6 Hz).

EXAMPLE 11

(SR)-4-{2-[3-(3,4-Dihydroxyphenoxy)-2-hydroxypropylamino]propyl}phenoxyacetic acid, hydrochloride

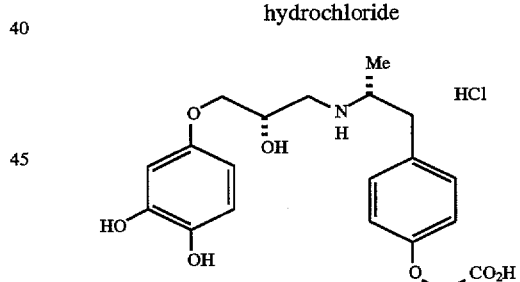

A solution of (SR)-4-{2-[2-hydroxy-3-(3,4-dihydroxyphenoxy)propylamino]propyl}phenoxyacetic acid, methyl ester, hydrochloride (78 mg, 0.17 mMol) in water (2 ml) containing hydrochloric acid (1M, 0.5 ml, 0.51 mMol) was heated at 100° C. under argon for 3 hours. After cooling to room temperature the solution was freeze dried giving the title compound as a colourless solid.

δ($d^6$-DMSO+$D_2O$): 7.16 (2H, d, J=8.6 Hz), 6.86 (2H, d, J=8.6 Hz), 6.64 (1H, d, J=8.5 Hz), 6.42 (1H, d, J=3 Hz), 6.21 (1H, dd, J=8.5, 3 Hz), 4.65 (2H, s), 4.25 (1H, m), 3.9–3.8 (2H, m), 3.5 (1H, m), 3.3–3.2 (2H, m), 3.05 (1H, dd, J=12.5, 9.7 Hz), 2.60 (1H, dd, J=12.5, 11 Hz), 1.10 (3H, d, J=6.3 Hz).

EXAMPLE 12

(SR)-5-{2-[3-(4-Hydroxy-3-hydroxymethylphenoxy)-2-hydroxypropylamino]propyl}-1,3-benzodioxole-2,2-dicarboxylic acid, diethyl ester

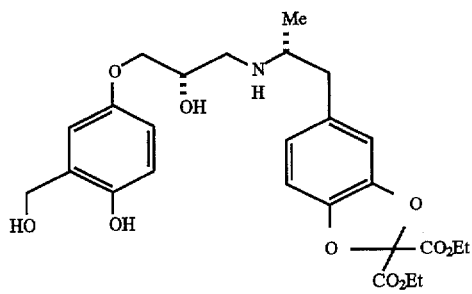

The title compound was prepared from (SR)-5-{2-[3-(2,2-di-t-butyl-4H-1,3,2-benzodioxasilinan-6-yloxy)-2-hydroxypropylamino]propyl}-1,3-benzodioxole-2,2-dicarboxylic acid, diethyl ester according to the procedure described in Example 4.

δ(d⁶-DMSO+D₂O): 7.1–6.6 (6H, m), 4.44 (2H, s), 4.32 (4H, q, J=7 Hz), 4.1–3.8 (3H, m), 3.2–2.6 (5H, m), 1.24 (6H, t, J=7 Hz), 1.02 (3H, d, J=6.5 Hz).

EXAMPLE 13

(SR)-5-{2-[3-(4-Hydroxy-3-hydroxymethylphenoxy)-2-hydroxypropylamino]propyl}-1,3-benzodioxole-2,2-dicarboxylic acid, dilithium salt

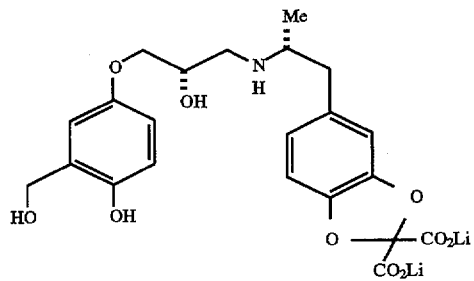

A solution of (SR)-5-{2-[3-(4-Hydroxy-3-hydroxymethylphenoxy)-2-hydroxypropylamino]propyl}-1,3-benzodioxole-2,2-dicarboxylic acid, diethyl ester (520 mg, mMol) in dioxan (10 ml), water (3 ml) and lithium hydroxide solution (1M, 6 ml, 6 mMol) was stirred at room temperature under argon for 24 hours. The pH of the solution was adjusted to 9 with dilute hydrochloric acid and the solvent was evaporated. The residue was purified by reverse phase chromatography eluting with water-methanol mixtures to give the title compound as a colourless solid.

δ(d⁶-DMSO+D₂O): 6.90 (1H, d, J=2.2 Hz), 6.76–6.58 (4H, m), 6.49 (1H, d, J=7.7 Hz), 4.42 (2H, s), 4.1–4.0 (1H, m), 3.84–3.81 (2H, m), 3.2–2.8 (4H, m), 2.45–2.38 (1H, m), 0.98 (3H, d, J=6.3 Hz).

EXAMPLE 14

(S)-4-{2-[2-Hydroxy-3-(4-hydroxy-3-hydroxymethylphenoxy)propylamino]ethyl}phenoxymethylphosphonic acid, diethyl ester

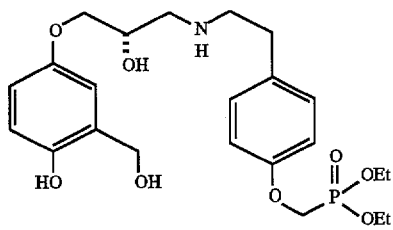

The title compound was prepared from (S)-4-{2-[3-(2,2-di-t-butyl-4H-1,3,2-benzodioxasilinan-6-yl-oxy)-2-hydroxypropylamino]ethyl}phenoxymethyl phosphonic acid, diethyl ester using an experimental procedure similar to that described in Example 4. The title compound was prepared and isolated as a white foam.

δ¹H (200 MHz, d⁶-DMSO): 7.20 (2H, br d), 6.95 (3H, m), 6.67 (2H, m), 5.10 (1H, br t), 4.45 (4H, m), 4.15 (7H, m), 3.88 (2H, m), 2.8–3.2 (4H, m), 1.25 (6H, t, J=6.5 Hz)

EXAMPLE 15

(S)-4-{2-[2-Hydroxy-3-(4-hydroxy-3-hydroxymethylphenoxy)propylamino]ethyl}phenoxymethylphosphonate, ethyl ester, mono lithium salt

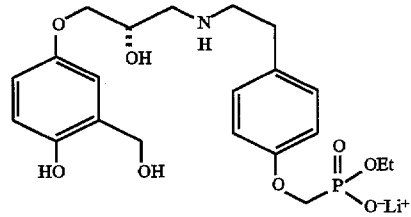

The title compound was prepared from (S)-4-{2-[2-hydroxy-3-(4-hydroxy-3-hydroxymethylphenoxy)propylamino]ethyl}phenoxymethyl phosphonic acid, diethyl ester using a procedure similar to that employed for Example 5 and isolated as a solid after freeze drying.

δ¹H (250 MHz, d₆-DMSO): 7.0 (2H, d, J=8 Hz), 6.70 (4H, m), 6.25 (1H, dd, J=8 Hz and 2.3 Hz), 4.42 (2H, s), 4.20 (1H, br s), 3.75 (5H, m); 3.55 (1H, m), 2.4–2.8 (5H, m), 0.95 (3H, t, J=6.7 Hz)

EXAMPLE 16

(SR)-4-{2-[2-Hydroxy-3-(4-hydroxy-3-hydroxymethylphenoxy)propylamino]propyl}phenoxymethylphosphonic acid, bis-(3-benzyloxypropyl)ester

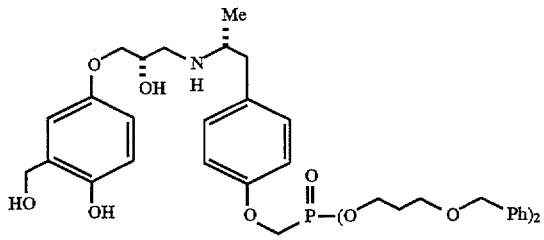

(SR)-4-{2-[3-(2,2-Di-t-butyl-4H-1,3,2-benzodioxasilinan-6-yl-oxy)-2-hydroxypropylamino]propyl}phenoxymethylphosphonic acid, bis-(3-benzyloxypropyl)ester (0.49 g, 0.56 mMol) was converted into the title compound by a method similar to Example 4.

δ¹H (250 MHz, CDCl₃): 7.25 (10H, m), 7.05 (2H, d), 6.73 (2H, d), 6.62 (1H, d), 6.55–6.35 (2H,m), 4.50 (2H, br), 4.42 (4H, s), 4.30–4.00 (8H, m,), 3.70 (2H, 3.58–3.30 (5H, m), 3.30–2.85 (3H, overlapping br.), 2.71 (1H, br), 1.92 (4H, m), 1.18 (3H, d).

EXAMPLE 17

(SR)-4-{2-[2-Hydroxy-3-(4-hydroxy-3-hydroxymethylphenoxy)propylamino]propyl}phenoxymethylphosphonic acid, (3-benzyloxypropyl)ester, lithium salt

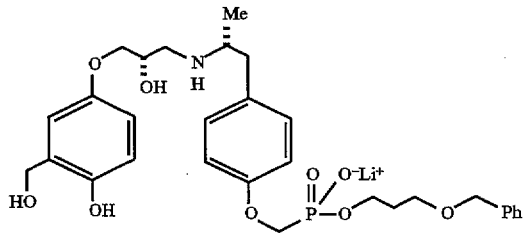

The title compound was prepared by a similar method to that of Example 5 from (SR)-4-{2-[2-hydroxy-3-(4-hydroxy-3-hydroxymethyl-phenoxy)propylamino]-2-propyl}phenoxymethylphosphonic acid, bis-(3-benzyloxypropyl)ester (0.314 g, 0.43 mMol).

δ¹H (400 MHz, CD₃OD): 7.15 (5H, m), 6.97 (2H, d), 6.74 (3H, m), 6.55 (1H, d), 6.48 (1H, dd), 4.49 (2H, s), 4.29 (2H, s), 4.00–3.80 (5H, m), 3.71 (2H, m), 3.47 (2H, t), 2.82–2.54 (4H, m), 2.42 (1H, dd), 1.78 (2H, m), 0.92 (3H, d).

EXAMPLE 18

(SR)-4-{2-[2-Hydroxy-3-(4-hydroxy-3-hydroxymethylphenoxy)propylamino]propyl}phenoxymethylphosphonic acid, bis-(3-hydroxypropyl)ester

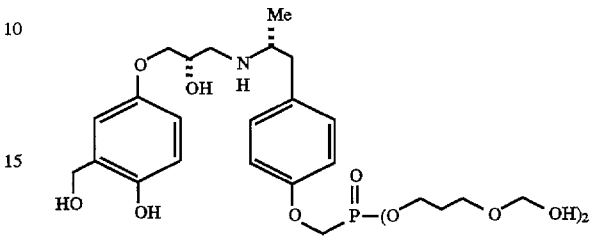

The title compound was prepared from (SR)-4-{2,2-di-t-butyl-4H-1,3,2-benzodioxasilinan-6-yl-oxy)-2-hydroxypropylamino]propyl}phenoxymethylphosphonic acid, bis-(3-hydroxypropyl)ester (0.248 g, 0.36 mMol) by a method similar to that of Example 4.

δ¹H (200 MHz, CD₃OD): 7.25 (2H, d), 7.10–6.90 (3H, m), 6.71 (2H, m), 4.64 (2H, s), 4.42 (2H, d), 4.30 (5H, m), 3.97 (2H, m), 3.68 (4H, t), 3.54 (1H, m), 3.25 (3H, m), 2.74 (1H, m), 1.91 (4H, m), 1.24 (3H, d).

EXAMPLE 19

(SR)-4-{2-[2-Hydroxy-3-(4-hydroxy-3-hydroxymethylphenoxy)propylamino]propyl}phenoxymethylphosphonic acid, mono-(3-hydroxypropyl)ester, lithium salt

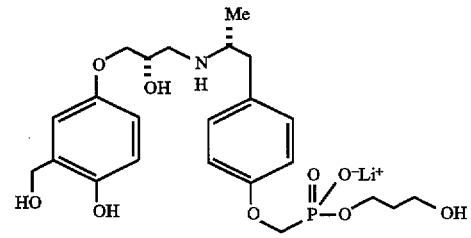

The title compound was obtained by hydrolysis of (SR)-4-{2-[2-hydroxy-3-(4-hydroxy-3-hydroxymethylphenoxy)propylamino]propyl}phenoxy-methyl)phosphonic acid, bis-(3-hydroxypropyl)ester (0.198 g, 0.356 mMol) using a method similar to that of Example 5.

δ¹H (250 MHz, CD₃OD): 7.11 (2H, d), 6.90 (3H, m), 6.70 (1H, d), 6.60 (1H, dd), 4.62 (2H, s), 4.15–3.92 (5H, m) 3.85 (2H, d), 3.69 (2H, t), 3.05–2.68 (4H, m), 2.57 (1H, dd), 1.83 (2H, m), 1.08 (3H, d).

EXAMPLE 20

(SR)-4-{2-[2-Hydroxy-3-(4-hydroxy-3-hydroxymethylphenoxy)propylamino]propyl}phenoxymethylphenylphosphinic acid, ethyl ester

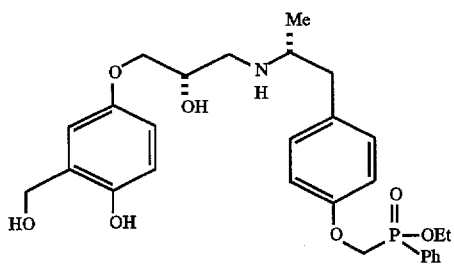

The title compound was prepared from (SR)-{2-[3-(2,2-di-t-butyl-4H-1,3,2-benzodioxasilinan-6-yl-oxy)-2-hydroxypropylamino]propyl}phenoxymethylphenylphosphinic acid, ethyl ester (0.906 g, 1.35 mMol) by a method similar to that of Example 4 and was obtained as a colourless gum.

m/z: FAB MH⁺ 530 (14%)

EXAMPLE 21

(SR)-4-{2-[2-Hydroxy-3-(4-hydroxy-3-hydroxymethylphenoxy)propylamino]propyl}phenoxymethyl-phenylphosphinic acid, lithium salt

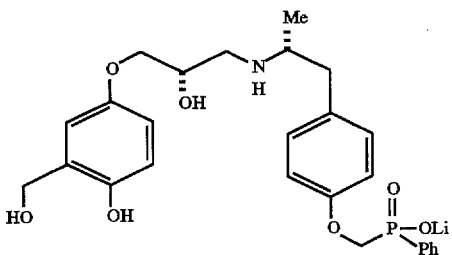

The title compound was prepared as a white foam after freeze-drying, from (SR)-4-{2-[4-hydroxy-3-(4-hydroxy-3-hydroxymethylphenoxy)propyl amino]propyl}phenoxymethylphenylphosphinic acid, ethyl ester (0.715 g, 1.35 mMol) by a method similar to that of Example 5, except that methanol was used as co-solvent instead of 1,4-dioxan.

$\delta^1$H (250 MHz, CD₃OD): 7.89 (2H, m), 7.40 (3H, m), 7.08 (2H, d), 6.91 (1H, d), 6.84 (2H, d), 6.70 (1H,d), 6.64 (1H, dd), 4.62 (2H, s), 4.20–4.00 (3H, m), 3.91 (2H, m), 3.37–2.85 (4H, m), 2.62 (1H, dd), 1.15 (3H, d).

EXAMPLE 22

(S)-4-{2-[2-Hydroxy-3-(4-hydroxy-3-hydroxymethylphenoxy)propylamino]ethyl}phenoxymethyl-(3-benzyloxypropyl)phosphinic acid, n-butyl ester

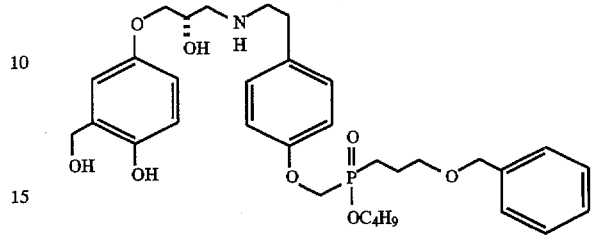

The title compound was prepared from (S)-4-{2-[3-(2,2-di-t-butyl-4H-1,3,2-benzodioxasilinan-6-yloxy)-2-hydroxypropylamino]ethyl}phenoxymethyl-(3-benzyloxypropyl)phosphinic acid, n-butyl ester according to the procedure described in Example 4, the crude product was used without further purification.

δ(d⁶-DMSO+D₂O): 7.43–7.28(5H, m.); 7.27(2H, d, J=8.86 Hz); 7.04(2H, d, J=8.80 Hz.); 6.99(1H, d, J=2.20 Hz.); 6.74–6.71 (2H, m.); 4.53(2H, s.); 4.44–4.42(2H, m.); 4.40–3.91(7H, m.); 3.56(2H, t, J=6.05 Hz.); 3.25–2.90(6H, m.); 1.93–1.79(4H, m.); 1.66–1.61(2H, m.); 1.44–1.39(2H, m.); 0.94(3H, t, J=7.41 Hz.).

EXAMPLE 23

(S)-4-{2-[2-Hydroxy-3-(4-hydroxy-3-hydroxymethylphenoxy)propylamino]ethyl}phenoxymethyl-(3-benzyloxypropyl)phosphinic acid

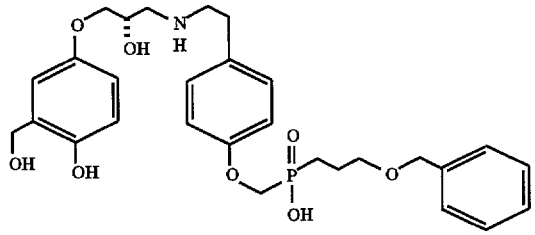

The title compound was prepared from (S)-4-{2-[2-hydroxy-3-(4-hydroxy-3-hydroxymethyl-phenoxy)propylamino]ethyl}phenoxymethyl-(3-benzyloxypropyl)phosphinic acid, n-butyl ester according to a modification of the procedure described in Example 5. Acidification to pH 3.5 with 1M hydrochloric acid followed by C18 reverse phase chromatography, eluting with water-methanol (30%) and freeze drying of the resultant foam gave the title compound as a solid.

δ(d⁶-DMSO+D₂O) 7.31–7.21(5H, m.); 7.06(2H, d, J=8.40 Hz.); 6.88(1H, d, J=2.97 Hz.); 6.81(2H, d, J=8.40 Hz.); 6.66(1H, d, J=8.65 Hz.); 6.59(1H, dd, J=8.68, 2.99 Hz.); 4.42(2H, s.); 4.38(2H, s.); 4.12–4.09(1H, m.); 3.87–3.70(2H, m.); 3.72(2H, d, J=8.00 Hz.) 3.38(2H, t, J=6.57 Hz.); 3.40–2.95(4H, m.); 2.84–2.82(2H, m.); 1.73–1.67(2H, m.); 1.46–1.38(2H, m.).

EXAMPLE 24

(SR)-4-{2-[2-Hydroxy-3-(4-hydroxy-3-hydroxymethylphenoxy)propylamino]propyl}phenoxymethyl(3-benzyloxypropyl) phosphinic acid, n-butyl ester

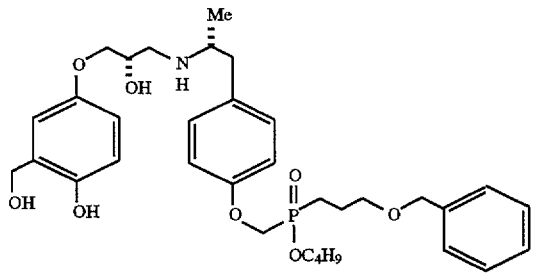

The title compound was prepared from (SR)-4-{2-[3-(2,2-di-t-butyl-4H-1,3,2-benzodioxasilinan-6-yloxy)-2-hydroxypropylamino]propyl}phenoxymethyl-(3-benzyloxypropyl)phosphinic acid, n-butyl ester according to the procedure described in Example 4. The crude product was used without further purification.

δ(CDCl$_3$+CD$_3$OD): 7.44–7.30(5H, m.); 7.17(2H, d, J=8.53 Hz.); 6.82(2H, d, J=8.57 Hz.); 6.76–6.68(2H, m.); 6.65–6.59(1H, m.); 4.75(2H, s.); 4.51(2H, s.); 4.20–3.86 (7H, m.); 3.55(2H, t, J=5.77 Hz.); 3.28–3.09(4H, m.); 2.81–2.73(1H, m); 2.12–1.91(4H, m.); 1.75–1.55(2H, m.); 1.48–1.37(2H, m.); 1.24(3H, d, J=5.50 Hz.); 0.91(3H, t, J=7.15 Hz.);

EXAMPLE 25

(SR)-4-{2-[2-Hydroxy-3-(4-hydroxy-3-hydroxymethylphenoxy)propylamino]propyl}phenoxymethyl(3-benzyloxypropyl) phosphinic acid, hydrochloride salt

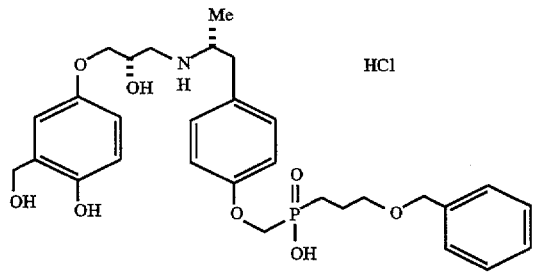

The title compound was prepared from (SR)-4-{2-[2-hydroxy-3-(4-hydroxy-3-hydroxymethylphenoxy)propylamino]propyl}phenoxymethyl(3-benzyloxypropyl) phosphinic acid, n-butyl ester according to a modification of the procedure described in Example 5. Acidification to pH 3.5 with 1M hydrochloric acid followed by C18 reverse phase chromatography, eluting with water-methanol (30%) and freeze drying of the resultant foam gave the title compound as a solid.

δ(d$^6$-DMSO+D$_2$O): 7.33–7.23(5H, m.); 7.00(2H, d, J=8.31 Hz.); 6.81(1H, d, J=2.94 Hz.); 6.75(2H, d, J=8.32 Hz.); 6.70(1H, d, J=8.62 Hz.); 6.28(1H, dd, J=8.52, 2.69 Hz.); 4.46(2H, s.); 4.41(2H, s.); 3.73–3.66(5H, m.); 3.42 (2H, t, J=6.58 Hz.); 2.88–2.72(2H, m.); 2.67–2.52 (3H ,m). 1.79–1.69(2H. m.); 1.45–1.37(2H, m); 0.97(3H, d, J=6.12 Hz.).

EXAMPLE 26

(S)-{2-[2-Hydroxy-3-(4-hydroxy-3-hydroxymethylphenoxy)propylamino]ethyl}phenoxymethylcyclohexylphosphinic acid, n-butyl ester

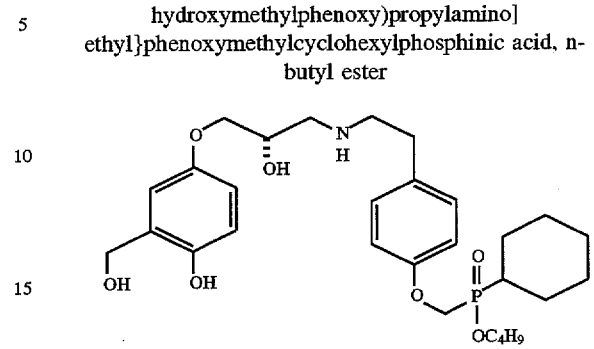

The title compound was prepared from (S)-4-{2-[3-(2,2-di-t-butyl-4H-1,3,2-benzodioxasilinan-6-yloxy)-2-hydroxypropylamino]ethyl}phenoxymethyl cyclohexylphosphinic acid, n-butyl ester according to the procedure described in Example 4. The crude product was used without further purification δ(d$^6$-DMSO+D$_2$O): 7.18(2H, d, J=8.25 Hz.); 6.96(2H, d, J=8.52 Hz.); 6.89(1H, s.); 6.70–6.66(2H, m.); 4.45(2H, s.); 4.31(2H, d, J=6.87 Hz); 4.05–3.88(2H, m.); 3.78(D$_2$O obscuring 1H signal), 2.87–2.77(3H, m.); 2.54–2.52(3H, m.); 2.00–1.04(15H, m.); 0.86(3H, t, J=7.43 Hz.).

EXAMPLE 27

(S)-4-{2-[2-Hydroxy-3-(4-hydroxy-3-hydroxymethylphenoxy)propylamino]ethyl}phenoxymethylcyclohexyl phosphinic acid, lithium salt

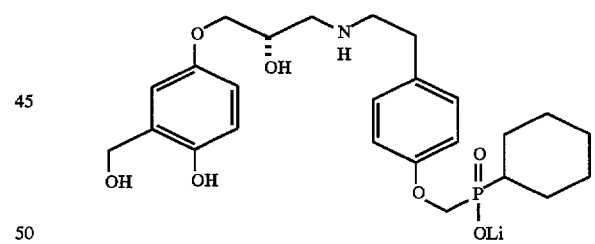

The title compound was prepared from (S)-4-{2-[2-hydroxy-3-(4-hydroxy-3-hydroxymethyl-phenoxy)propylamino]ethyl}phenoxymethyl cyclohexylphosphinic acid, n-butyl ester according the procedure described in Example 5 as a solid after C18 reverse phase chromatography, eluting with water-methanol (30%), and freeze drying of the resultant foam.

δ(CD$_3$OD): 7.24(2H, d, J=8.56 Hz.); 7.01(2H, d, J=8.56 Hz.); 6.90(1H, d, J=3.09 Hz.); 6.78(1H, dd, J=8.76, 3.16 Hz.); 6.70(1H, d, J=8.75 Hz.); 4.62(2H, s.); 4.04(2H, s.); 4.09–4.00(1H, m); 3.97(1H, dd, J=10.45, 6.70 Hz.); 3.90 (1H, dd, J=10.46, 6.24 Hz.); 2.91–2.71(6H, m.); 1.92–1.65 (6H, m.); 1.33–1.15(5H, m.).

EXAMPLE 28

(S)-4-{2-[2-Hydroxy-3-(4-hydroxyphenoxy)
propylamino]
ethyl}phenoxymethylcyclohexylphosphinic acid, n-butyl ester

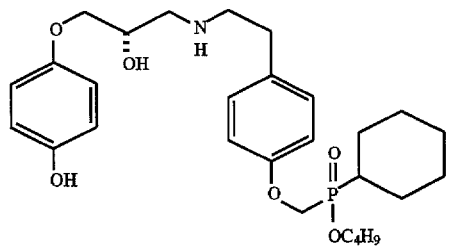

A solution of (S)-4-{2-[2-hydroxy-3-(4-benzyloxyphenoxy)propylamino]ethyl}phenoxymethylcyclohexylphosphinic acid, n-butyl ester (1.00 g, 1.64 mMol) in methanol (100 ml) containing 10% palladium on charcoal (50 mg) was hydrogenated at 40° C. and 40 p.s.i. for 24 hours. After cooling to room temperature the suspension was filtered through a pad of filter aid and the filtrate was evaporated giving the title compound.

δ(d$^6$-DMSO+D$_2$O): 7.14 (2H, d, J=8.8 Hz), 6.93 (2H, d, J=8.8 Hz), 6.73 (2H, d J=9 Hz), 6.66 (2H, d, J=9 Hz), 4.31 (2H, d, J=7.2 Hz), 4.1–3.7 (5H, m), 2.8–2.55 (6H, m), 2.0–1.2 (15H, m), 0.86 (3H, t, J=7.2 Hz).

EXAMPLE 29

(S)-4-{2-[2-Hydroxy-3-(4-hydroxyphenoxy)
propylamino]
ethyl}phenoxymethylcyclohexylphosphinic acid,
lithium salt

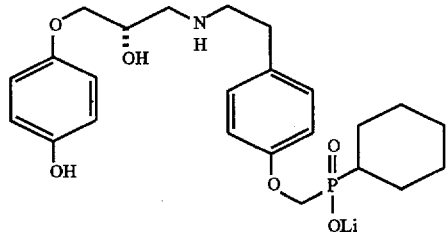

The title compound was prepared from (S)-4-{2-[2-hydroxy-3-(4-hydroxyphenoxy)propylamino]ethyl}phenoxymethylcyclohexylphosphinic acid, n-butyl ester according to the procedure described in Example 5.

δ(d$^6$-DMSO+D$_2$O): 7.07 (2H, d, J=8.5 Hz), 6.81 (2H, d, J=8.5 Hz), 6.67 (2H, d, J=9.1 Hz), 6.60 (2H, d, J=9.1 Hz), 3.85–3.6 (5H, m), 2.8–2.5 (6H, m), 1.95–1.0 (11H, m).

EXAMPLE 30

(S)-4-[2-[2-Hydroxy-3-(3-hydroxyphenoxy)
propylamino]
ethyl}phenoxymethylcyclohexylphosphinic acid, n-butyl ester

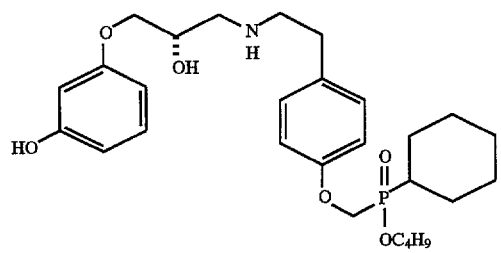

The title compound was prepared from (S)-4-{2-[2-hydroxy-3-(3-benzyloxyphenoxy)propylamino]ethyl}phenoxymethylcyclohexylphosphinic acid, n-butyl ester according to the procedure described in Example 28.

δ(d$^6$-DMSO+D$_2$O): 7.19 (2H, d, J=8.5 Hz), 7.05–6.98 (3H, m), 6.4–6.35 (3H, m), 4.33 (2H, d, J=6.9 Hz), 4.0–3.88 (5H, m), 3.25–2.8 (6H, m), 2.0–1.2 (15H, m), 0.87 (3H, t, J=6.4 Hz).

EXAMPLE 31

(S)4-{2-[2-Hydroxy-3-(3-hydroxyphenoxy)
propylamino]
ethyl}phenoxymethylcyclohexylphosphinic acid,
lithium salt

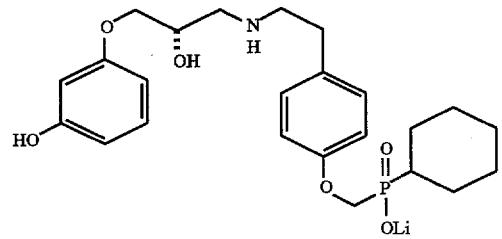

The title compound was prepared from (S)-4-{2-[2-hydroxy-3-(3-hydroxyphenoxy)propylamino]ethyl}phenoxymethylcyclohexylphosphinic acid, n-butyl ester according to the procedure described in Example 5.

δ(d$^6$-DMSO+D$_2$O): 7.01 (2H, d, J=8.5 Hz), 6.98 (1 H, t, J=8 Hz), 6.78 (2H, d, J=8.5 Hz), 6.48 (1H, d, J=2.2 Hz), 6.3–6.25 (2H, m), 4.0–3.75 (5H, m), 2.85–2.55 (6H, m), 1.9–1.0 (11 H, m).

EXAMPLE 32

(SR)-4-{2-[2-Hydroxy-3-(4-hydroxy-3-hydroxymethylphenoxy)propylamino]propyl}phenoxymethylcyclohexylphosphinic acid, n-butyl ester

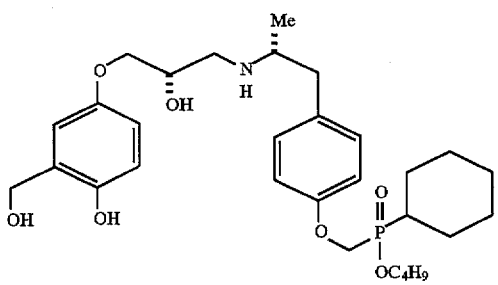

The title compound was prepared from (SR)-4-{2-[3-(2,2-di-t-butyl-4H-1,3,2-benzodioxasilinan-6-yloxy)-2-hydroxypropylamino]propyl}phenoxymethyl cyclohexylphosphinic acid, n-butyl ester according to the procedure described in Example 4. The crude product was used without further purification.

δ(CDCl$_3$+D$_2$O): 7.19(2H, d, J=8.80 Hz.); 6.90(2H, d, J=8.52 Hz.); 6.78(1H, d, J=2.74 Hz.); 6.72(1H, d, J=8.80 Hz.); 6.65(1H, dd, J=8.80, 2.75 Hz.); 4.68(2H, s.); 4.17(2H, d, J=11.82 Hz.); 4.13–3.91(3H, m.): 3.48–3.42(1H, m.); 3.24(2H, d, J=14.03 Hz.); 3.10(1H, t, J=9.90 Hz.); 2.72(1H, t, J=10.17 Hz.); 2.01–1.06(15H, m.); 1.25(3H, d, J=6.33 Hz.); 0.93(3H, t, J=7.15 Hz.).

EXAMPLE 33

(SR)-4-{2-[2-Hydroxy-3-(4-hydroxy-3-hydroxymethylphenoxy)propylamino]propyl}phenoxymethylcyclohexylphosphinic acid, lithium salt

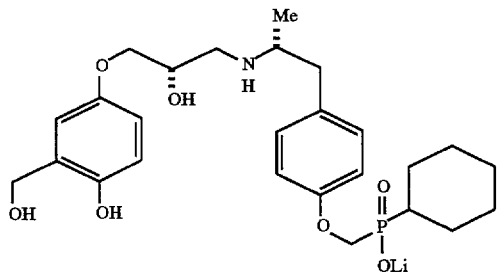

The title compound was prepared from (SR)-4{2-[2-hydroxy-3-[(4-hydroxy-3-hydroxymethylphenoxy)propylamino]propyl}phenoxymethylcyclo hexylphosphinic acid, n-butyl ester according the procedure described in Example 5 as a solid after C18 reverse phase chromatography, eluting with water methanol (30%), and freeze drying of the resultant foam.

δ(D$_2$O): 7.20(2H, d, J=8.56 Hz.); 6.96(2H, d, J=8.64 Hz.); 6.91(1H, d, J=5.37 Hz.); 6.80(1H, d, J=8.76 Hz.); 6.75(1H, dd, J=8.75, 5.15 Hz.); 4.63(2H, s.); 4.08–3.86(3H, m.); 4.01(2H, d, J=7.55 Hz.); 3.04–2.98(5H, m.); 1.87–1.67(7H, m.); 1.29–1.14(4H, m.); 1.09(3H, t, J=6.17 Hz.).

EXAMPLE 34

(SR)-4-{2-[2-Hydroxy-3-(4-hydroxy-3-hydroxymethylphenoxy)propylamino]propyl}phenoxymethyl-n-hexyl phosphinic acid, n-butyl ester

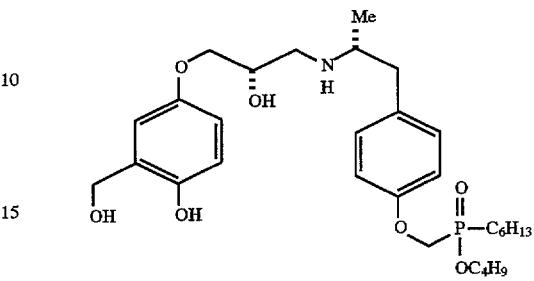

The title compound was prepared from (SR)-4-{2-[3-(2,2-di-t-butyl-4H-1,3,2-benzodioxasilinan-6-yloxy)-2-hydroxypropylamino]propyl}phenoxy-methyl-n-hexylphosphinic acid, n-butyl ester according to the procedure described in Example 4. The crude product was used without further purification.

δ(d$^6$-DMSO+D$_2$O): 7.15(2H, d, J=8.50 Hz.); 6.94(2H, d, J=8.63 Hz.); 6.9(1H, d, J=2.84 Hz.); 6.68(1H, d, J=8.61 Hz.); 6.63(1H, dd, J=8.68, 2.97 Hz.); 4.45(2H, s.); 4.35–4.28 (2H, m.); 4.05–3.90(4H, m.); 3.86–3.81(1H, m.); 2.97–2.90 (1H, m.); 2.89(3H, m.); 2.50–2.45(1H, m.); 1.86–1.79(2H, m.); 1.59–1.48(4H, m.); 1.38–1.21(8H, m.); 0.97(3H, d, J=6.25 Hz.); 0.86(3H, t, J=7.28 Hz.); 0.84(3H, t, J=6.87 Hz.).

EXAMPLE 35

(SR)-4-{2-[2-Hydroxy-3-(4-hydroxy-3-hydroxymethylphenoxy)propylamino]propyl}phenoxymethyl-n-hexylphosphinic acid, lithium salt

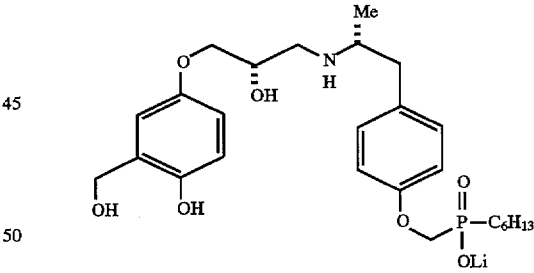

The title compound was prepared from (SR)-4-{2-[2-hydroxy-3-(4-hydroxy-3-hydroxymethylphenoxy)propylamino]propyl}phenoxymethyl-n-hexyl phosphinic acid, n-butyl ester according the procedure described in Example 5 as a solid after C18 reverse phase chromatography, eluting with water-methanol (30%), and freeze drying of the resultant foam δ(d$^6$-DMSO+D$_2$O): 7.09(2H, d, J=8.48 Hz.); 6.85(2H, d, J=8.45 Hz.); 6.89(1H, d, J=3.00 Hz.); 6.68(1H, d, J=8.62 Hz.); 6.52(1H, dd, J=8.62, 3.00 Hz.); 4.47(2H, s.); 3.84(1H, t, J=5.32 Hz.); 3.82–3.73(4H, m.); 2.81–2.73(2H, m.) 2.71–2.61(2H, m.); 2.52–2.43(1H, m.); 1.44–1.41(4H, m.); 1.28–1.15(6H, m.); 0.95(3H, d, J=6.24 Hz.); 0.81(3H, t, J=6.70 Hz.).

EXAMPLE 36

(S)-4-{2-[2-Hydroxy-3-(4-hydroxyphenoxy)propylamino]ethyl}phenoxymethyl-n-hexylphosphinic acid, n-butyl ester

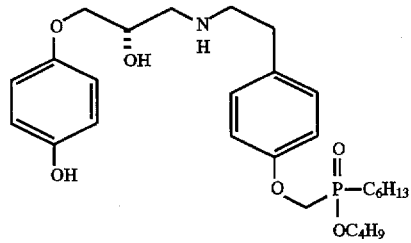

The title compound was prepared from (S)-N-benzyl-4-{2-[2-hydroxy-3-(4-benzyloxyphenoxy)propylamino]ethyl}phenoxymethyl-n-hexylphosphinic acid, n-butyl ester according to the procedure described in Example 28.

$\delta(d^6\text{-DMSO}+D_2O)$: 7.14 (2H, d, J=8.5 Hz), 6.92 (2H, d, J=8.5 Hz), 6.74 (2H, d, J=8.6 Hz), 6.66 (2H, d, J=8.6 Hz), 4.35–3.75 (7H, m), 2.75–2.6 (6H, m), 1.85–1.75 (2H, m), 1.6–1.45 (4H, m), 1.4–1.25 (8H, m), 0.9–0.8 (6H, m).

EXAMPLE 37

(S)4-{2-[2-Hydroxy-3-(4-hydroxyphenoxy)propylamino]ethyl}phenoxymethyl-n-hexylphosphinic acid

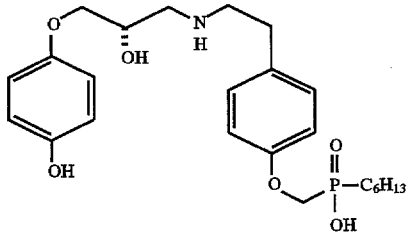

The title compound was prepared from (S)-4-{2-[2-hydroxy-3-(4-hydroxyphenoxy)propylamino]ethyl}phenoxymethyl-n-hexyl phosphinic acid, n-butyl ester according a modification of the procedure described in Example 25. Acidification to pH 6 with 1M hydrochloric acid followed by C18 reverse phase chromatography and freeze drying gave the title compound as a solid.

$\delta(d^6\text{-DMSO}+D_2O)$: 7.05 (2H, d, J=8.5 Hz), 6.79 (2H, d, J=8.5 Hz), 6.65 (4H, b), 3.9–3.7 (5H. m), 2.85–2.65 (6H, m), 1.4 (4H, m), 1.2 (6H, m), 0.80 (3H, t, J=7.0 Hz).

EXAMPLE 38

(SR)-4-{2-[2-Hydroxy-3-(4-hydroxy-3-hydroxymethylphenoxy)propylamino]propyl}phenoxymethylphosphonic acid, bis-(2-phenylethyl)ester

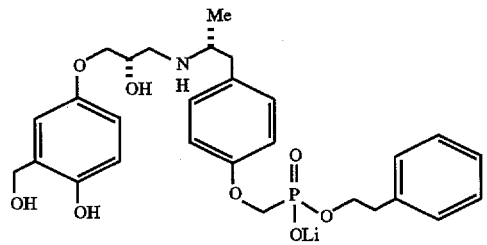

The title compound was prepared from (R)-4-{2-[3-(2,2-di-t-butyl-4H-1,2,3-benzodioxasilinan-6-yloxy)-2-(S)-hydroxypropylamino]propyl}phenoxy methylphosphonic acid, bis-(2-phenylethyl)ester according to the procedure described in Example 4. The crude product was used in the next stage without further purification.

EXAMPLE 39

(SR)-4-{2-[2-Hydroxy-3-(4-hydroxy-3-hydroxymethylphenoxy)propylamino]propyl}phenoxymethylphosphonic acid, 2-phenylethyl ester, lithium salt The title compound was prepared from (SR)-4-{2-[2-hydroxy-3-(4-hydroxy-3-hydroxymethylphenoxy)propylamino]propyl}phenoxymethylphosphonic acid, bis-(2-phenylethyl)ester according to the method described in Example 5 as a solid following chromatography on C18 reverse phase silica-gel, eluting with 40% methanol-water, and freeze drying of the resultant foam.

$\delta(d^6\text{-DMSO}+D_2O)$: 9.44 (1H, s, exchanges with $D_2O$); 7.15–7.26 (5H, complex m.); 7.03–7.05 (2H, d.), 6.81–6.82 (1H, d.); 6.67–6.78 (2H, d.); 6.67–6.69 (2H, d.); 6.35–6.38 (1H, dd.); 5.08 (1H, t.); 4.43–4.44 (2H, d.); 3.94–3.99 (2H, q.); 3.65–3.76 (5H, complex m.); 2.78–2.83 (2H, t.); 2.45–2.76 (3H, complex m.); 0.95–0.96 (3H, d.).

EXAMPLE 40

(SR)-4-{2-[2-Hydroxy-3-(4-hydroxy-3-hydroxymethylphenoxy)propylamino]propyl}phenoxymethylbenzylphosphinic acid, n-butyl ester

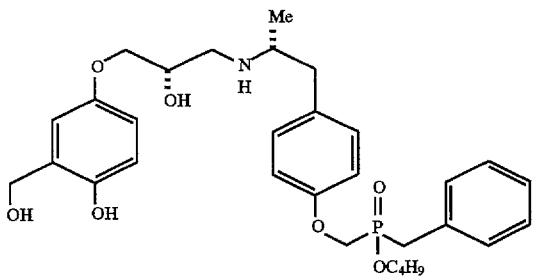

The title compound was prepared from (SR)-4-{2-[3-(2,2-di-t-butyl-4H-1,3,2-benzodioxasilinan-6-yloxy)-2-hydroxypropylamino]propyl}phenoxy methylbenzylphosphinic acid, n-butyl ester according to the procedure described in Example 5. The compound was used in the next stage without further purification.

δ(CDCl$_3$+D$_2$O): 7.24–7.26 (5H, s.); 7.05–7.09 (2H, d.); 6.65–6.72 (3H, complex m.); 6.40–6.62 (3H, complex m.); 4.58 (2H, s.); 3.82–4.08 (4H, complex m.); 3.68–3.72 (2H, d.); 3.25–3.30 (2H, d.); 2.52–3.00 (5H, complex m.); 1.50–1.63 (2H, m.); 1.27–1.39 (2H, m.); 1.03–1.15 (3H, d.); 0.86–0.93 (3H,t.)

EXAMPLE 41

(SR)-4-{2-[2-Hydroxy-3-(4-hydroxy-3-hydroxymethylphenoxy)propylamino]propyl}phenoxymethylbenzylphosphinic acid

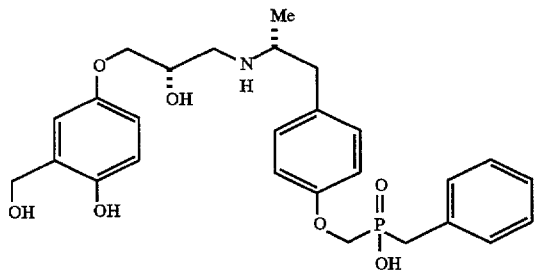

The title compound was prepared from (SR)-4-{2-[2-hydroxy-3-(4-hydroxy-3-hydroxymethyl-phenoxy)propylamino]propyl}phenoxymethylbenzylphosphinic acid, n-butyl ester according to the method described in Example 5 followed by acidification to pH 3.5 with 1M hydrochloric acid, as a solid (mp 180°–183° C.) following chromatography on C18 reverse phase silica-gel, eluting with 40% methanol in water.

δ(d$^6$-DMSO+D$_2$O): 7.00–7.24 (7H, complex m.); 6.94–6.95 (1H, d.); 6.79–6.81 (2H, d.); 6.70–6.72 (1H, d.); 6.61–6.69 (1H, m.); 4.46 (2H, s.); 4.14–4.17 (1H, m.); 3.83–3.91 (1H, m.); 3.64–3.69 (2H, d.); 3.25–3.30 (1H, m).; 2.98–3.29 (5H, complex m.); 2.92–3.00 (2H, d.); 1.03–1.23 (3H, d.)

Pharmacological Data:

The activity of the present compounds is tested by use of the following procedures:

Antagonist and Agonist Activity at Human $\beta_1$, $\beta_2$, and $\beta_3$-Adrenoceptors.

Subclones of CHO cells are stably transfected with each of the human $\beta_1$, $\beta_2$ and $\beta_3$-adrenoceptors[1]. Cells are then disrupted by immersion in ice-cold lysis buffer (10 mM TRIS, 2 mM EDTA, pH 7.4) containing protease inhibitors leupeptin and benzamidine (5 μg/ml) and soyabean trypsin inhibitor (10 μg/ml). Membranes are prepared by the method of Bouvier el. al.[2] and stored in 1 ml aliquots in liquid N$_2$ for future use.

$\beta_3$-Adrenoceptor-Mediated Adenylyl Cyclase Activity

Adenylyl cyclase activity is assayed by the method of Kirkham et. al.[3] by the addition of 40 μl (70–80 μg protein) to the incubation medium of the above CHO cell plasma membranes transfected with the human $\beta_3$-adrenoceptor. cAMP produced over 20 minutes is separated from ATP by the method of Salomon et al.[4]. Agonist EC$_{50}$ values and intrinsic activities are expressed as the concentration of agonist producing 50% activation of adenylyl cyclase and the maximum response produced by each agonist relative to that produced by (−) isoprenaline respectively.

Antagonist Binding at $\beta_1$, and $\beta_2$-Adrenoceptors

Displacement of [$^{125}$I]-iodocyanopindolol from CHO cell plasma membranes transfected with either the human $\beta_1$, or $\beta_2$-adrenoceptors is carried out by the method of Blin et. al.[5]. Ki values (nM) are calculated from the binding IC$_{50}$ values for each agonist, using the Cheng-Prusoff equation.

Results

| Example | Beta-3 EC50 (IA) uM | Beta-1 Ki uM | Beta-2 Ki uM |
|---|---|---|---|
| 17 | 1.1 (0.7) | 21 | 10 |
| 21 | 1.26 (>1.0) | 155 | 15 |
| 29 | 1.7 (0.72) | 288 | 269 |

REFERENCES

1. T. Frielle et. al., Proc. Natl. Acad. Sci., 1987, 84, 7920; B. Kobilka, Proc. Natl. Acad. Sci., 1987, 84, 46; S. Liggett and D. Schwinn, DNA Sequence, 1991, 2, 61.
2. M. Bouvier et. al., Mol. Pharmacol., 1987, 33, 133.
3. D. Kirkham et. al., Biochem. J., 1992, 284, 301.
4. Y. Salomon et al., Anal. Biochem., 1974, 58, 541.
5. N. Blin, et. al., Br. J. Pharmacol., 1994, 112, 911.

We claim:

1. A compound of formula (I):

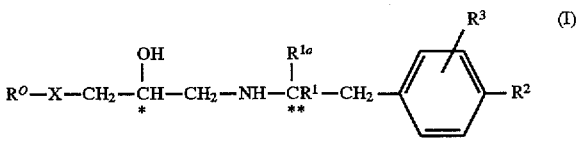

or a pharmaceutically acceptable salt thereof, or a pharmaceutically acceptable solvate thereof, wherein, R$^0$ represents an aryl group optionally substituted with one, two or three substituents selected from the list consisting of: hydroxy, hydroxymethyl, nitro, amino, alkylamino, dialkylamino, alkylsulphonamido, arylsulphonamido, formamido, halogen, alkoxy and allyl;

X represents O or S;

R$^1$ and R$^{1a}$ each independently represents hydrogen or an alkyl group;

$R^2$ represents a moiety of formula (b):

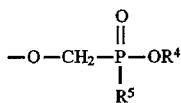

wherein $R^4$ represent hydrogen, alkyl, hydroxyalkyl, arylalkyl, aralkyloxyalkyl or cycloalkyl and $R^5$ represent hydroxy, alkoxy, arylalkyloxy, hydroxyalkyloxy, alkoxyalkyloxy, arylalkoxyalkyloxy or cycloalkyloxy or $R^5$ represents hydrogen, alkyl, substituted alkyl, cycloalkyl, aryl, arylalkyl, arylalkyloxyalkyl or $R^5$ together with $OR^4$ represents $O(CH_2)_nO$ wherein n is 2, 3 or 4; and $R^3$ represents hydrogen, halogen, alkyl or alkoxy.

2. A compound according to claim 1, wherein $R^o$ represents a phenyl group optionally substituted with hydroxy and/or hydroxymethyl.

3. A compound according to claim 1, wherein $R^o$ is 4-hydroxy-3-hydroxymethylphenyl, 3-hydroxyphenyl or 4-hydroxyphenyl.

4. A compound according to claim 1, wherein $R^1$ is an alkyl group and $R^{1a}$ represents hydrogen.

5. A compound according to claim 1, wherein $R^1$ and $R^{1a}$ each represents hydrogen.

6. A compound according to claim 1, wherein $R^4$ represents hydrogen, alkyl, hydroxyalkyl, phenylalkyl, benzyloxyalkyl or cycloalkyl.

7. A compound according to claim 1, wherein $R^4$ represents hydrogen, ethyl, n-butyl, hydroxypropyl, phenylpropyl or benzyloxyethyl.

8. A compound according to claim 1, wherein $R^4$ represents hydrogen or alkyl.

9. A compound according to claim 1, wherein $R^5$ represents hydroxy, alkoxy, arylalkyloxy, hydroxyalkyloxy, alkoxyalkyloxy, arylalkoxyalkyloxy or cycloalkyloxy, especially alkoxy, hydroxyalkyloxy or arylalkoxyalkyloxy.

10. A compound according to claim 1, wherein $R^5$ is hydrogen, phenyl, n-hexyl, cyclohexyl, ethoxy, n-butoxy, phenylpropyloxy, benzyloxypropyloxy, 2-hydroxyethyloxy group or 3-hydroxypropyloxy.

11. A compound according to claim 1, wherein $R^5$ n-hexyl or phenyl.

12. A compound according to claim 1, wherein with reference to formula (I), the asymmetric carbon atom corresponding to that indicated by a single asterisk (*) is in the S-configuration and the asymmetric carbon atom corresponding to that indicated by two asterisks (**) is in the R-configuration.

13. A compound of formula (I) of claim 1, or a pharmaceutically acceptable salt thereof; or a pharmaceutically acceptable solvate thereof, selected from the list consisting of:

(S,R)-4-{2-[2-hydroxy-3-(4-hydroxy-3-hydroxymethylphenoxy)propylamino]propyl}phenoxymethyl phosphonic acid diethyl ester;

(S,R)-(4-{2-[2-hydroxy-3-(4-hydroxy-3-hydroxymethylphenoxy)propylamino]propyl}phenoxymethyl)ethyl phosphonic acid;

(SR)-4-{2-[2-hydroxy-3-(4-hydroxy-3-hydroxymethylphenoxy)propylamino]propyl}phenoxymethylphosphonic acid, ethyl ester;

(S)-4-{2-[2-hydroxy-3-(4-hydroxy-3-hydroxymethylphenoxy)propylamino]ethyl}phenoxymethylphosphonic acid, diethyl ester;

(S)-4-{2-[2-hydroxy-3-(4-hydroxy-3-hydroxymethylphenoxy)propylamino]ethyl}phenoxymethylphosphonate, ethyl ester;

(SR)-4-{2-[2-hydroxy-3-(4-hydroxy-3-hydroxymethylphenoxy)propylamino]propyl}phenoxymethylphosphonic acid, bis-(3-benzyloxypropyl)ester;

(SR)-4-{2-[2-hydroxy-3-(4-hydroxy-3-hydroxymethylphenoxy)propylamino]propyl}phenoxymethylphosphonic acid, (3-benzyloxypropyl)ester;

(SR)-4-{2-[2-hydroxy-3-(4-hydroxy-3-hydroxymethylphenoxy)propylamino]propyl}phenoxymethylphosphonic acid, bis-(3-hydroxypropyl)ester;

(SR)-4-{2-[2-hydroxy-3-(4-hydroxy-3-hydroxymethylphenoxy)propylamino]propyl}phenoxymethylphosphonic acid, mono-(3-hydroxypropyl)ester;

(SR)-4-{2-[2-hydroxy-3-(4-hydroxy-3-hydroxymethylphenoxy)propyl amino]propyl}phenoxymethylphenylphosphinic acid, ethyl ester;

(SR)-4-{2-[2-hydroxy-3-(4-hydroxy-3-hydroxymethylphenoxy)propylamino]propyl}phenoxymethyl-phenylphosphinic acid;

(S)-4-{2-[2-hydroxy-3-(4-hydroxy-3-hydroxymethylphenoxy)propylamino]ethyl}phenoxymethyl-(3-benzyloxypropyl)phosphinic acid, n-butyl ester;

(S)-4-{2-[2-hydroxy-3-(4-hydroxy-3-hydroxymethylphenoxy)propylamino]ethyl}phenoxymethyl-(3-benzyloxypropyl)phosphinic acid;

(SR)-4-{2-[2-hydroxy-3-(4-hydroxy-3-hydroxymethylphenoxy)propylamino]propyl}phenoxymethyl(3-benzyloxypropyl)phosphinic acid, n-butyl ester;

(SR)-4-{2-[2-hydroxy-3-(4-hydroxy-3-hydroxymethylphenoxy)propylamino]propyl}phenoxymethyl(3-benzyloxypropyl)phosphinic acid;

(S)-{2-[2-hydroxy-3-(4-hydroxy-3-hydroxymethylphenoxy)propylamino]ethyl}phenoxymethylcyclohexylphosphinic acid, n-butyl ester;

(S)-4-{2-[2-hydroxy-3-(4-hydroxy-3-hydroxymethylphenoxy)propylamino]ethyl}phenoxymethylcyclohexyl phosphinic acid;

(S)-4-{2-[2-hydroxy-3-(4-hydroxyphenoxy)propylamino]ethyl}phenoxymethylcyclohexylphosphinic acid, n-butyl ester;

(S)-4-{2-[2-hydroxy-3-(4-hydroxyphenoxy)propylamino]ethyl}phenoxymethylcyclohexylphosphinic acid;

(S)-4-[2-[2-hydroxy-3-(3-hydroxyphenoxy)propylamino]ethyl}phenoxymethylcyclohexylphosphinic acid, n-butyl ester;

(S)4-{2-[2-hydroxy-3-(3-hydroxyphenoxy)propylamino]ethyl}phenoxymethylcyclohexylphosphinic acid;

(SR)-4-{2-[2-hydroxy-3-(4-hydroxy-3-hydroxymethylphenoxy)propylamino]propyl}phenoxymethylcyclohexylphosphinic acid, n-butyl ester;

(SR)-4-{2-[2-hydroxy-3-(4-hydroxy-3-hydroxymethylphenoxy)propylamino]propyl}phenoxymethylcyclohexylphosphinic acid;

(SR)-4-{2-[2-hydroxy-3-(4-hydroxy-3-hydroxymethylphenoxy)propylamino]propyl}phenoxymethyl-n-hexyl phosphinic acid, n-butyl ester;

(SR)-4-{2-[2-hydroxy-3-(4-hydroxy-3-hydroxymethylphenoxy)propylamino]propyl}phenoxymethyl-n-hexylphosphinic acid;

(S)-4-{2-[2-hydroxy-3-(4-hydroxyphenoxy)propylamino]ethyl}phenoxymethyl-n-hexylphosphinic acid, n-butyl ester;

(S)4-{2-[2-hydroxy-3-(4-hydroxyphenoxy)propylamino]ethyl}phenoxymethyl-n-hexylphosphinic acid;

(SR)-4-{2-[2-hydroxy-3-(4-hydroxy-3-hydroxymethylphenoxy)propylamino]propyl}phenoxymethylphosphonic acid, bis-(2-phenylethyl)ester;

(SR)-4-{2-[2-hydroxy-3-(4-hydroxy-3-hydroxymethylphenoxy)propylamino]propyl}phenoxymethylphosphonic acid, 2-phenylethyl ester;

(SR)-4-{2-[2-hydroxy-3-(4-hydroxy-3-hydroxymethylphenoxy)propylamino]propyl}phenoxymethylbenzylphosphinic acid, n-butyl ester;

(SR)-4-{2-[2-hydroxy-3-(4-hydroxy-3-hydroxymethylphenoxy)propylamino]propyl}phenoxymethylbenzylphosphinic acid.

14. A pharmaceutical composition comprising a compound of formula (I) according to claim 1, or a pharmaceutically acceptable salt thereof; or a pharmaceutically acceptable solvate thereof, and a pharmaceutically acceptable carrier therefor.

15. A method for treating hyperglycaemia, obesity, atherosclerosis, hyperinsulinaemia, gastrointestinal disorders or the treatment of gastrointestinal ulcerations in a human or non-human mammal, which comprises administering an effective, non-toxic, amount of a compound of formula (I) according to claim 1, or a pharmaceutically acceptable salt thereof; or a pharmaceutically acceptable solvate thereof, to the human or non-human mammal in need thereof.

16. A method for increasing weight gain and/or improving the feed utilization efficiency and/or increasing lean body mass and/or decreasing birth mortality rate and increasing post/natal survival rate; of livestock, which method comprises the administration to livestock of an effective non-toxic amount of a compound of formula (I) according to claim 1, or a veterinarily acceptable salt thereof; or a veterinarily acceptable solvate thereof.

17. A veterinarily acceptable premix formulation comprising a compound of formula (I) according to claim 1, or a veterinarily acceptable salt thereof; or a veterinarily acceptable solvate thereof, in association with a veterinarily acceptable carrier therefore.

* * * * *